(12) United States Patent
Shen et al.

(10) Patent No.: US 10,227,324 B2
(45) Date of Patent: Mar. 12, 2019

(54) 2-MORPHOLIN-4,6-DISUBSTITUTED PYRIMIDINE DERIVATIVE, AND PREPARATION METHOD AND PHARMACEUTICAL USE THEREOF

(71) Applicants: Shanghai Haiyan Pharmaceutical Technology Co., Ltd., Shanghai (CN); Yangtze River Pharmaceutical Group Co., Ltd., Jiangsu (CN)

(72) Inventors: Sida Shen, Shanghai (CN); Xiaojing Ni, Shanghai (CN); Zhiyuan Zhang, Shanghai (CN); Zheng Yang, Shanghai (CN); Xiangyu He, Shanghai (CN); Weiwei Wang, Shanghai (CN); Fusheng Zhou, Shanghai (CN)

(73) Assignees: SHANGHAI HAIYAN PHARMACEUTICAL TECHNOLOGY CO., LTD., Shanghai (CN); YANGTZE RIVER PHARMACEUTICAL GROUP CO., LTD., Jiangsu (CN)

( * ) Notice: Subject to any disclaimer, the term of this patent is extended or adjusted under 35 U.S.C. 154(b) by 0 days.

(21) Appl. No.: 15/537,002

(22) PCT Filed: Dec. 17, 2015

(86) PCT No.: PCT/CN2015/097739
§ 371 (c)(1),
(2) Date: Jun. 16, 2017

(87) PCT Pub. No.: WO2016/095833
PCT Pub. Date: Jun. 23, 2016

(65) Prior Publication Data
US 2017/0349568 A1 Dec. 7, 2017

(30) Foreign Application Priority Data

Dec. 17, 2014 (CN) .......................... 2014 1 0790769

(51) Int. Cl.
*C07D 401/04* (2006.01)
*C07D 403/04* (2006.01)
*A61K 31/5377* (2006.01)
*C07D 401/14* (2006.01)
*C07D 413/14* (2006.01)
*C07D 239/42* (2006.01)

(52) U.S. Cl.
CPC ........ *C07D 401/04* (2013.01); *A61K 31/5377* (2013.01); *C07D 239/42* (2013.01); *C07D 401/14* (2013.01); *C07D 403/04* (2013.01); *C07D 413/14* (2013.01)

(58) Field of Classification Search
None
See application file for complete search history.

(56) References Cited

U.S. PATENT DOCUMENTS

2009/0018134 A1  1/2009  Pike et al.

FOREIGN PATENT DOCUMENTS

| CN | 101389622 A | 3/2009 |
| JP | 2010533158 A | 10/2010 |
| JP | 2012524103 A | 10/2012 |
| JP | 2013541536 A | 11/2013 |
| WO | 2009066084 A1 | 5/2009 |
| WO | 2010120998 A1 | 10/2010 |
| WO | 2012044727 A2 | 4/2012 |
| WO | 2014090147 A1 | 6/2014 |

OTHER PUBLICATIONS

Cancer Drug Design and Discovery Neidle, Stephen, ed. (Elsevier/Academic Press, 2008), Chapter 18.*
Gura, Science Nov. 7, 1997: vol. 278. No. 5340, pp. 1041-1042.*
Roberts, Jr et al., JAMA 292(17): 2130-2140 (2004).*
Int'l Search Report dated Mar. 23, 2016 in Int'l Application No. PCT/CN2015/097739.
Burger et al., "Synthesis and in Vitro and in Vivo Evaluation of Phospoinositide-3-kinase Inhibitors", ACS Med. Chem. Lett., vol. 2, pp. 34-38 (2011).
Brana et al., "Clinical Development of Phosphatidylinositol 3-Kinase Inhibitors for Cancer Treatment", BioMed Central Medicine, vol. 10, No. 161, 15 pgs (2012).
Greenwald et al., "Drug Delivery Systems Based on Trimethyl Lock Lactonization: Poly (ethylene glycol) Prodrugs of Amino-Containing Compounds", J. Med. Chem., vol. 43, pp. 475-487 (2000).
Katso et al., "Cellular Function of Phosphoinositide 3-Kinases: Implications for Development, Immunity, Homeostasis and Cancer", Annu. Rev. Cell. Dev. Biol., vol. 17, pp. 615-675 (2001).
Sauinier et al., "An Efficient Method for the Synthesis of Guanidino Prodrugs", Bioorganic & Medical Chem. Ltr., vol. 4, No. 16, pp. 1985-1990 (1994).
Vivanco et al., "The Phosphatidylinositol 3-Kinase-Aky Pathway in Human Cancer", Nature Reviews, vol. 2, pp. 489-501 (Jul. 2002).
Heavey et al., "Strategies for co-targeting the PI3K/AKT/mTOR Pathway in NSCLC", Cancer Treatment Reviews, vol. 40, pp. 445-456 (2014).

* cited by examiner

*Primary Examiner* — Alicia L Otton
(74) *Attorney, Agent, or Firm* — Panitch Schwarze Belisario & Nadel LLP

(57) ABSTRACT

Disclosed is a 2-morpholin-4,6-disubstituted pyrimidine derivative as shown in formula (1) below, and a pharmaceutically acceptable salt, solvate, stereoisomer or prodrug thereof, and a pharmaceutical composition thereof and a use thereof, wherein the definition of each group is as shown in the description. The compound has a PI3K kinase inhibition activity, and has a relatively high inhibitive ability and a low cytotoxicity against PIK3CA mutant breast cancer cell strains T47D and MCF-7.

24 Claims, No Drawings

2-MORPHOLIN-4,6-DISUBSTITUTED PYRIMIDINE DERIVATIVE, AND PREPARATION METHOD AND PHARMACEUTICAL USE THEREOF

CROSS-REFERENCE TO RELATED APPLICATION

This application is a Section 371 of International Application No. PCT/CN2015/097739, filed Dec. 17, 2015, which was published in the Chinese language on Jun. 23, 2016, under International Publication No. WO 2016/095833 A1, and the disclosure of which is incorporated herein by reference.

TECHNICAL FIELD

The present invention relates to the field of pharmaceutical technology, and more particularly to cancer drugs, in particular to a 2-morpholin-4,6-disubstituted pyrimidine derivative, or a pharmaceutically acceptable salt, solvate, stereoisomer or prodrug thereof, and a pharmaceutical composition thereof and a use thereof.

BACKGROUND ART

With the deepening of tumor genetics and biology research, multiple intracellular tumor-related key signaling pathways have been found. Tumor cells rely on these pathways to achieve intracellular transduction of extracellular signals and regulate their own sustained proliferation, invasion, metastasis, anti-apoptosis and other activities, thereby maintaining their malignant phenotypic characteristics on one hand and gaining tolerance against treatment through regulating specific genes and protein products thereof on the other hand. Studies have revealed that the transduction pathway mediated by the phosphatidylinositol 3-kinase (PI3K)-AKT-mammalian rapamycin target (mTOR) plays an important role in some cellular processes including proliferation and survival, and malfunction of these pathways is pathogenic factor for a wide range of human cancers and other disease profiles (Katso et al., Annual Rev. Cell Dev. BioL, 2001, 17: 615-617).

Phosphatidylinositol 3-kinase (PI3K) belongs to the family of lipokines and can be divided into three classes according to their structural characteristics and substrate selectivity. Class 1 PI3K, the most intensively studied, is a heterodimer protein which is composed of subunits with catalytic function (p110α, p110β, p110δ and p110γ) and subunits with regulatory function (p85α, p85β, p50α, p55α and p55γ), respectively. Type 1a PI3K enzyme subunits p100α and p100β are always co-expressed in various cell types, while the expression of p110δ is more restricted by leukocyte populations and some epithelial cells. Type 1b PI3K enzyme consists of p110γ catalytic subunit interacting with p101 regulatory subunit, and mainly distributes in leukocytes, platelets and cardiomyocytes. Wherein p85 regulatory subunit is activated via phosphorylation through interaction with the receptor tyrosine kinase. The amino terminus of p85 contains a SH3 domain and a proline enriched region which is capable of binding to the SH3 domain, and its carboxyl terminus contains two SH2 domains and one p110-binding region. The p110 subunit has homology with protein kinase, and this subunit itself has both serine/threonine protein kinase activity and phosphatidylinositol kinase activity, and can convert phosphatidylinositol diphosphate (PI2P) to phosphatidylinositol triphosphate (PI3P), wherein the latter can in turn activate a number of downstream signaling molecules, thereby accomplishing the continuing transmission of extracellular signals.

Studies have shown that Type 1a PI3K enzymes can directly or indirectly promote the occurrence of human cancer (Vivanco and Sawyers, Nature Reviews Cancer, 2002, 2, 489-501). For example, the gene PIK3CA is widely amplified or mutated in various cancers, and the activation mutations in the catalytic site of the p110α subtype encoded by this gene are associated with various other tumors such as tumors of colon or rectum, mammary gland and lung. The expression of p110β is approximately 5% amplified in severe epithelial ovarian cancer, breast cancer and PTEN-lacking tumor cell lines. p110δ is associated with immuno-suppression and is commonly used in transplant rejection and autoimmune diseases. In addition to the direct effect, Type 1a PI3K can indirectly trigger tumors by causing a variety of downstream signaling events. For example, by activating Akt, PI3K-mediated signaling events are enhanced, leading to various cancers. A large number of studies have shown that different PI3K subtypes have different roles and the best way to inhibit the growth of malignant cells is to choose the inhibitors that are more specific to a certain p110 subtype than to broadly suppress all Type I PI3K enzymes (Susan and Kenneth, Cancer Treatment Reviews, 2013 Aug. 26. pii: S0305-7372 (13) 00171-0). Currently, unavoidable side effects have been observed for non-selective PI3K inhibitors in clinic, including nausea, vomiting, diarrhea, fatigue, elevated transaminases, hyperglycemia and the like which are commonly seen for PI3K inhibitors. Among the PI3K selective inhibitors, since PIK3CA/p110α is the most common PI3K mutant subtype, the PI3Kα selective inhibitors are also the ones that potentially have the most potent tumor-suppressing effect. At the same time, PI3Kα selective inhibitors can also, to the greatest extent, avoid pneumonia, neutropenia, thrombocytopenia, anemia, elevated transaminase and other side effects caused by PI3Kβ and PI3Kδ inhibitors in clinic (Brana and Siu, BMC Medicine, 2012, 10: 161).

PI3K is a key regulatory pathway for cell function. Its abnormal signaling is closely related to the activation of proto-oncogene, and PI3K thus has a critical effect on the onset and development of tumor. Therefore, it can be expected that developing small molecule compounds to inhibit PI3K as a tumor treatment drug has a promising prospect.

For PI3K signaling pathways, there are currently a number of compounds independently inhibiting PI3K activity under development and clinical trials. For example, the PI3K inhibitor, BKM-120, developed by Novartis, is now in phase III clinical stage for breast cancer. Another PI3K inhibitor, BYL-719, developed by Novartis for the treatment of solid tumors, and head and neck cancer, is also in clinical phase III now.

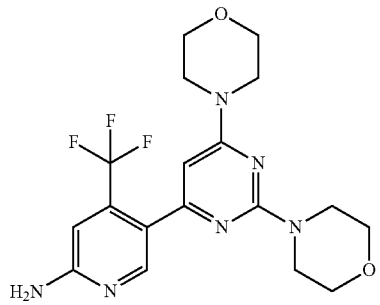

BKM-120

3

Therefore, the development of medicaments against PI3K with higher activity, better selectivity, and less toxicity is of great significance.

SUMMARY OF THE INVENTION

The object of the present invention is to overcome the above-mentioned disadvantages of the prior art by providing a compound with higher activity, better selectivity, and less toxicity, or a pharmaceutically acceptable salt, solvate, stereoisomer, or prodrug thereof, and pharmaceutical compositions and use thereof.

In order to achieve the object stated above, the first aspect of the present invention is to provide a compound as shown in formula (I), or a pharmaceutically acceptable salt, solvate, stereoisomer or prodrug thereof.

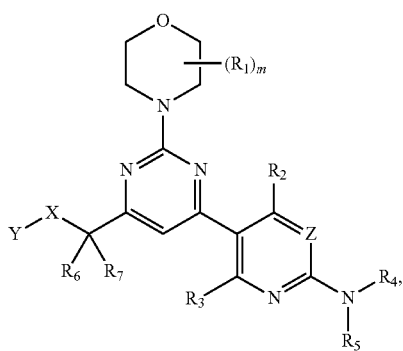

I wherein, Z is N or $CR_0$;

$(R_1)_m$ means that the hydrogen atom(s) on the morpholine ring is substituted by $R_1$ and the number of $R_1$ is m, wherein, m is 0, 1, 2, 3, 4, 5 or 6, each $R_1$ is the same or different and is independently selected from the group consisting of hydrogen, deuterium, $C_{1-10}$ alkyl, deuterated $C_{1-10}$ alkyl and $C_{1-10}$ haloalkyl; or any two $R_1$ are linked by a single bond or —$(CH_2)_p$—, wherein p is 1, 2, 3, 4, 5 or 6;

$R_2$ and $R_3$ are each independently selected from the group consisting of hydrogen, halogen, $C_{1-10}$ alkyl, $C_{1-10}$ haloalkyl, $C_{1-10}$ alkoxy, $C_{3-8}$ cycloalkoxy, —$COC_{1-10}$ alkyl, —$CON(C_{1-10}$ alkyl$)_2$, —$C(O)OC_{1-10}$ alkyl and —$OC(O)C_{1-10}$ alkyl;

$R_4$ and $R_5$ are each independently selected from the group consisting of hydrogen, $C_{1-10}$ alkyl, $C_{1-10}$ haloalkyl or $C_{3-10}$ cycloalkyl;

$R_6$ and $R_7$ are each independently selected from the group consisting of hydrogen, halogen, $C_{1-10}$ alkyl or $C_{1-10}$ haloalkyl, or $R_6$ and $R_7$, together with the carbon atom to which they are attached, form a 3- to 10-membered saturated or 3- to 6-membered unsaturated monocyclic ring, or 3- to 10-membered saturated or partially unsaturated mono-heterocyclic ring containing 1-3 heteroatoms independently selected from the group consisting of nitrogen, oxygen and sulfur;

X is a bond, —$(CR_aR_b)_r$—, —$N(R_c)$— or —$C(O)$—; Y is selected from the group consisting of —$SO_2R_8$, —$OR_9$, halogen, $C_{1-10}$ haloalkyl, —$N(R_{81}R_{82})_2$, —$C(O)C_{1-10}$ alkyl, 5- to 6-membered monocyclic heteroaryl ring, 8- to 10-membered bicyclic heteroaryl ring, 3- to 10-membered saturated or partially unsaturated monocyclic ring or 3- to 10-membered saturated or partially unsaturated mono-heterocyclic ring.

4

Preferably, $R_0$ is selected from the group consisting of hydrogen, halogen, $C_{1-10}$ alkyl and $C_{1-10}$ haloalkyl; $R_a$, $R_b$, and $R_c$ are each independently hydrogen or $C_{1-10}$ alkyl;

r is 1, 2 or 3;

$R_8$ is selected from the group consisting of hydroxy, halogen, —$N(R_{81}R_{82})_2$, —$OC_{1-10}$ alkyl, $C_{1-10}$ alkyl, $C_{1-10}$ haloalkyl, $C_{6-10}$ aryl, $C_{3-10}$ cycloalkyl, —$(CR_aR_b)_r$—$C_{6-10}$ aryl and 5- to 6-membered monocyclic heteroaryl ring, wherein said aryl is unsubstituted or substituted with 1 to 5 substituents selected from the group consisting of halogen, $C_{1-10}$ alkyl;

$R_9$ is selected from the group consisting of hydrogen, $C_{1-10}$ alkyl, $C_{1-10}$ haloalkyl, $C_{6-10}$ aryl, $C_{3-10}$ cycloalkyl, —$(CR_aR_b)_r$—$C_{6-10}$ aryl and —$C(O)C_{1-10}$ alkyl;

$R_{81}$ and $R_{82}$ are each independently hydrogen or $C_{1-10}$ alkyl.

Preferably, when m is 0 or 1, $R_1$ is methyl or $CD_3$; when m is 2, $R_1$ is methyl or $CD_3$, p is 1 or 2.

Preferably, $R_0$ is selected from the group consisting of hydrogen, F, Cl, Br, I, methyl, ethyl, propyl, isopropyl, monofluoroethyl, difluoromethyl and trifluoromethyl.

Preferably, said $C_{1-10}$ alkyl is $C_{1-6}$ alkyl, said $C_{1-10}$ haloalkyl is $C_{1-6}$ haloalkyl, said $C_{3-10}$ cycloalkyl is $C_{3-6}$ cycloalkyl.

Preferably, said $C_{1-6}$ alkyl is $C_{1-3}$ alkyl, said $C_{1-6}$ haloalkyl is $C_{1-3}$ haloalkyl.

Preferably, $R_2$ and $R_3$ are each independently selected from the group consisting of hydrogen, halogen, $C_{1-6}$ alkyl, $C_{1-6}$ haloalkyl, $C_{1-6}$ alkoxy, $C_{3-6}$ cycloalkoxy, —$COC_{1-3}$ alkyl, —$C(O)OC_{1-3}$ alkyl, —$OC(O)C_{1-3}$ alkyl and —$CON(C_{1-3}$ alkyl$)_2$.

Preferably, $R_2$ and $R_3$ are each independently selected from the group consisting of hydrogen, F, Cl, Br, I, methyl, ethyl, propyl, isopropyl, monofluoroethyl, difluoromethyl, trifluoromethyl, methoxy, ethoxy, propoxy, isopropoxy, cyclopropyloxy, cyclobutyloxy, cyclopentyloxy, cyclohexyloxy, —$COCH_3$, —$C(O)OCH_3$, —$OC(O)CH_3$ and —$CON(CH_3)_2$.

Preferably, $R_4$ and $R_5$ are each independently selected from the group consisting of hydrogen, methyl, ethyl, propyl, isopropyl, monofluoroethyl, difluoromethyl, trifluoromethyl, cyclopropyl, cyclobutyl, cyclopentyl and cyclohexyl.

Preferably, $R_6$ and $R_7$ are each independently selected from the group consisting of hydrogen, halogen, $C_{1-6}$ alkyl or $C_{1-6}$ haloalkyl, and $R_6$ and $R_7$ are not hydrogen at the same time; or $R_6$ and $R_7$ together with the carbon atom to which they are attached form a 3- to 6-membered saturated monocyclic ring.

Preferably, $R_6$ and $R_7$ are each independently selected from the group consisting of halogen, $C_{1-6}$ alkyl or $C_{1-6}$ haloalkyl; or $R_6$ and $R_7$ together with the carbon atom to which they are attached form a 3- to 6-membered saturated monocyclic ring.

Preferably, $R_6$ and $R_7$ are halogen, $C_{1-10}$ alkyl or $C_{1-10}$ haloalkyl at the same time; or $R_6$ and $R_7$ together with the carbon atom to which they are attached form a 3- to 6-membered saturated monocyclic ring.

Preferably, $R_6$ and $R_7$ are each independently selected from the group consisting of hydrogen, F, Cl, Br, I, methyl, ethyl, propyl, isopropyl, monofluoromethyl, monofluoroethyl, difluoromethyl and trifluoromethyl, and $R_6$ and $R_7$ are not hydrogen at the same time; or $R_6$ and $R_7$ together with the carbon atom to which they are attached form the following structure:

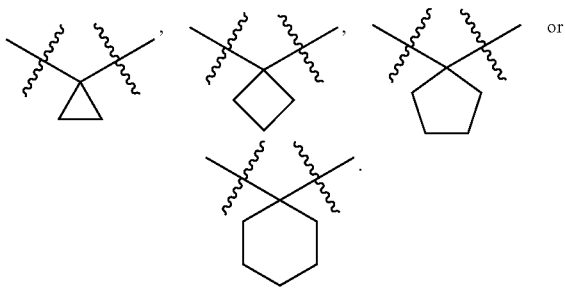

Preferably, $R_6$ and $R_7$ are F, Cl, methyl, ethyl, propyl, isopropyl, monofluoromethyl, monofluoroethyl, difluoromethyl or trifluoromethyl at the same time; or $R_6$ and $R_7$ together with the carbon atom to which they are attached form the following structure:

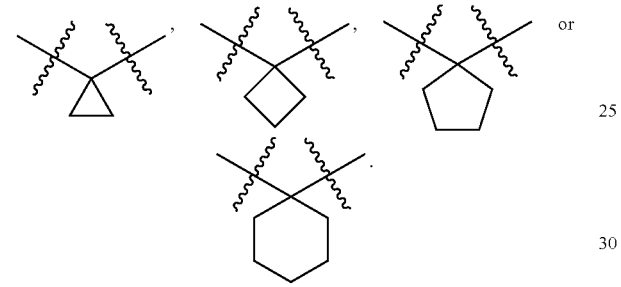

Preferably, $R_8$ is $C_{1-6}$ alkyl, $C_{1-6}$ haloalkyl, substituted or unsubstituted phenyl or $C_{3-8}$ cycloalkyl, wherein said "substituted" means that 1-5 hydrogen atoms on the benzene ring are substituted with a substituent selected from the group consisting of halogen and $C_{1-3}$ alkyl.

Preferably, $R_8$ is methyl, ethyl, propyl, isopropyl, monofluoroethyl, difluoromethyl, trifluoromethyl, substituted or unsubstituted phenyl, cyclopropyl, cyclobutyl, cyclopentyl or cyclohexyl; wherein said "substituted" means that 1-3 hydrogen atoms on the benzene ring are substituted with a substituent selected from the group consisting of F, Cl and $C_{1-3}$ alkyl.

Preferably, $R_9$ is hydrogen or $C_{1-6}$ alkyl.

Preferably, $R_9$ is hydrogen, methyl, ethyl, propyl, isopropyl or tert-butyl.

Preferably, X is a bond, —$CH_2$—, —NH— or —N($CH_3$)—.

Preferably, when X is a bond, Y is 5- to 6-membered monocyclic heteroaryl ring, 8- to 10-membered bicyclic heteroaryl ring, —$SO_2R_8$, —$OR_9$, halogen or $C_{1-10}$ haloalkyl;

when X is —$CH_2$—, Y is —$C(O)C_{1-10}$ alkyl, 3- to 10-membered saturated mono-heterocyclic ring or —$SO_2R_8$;

when X is —C(O)—, Y is —$OR_9$ or 3- to 10-membered saturated mono-heterocyclic ring; or when X is —NH— or —N($CH_3$)—, Y is —$C(O)C_{1-10}$ alkyl or —$SO_2R_8$.

Preferably, said 5- to 6-membered monocyclic heteroaryl ring is selected from the group consisting of thiophene ring, furan ring, thiazole ring, imidazole ring, oxazole ring, pyrrole ring, pyrazole ring, triazole ring, tetrazole ring, isoxazole ring, oxadiazole ring, thiadiazole ring, pyridine ring, pyridazine ring, pyrimidine ring and pyrazine ring.

Preferably, said 5- to 6-membered monocyclic heteroaryl ring is selected from the group consisting of:

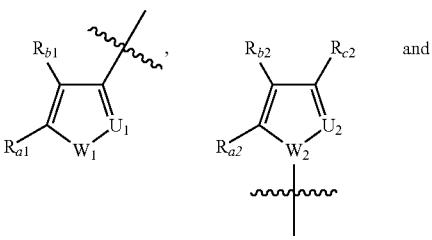

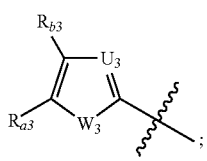

pyridine ring, $W_1$, $W_2$, $W_3$, $U_1$, $U_2$, and U are each independently selected from the group consisting of nitrogen, oxygen and sulfur atom;

$R_{a1}$, $R_{b1}$, $R_{a2}$, $R_{b2}$, $R_{c2}$, $R_{a3}$, and $R_{b3}$ are each independently selected from the group consisting of hydrogen, halogen, $C_{1-6}$ alkyl and $C_{1-6}$ haloalkyl.

Preferably, said 5- to 6-membered monocyclic heteroaryl ring is selected from the group consisting of:

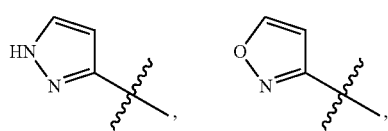

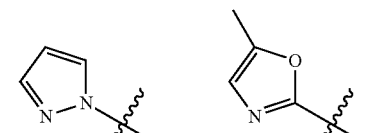

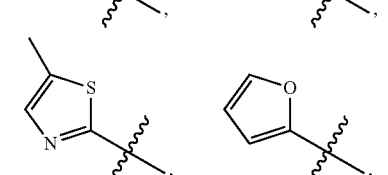

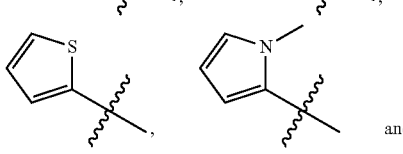

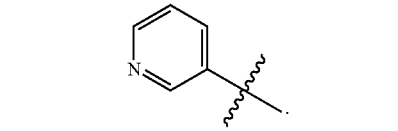

Preferably, said 8- to 10-membered bicyclic heteroaryl ring is

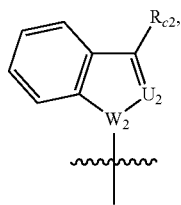

wherein $W_2$ and $U_2$ are each independently selected from the group consisting of nitrogen, oxygen and sulfur atom;

$R_{c2}$ is hydrogen, halogen, $C_{1-6}$ alkyl or $C_{1-6}$ haloalkyl.

Preferably, said 8- to 10-membered bicyclic heteroaryl ring is

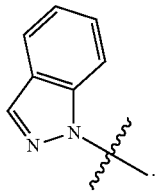 [SMILES: *n1ncc2ccccc21]

Preferably, said 3- to 10-membered saturated mono-heterocyclic ring is selected from:

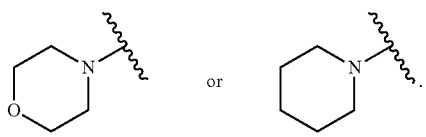 [SMILES: *N1CCOCC1 ; *N1CCCCC1]

Preferably, the compound of formula (I) is shown in formula (I-a),

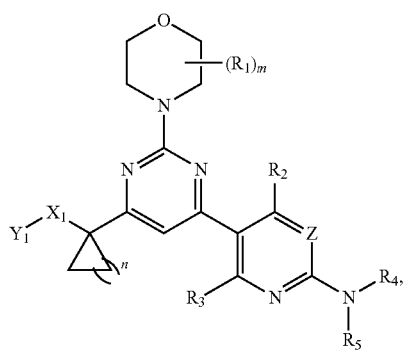

wherein $R_1$, $R_2$, $R_3$, $R_4$, $R_5$, m, and Z are defined as described above, n is 1, 2, 3 or 4;

$X_1$ is a bond, or —CIH$_2$—, —NH— or —N(CH$_3$)—;

$Y_1$ is —SO$_2$R$_8$, —OR$_9$, halogen, $C_{1-10}$ haloalkyl, 5- to 6-membered monocyclic heteroaryl ring, 8- to 10-membered bicyclic heteroaryl ring, 3- to 10-membered saturated or partially unsaturated monocyclic ring or 3- to 10-membered saturated mono-heterocyclic ring.

Preferably, the compound of formula (I) is shown in formula (I-b),

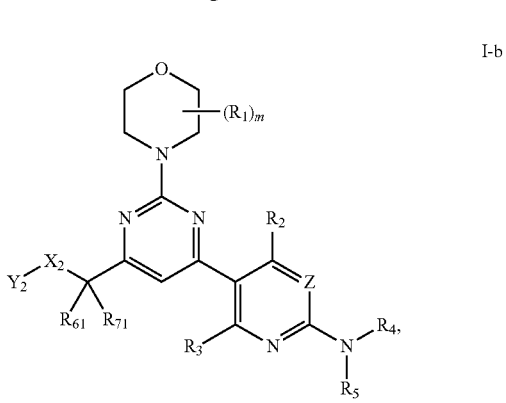

wherein, $R_1$, $R_2$, $R_3$, $R_4$, $R_5$, m, and Z are defined as described above;

$R_{61}$ and $R_{71}$ are each independently selected from the group consisting of hydrogen, halogen, $C_{1-6}$ alkyl and $C_{1-6}$ haloalkyl;

$X_2$ is a bond;

$Y_2$ is —SO$_2$R$_8$, —OR$_9$, halogen or $C_{1-10}$ haloalkyl (preferably $C_{1-6}$ haloalkyl, more preferably $C_{1-3}$ haloalkyl); wherein $R_8$ and $R_9$ are defined as described above.

Preferably, when $X_1$ is a bond, $Y_1$ is 5- to 6-membered monocyclic heteroaryl ring, 8- to 10-membered bicyclic heteroaryl ring, —SO$_2$R$_8$, —OR$_9$, halogen or $C_{1-10}$ haloalkyl;

when $X_1$ is —CH$_2$—, $Y_1$ is —C(O)C$_{1-10}$ alkyl, 3- to 10-membered saturated mono-heterocyclic ring or —SO$_2$R$_8$; or when $X_1$ is —NH— or —N(CH$_3$)—, $Y_1$ is —C(O)C$_{1-10}$ alkyl or —SO$_2$R$_8$.

Preferably, $R_{61}$ is hydrogen, F, Cl, Br, I, methyl, ethyl, propyl, isopropyl, monofluoromethyl, monofluoroethyl, difluoromethyl or trifluoromethyl; $R_{71}$ is hydrogen, F, Cl, Br, I, methyl, ethyl, propyl, isopropyl, monofluoromethyl, monofluoroethyl, difluoromethyl or trifluoromethyl, and $R_{61}$ and $R_{71}$ are not hydrogen at the same time.

Preferably, $R_{61}$ and $R_{71}$ are F, Cl, methyl, ethyl, propyl, isopropyl, monofluoromethyl, monofluoroethyl, difluoromethyl or trifluoromethyl at the same time.

Preferably, the compound of formula (I) is shown in formula (II),

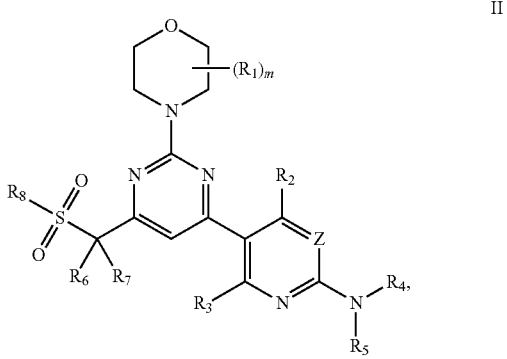

wherein, $R_1$, $R_2$, $R_3$, $R_4$, $R_5$, $R_6$, $R_7$, $R_8$, Z, and m are defined as described above.

Preferably, in formula (II), (i) m is 0 or 1; $R_1$ is hydrogen or methyl;

$R_8$ is methyl, ethyl, propyl, isopropyl, monofluoroethyl, difluoromethyl, trifluoromethyl, cyclopropyl, cyclobutyl, cyclopentyl or cyclohexyl;

Z is CH, CCF$_3$ or N;

$R_2$ is hydrogen, methoxy, F, Cl or trifluoromethyl; $R_3$ is H; $R_4$ is hydrogen or methyl; $R_5$ is hydrogen or methyl;

$R_6$ and $R_7$ are each independently selected from the group consisting of hydrogen, F, Cl, methyl, ethyl, propyl, isopropyl, monofluoromethyl, monofluoroethyl, difluoromethyl or trifluoromethyl; or $R_6$ and $R_7$ together with the carbon atom to which they are attached form the following structure:

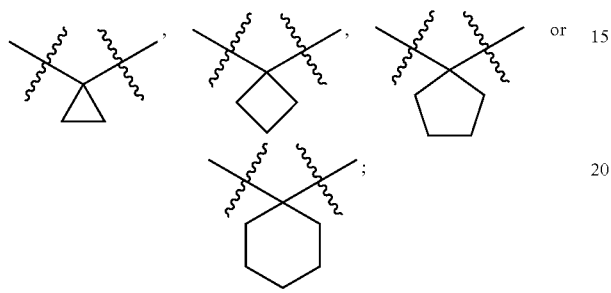

or (ii) m is 0; Z is CH;

$R_2$ is F, Cl or trifluoromethyl; $R_3$ is H; $R_4$ and $R_5$ are H;

$R_8$ is substituted or unsubstituted phenyl; wherein said "substituted" means that 1, 2 or 3 hydrogen atoms on the benzene ring are substituted with F or Cl;

$R_6$ and $R_7$ are each independently methyl; or $R_6$ and $R_7$ together with the carbon atom to which they are attached form the following structure:

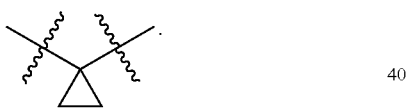

Preferably, the compound of formula (I) is shown in formula (III):

III

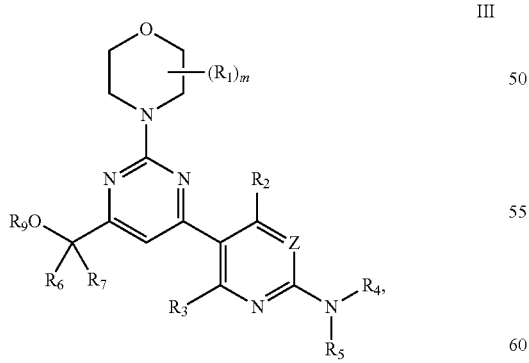

wherein, $R_1$, $R_2$, $R_3$, $R_4$, $R_5$, $R_6$, $R_7$, $R_9$, Z and m are defined as described above.

Preferably, the compound of formula (I) is shown in formula (I-a-1), formula (I-a-2), formula (I-b-1) or formula (I-b-2):

I-a-1

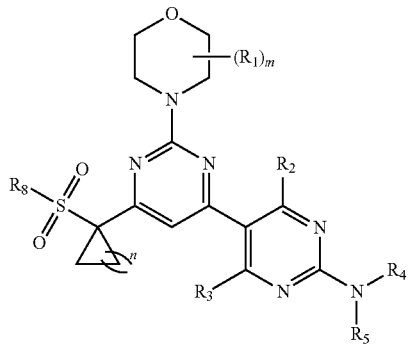

I-a-2

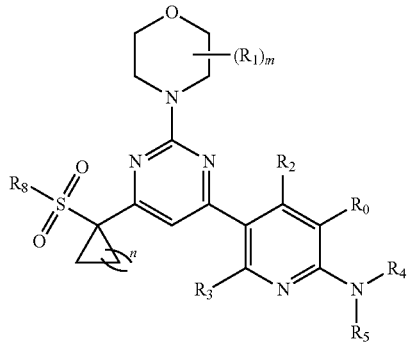

I-b-1

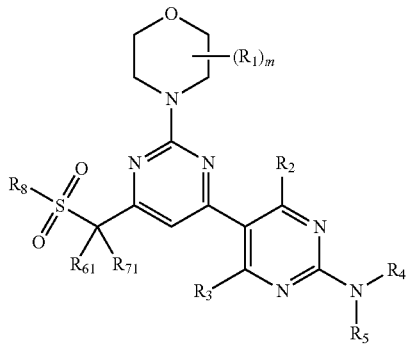

I-b-2

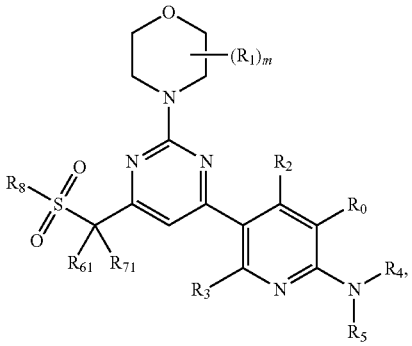

wherein, $R_0$, $R_1$, $R_2$, $R_3$, $R_4$, $R_5$, $R_8$, n, m, $R_{61}$, and $R_{71}$ are defined as described above.

Preferably, the compound of the present invention is anyone of the compounds represented by the following chemical structural formulas:

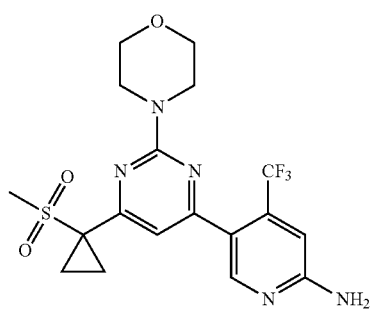
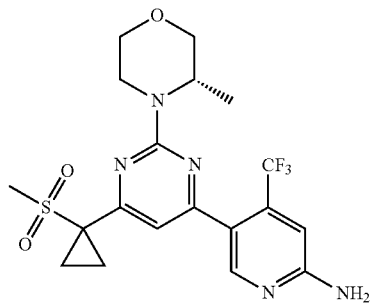
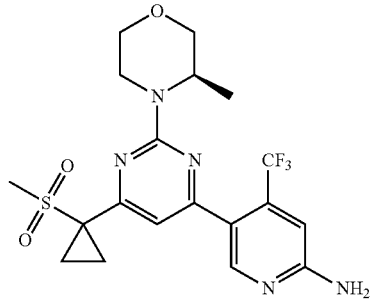
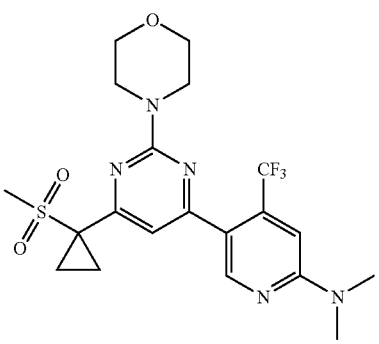
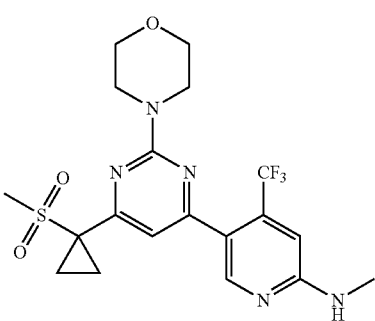
-continued
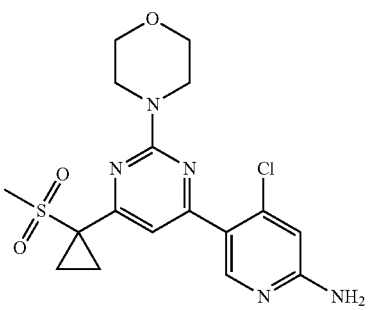
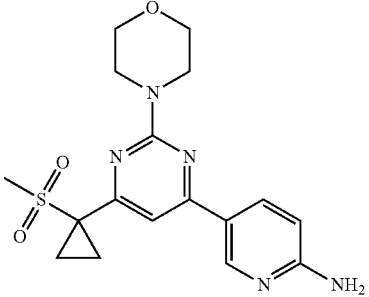
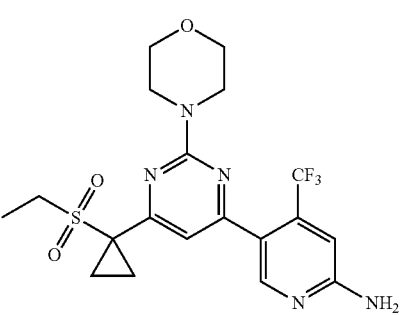
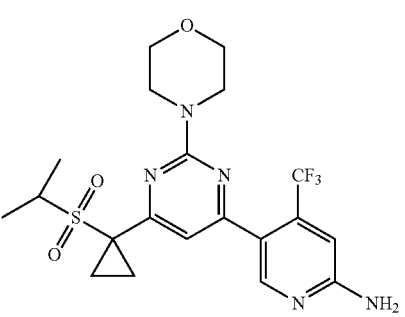
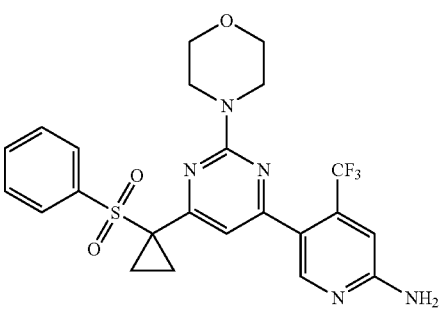

-continued
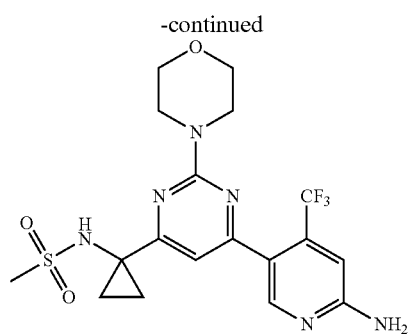
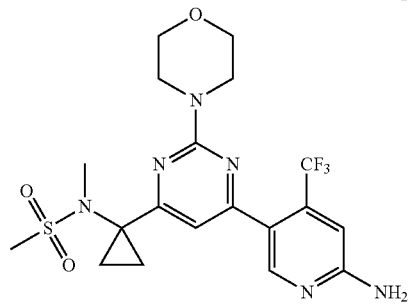
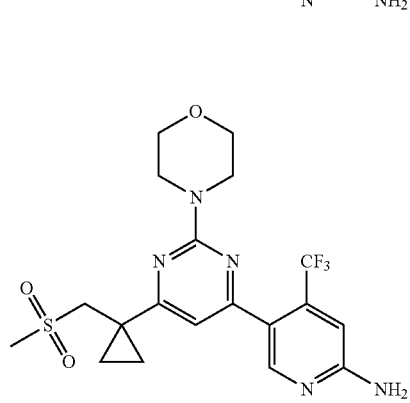
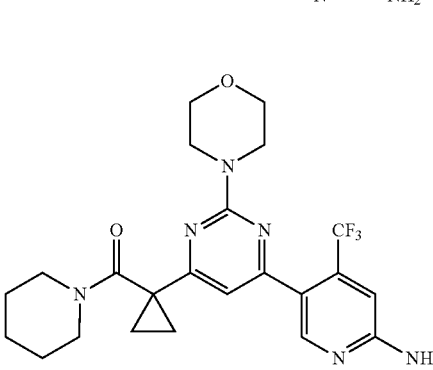
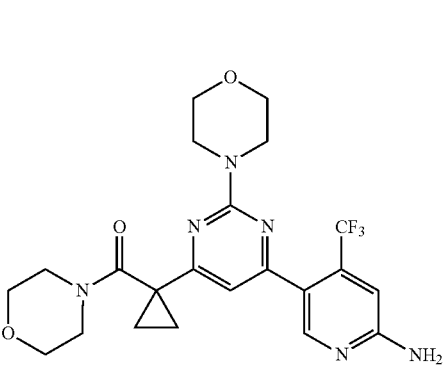
-continued
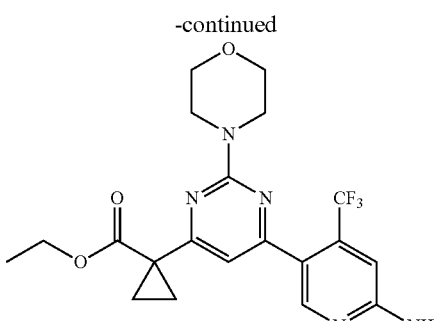
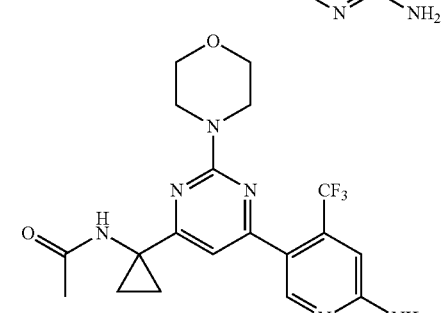
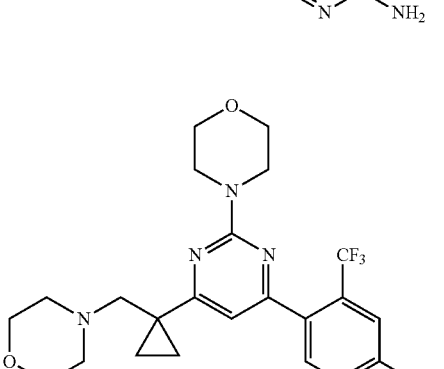
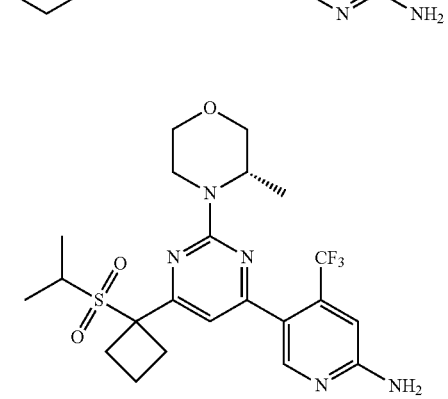
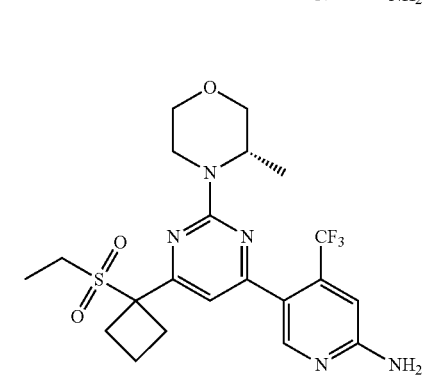

-continued
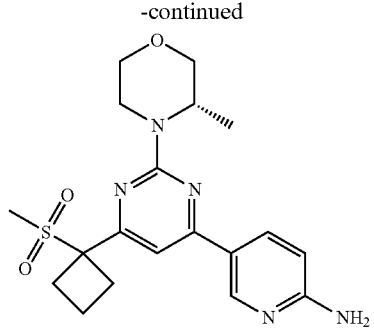
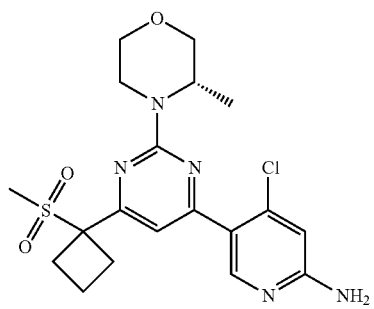
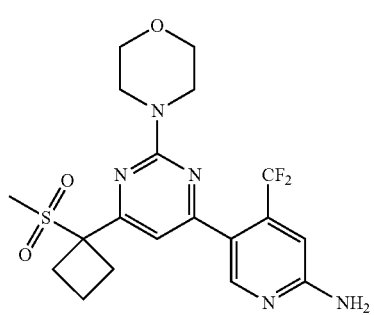
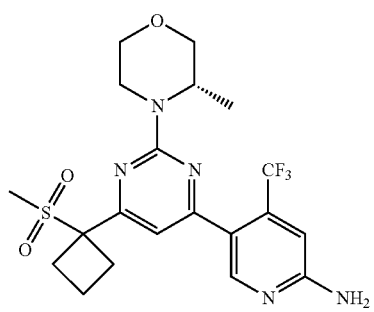
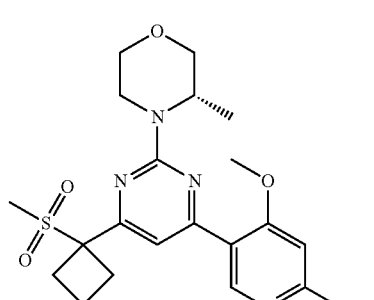
-continued
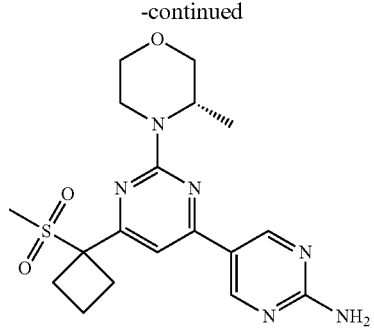
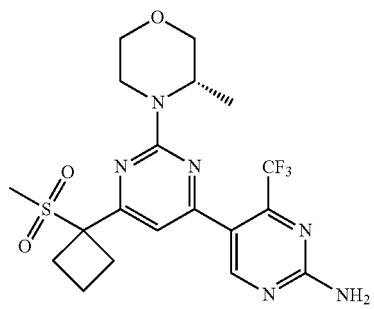
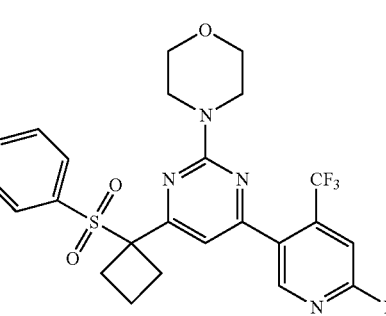
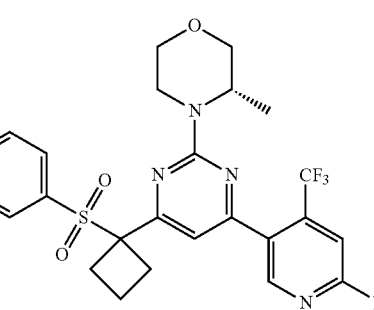
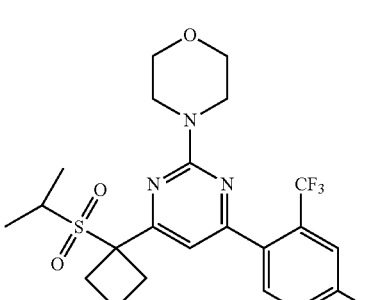

-continued
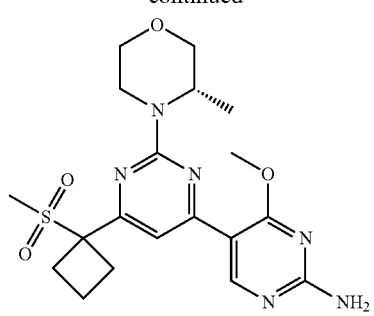
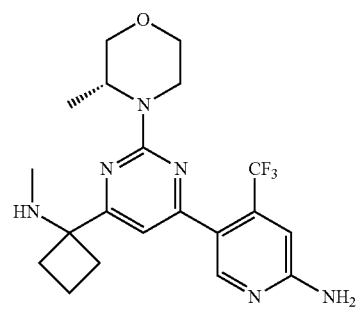
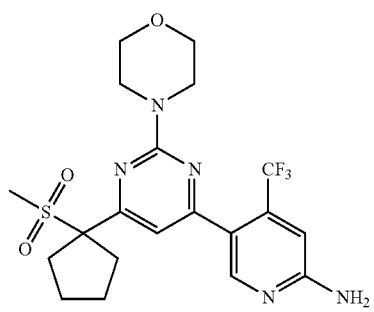
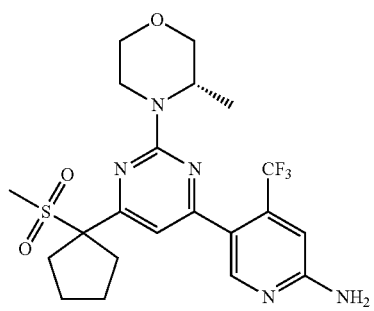
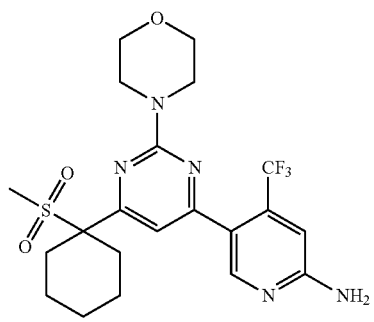
-continued
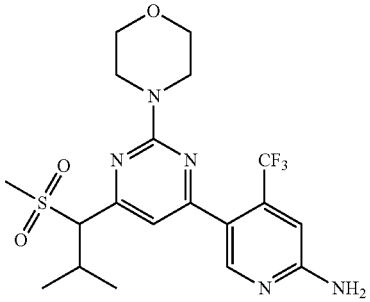
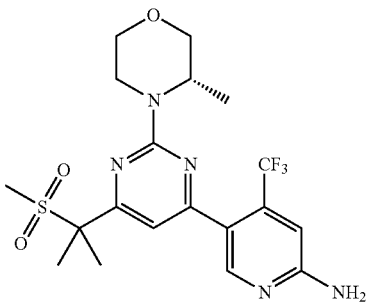
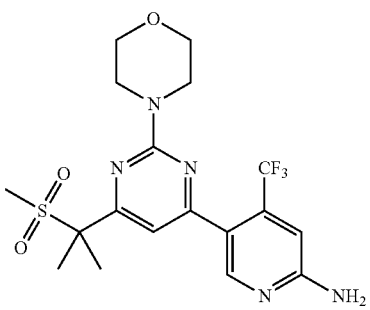
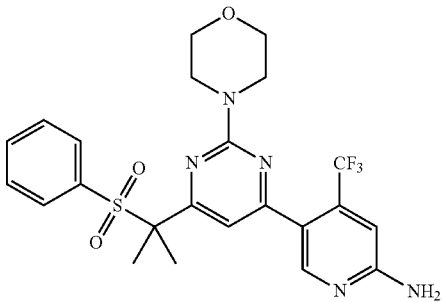
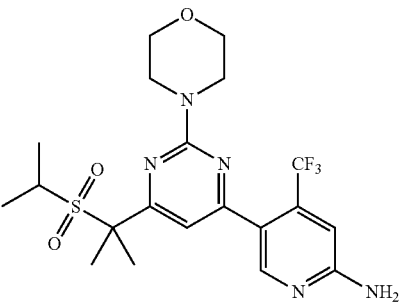

-continued
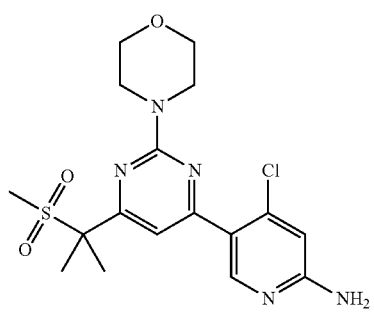
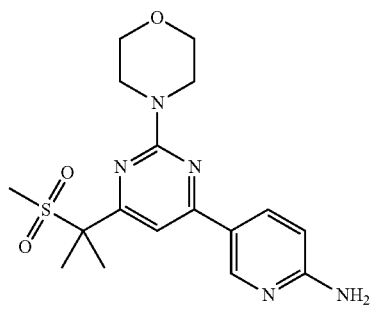
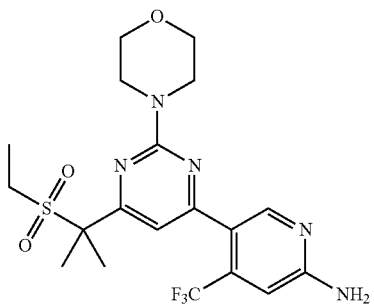
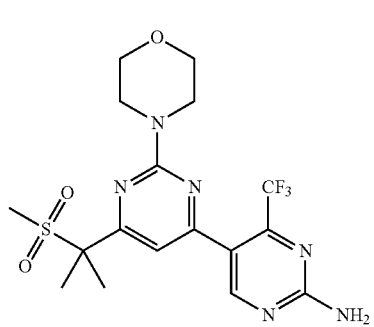
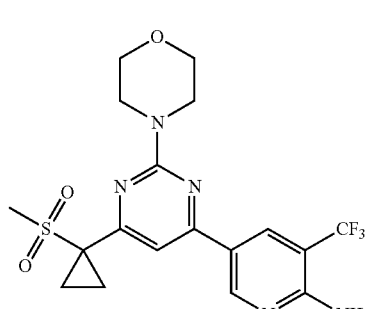
-continued
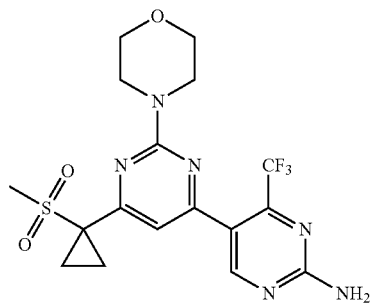
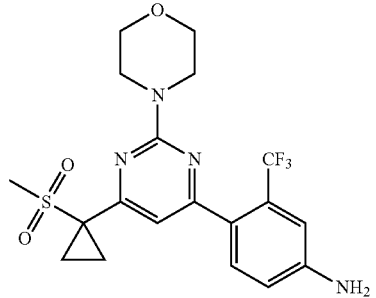
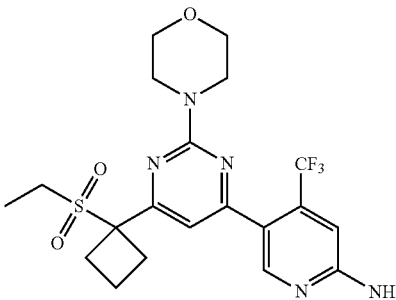
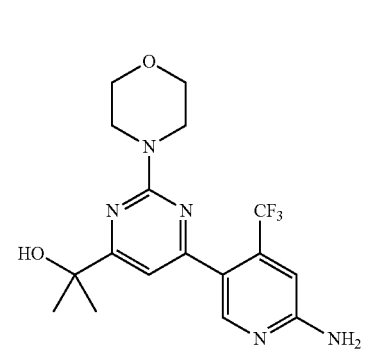
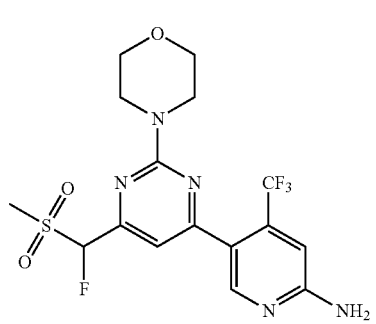

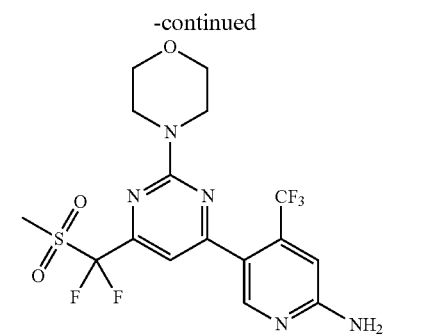
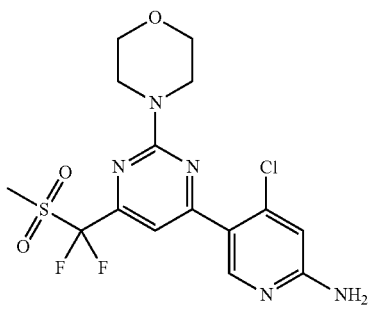
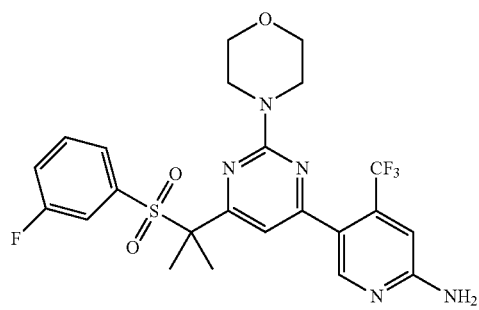
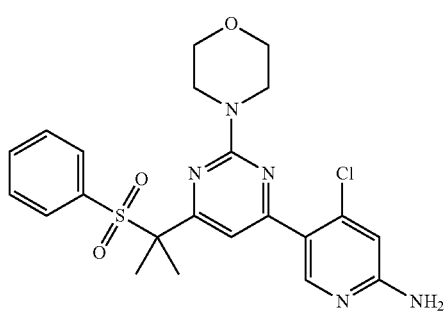
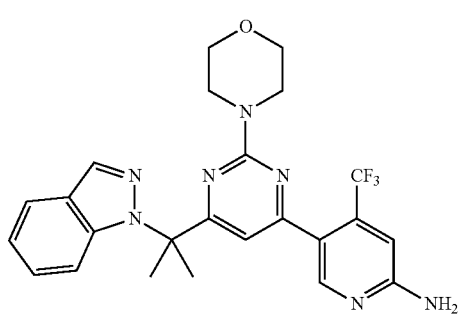
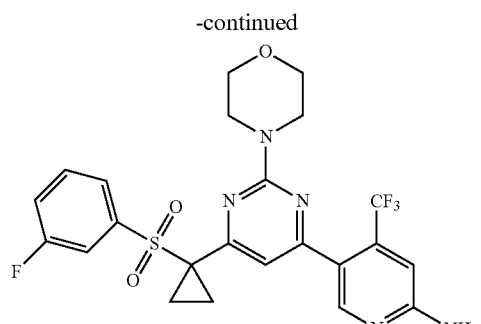
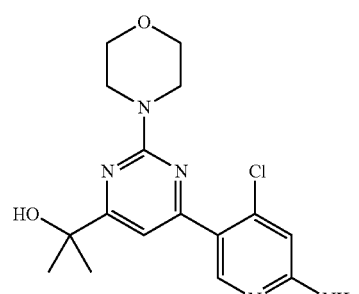
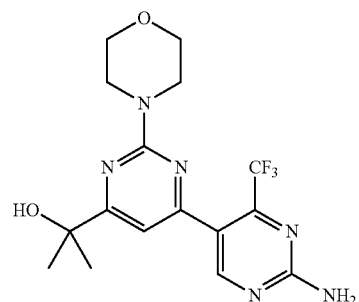
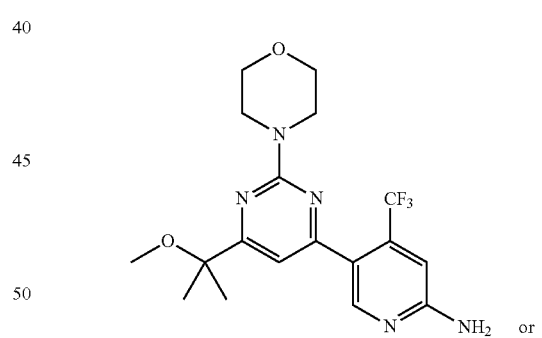
or
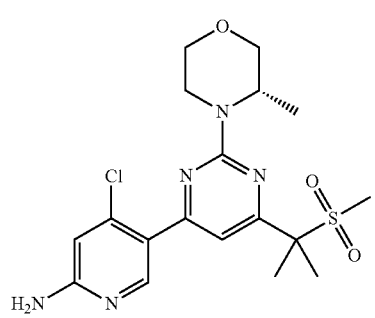

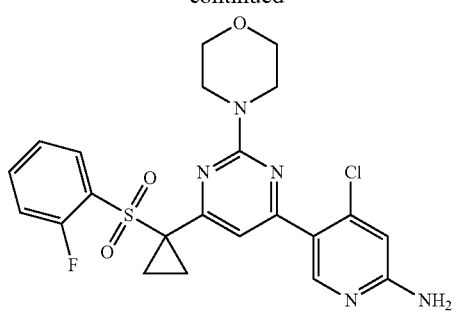
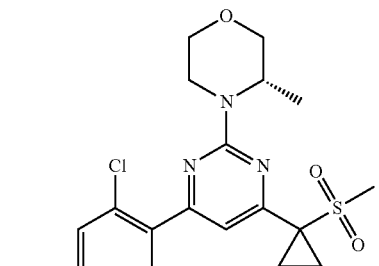
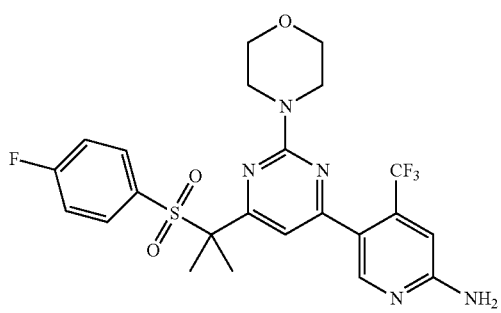
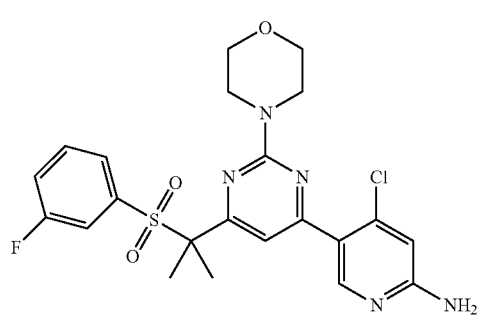
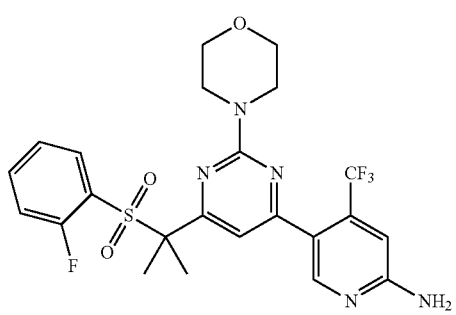
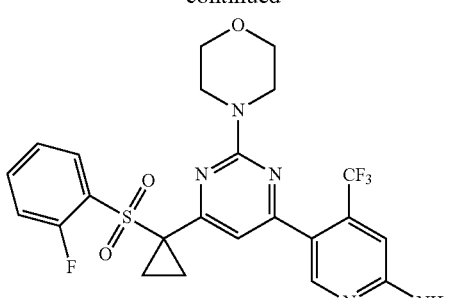
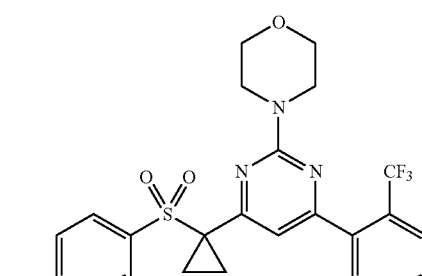
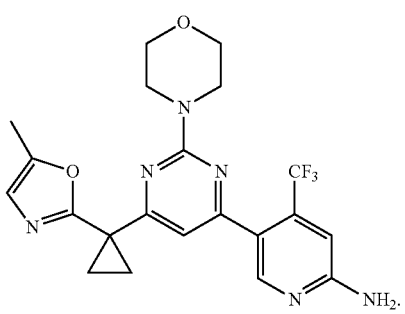 or
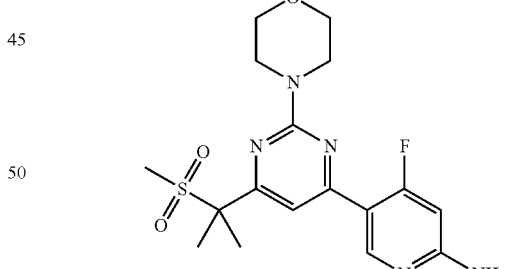
Preferably the compound of the present invention is selected from the group consisting of the following:
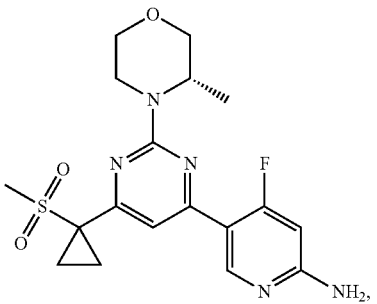

-continued

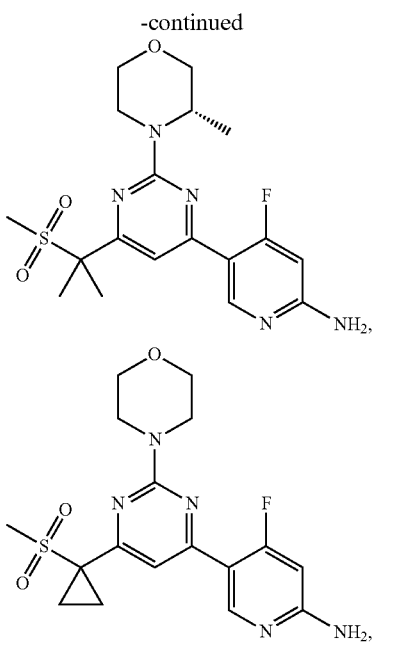

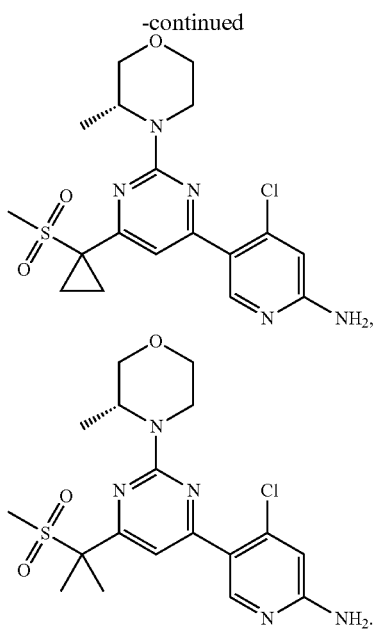

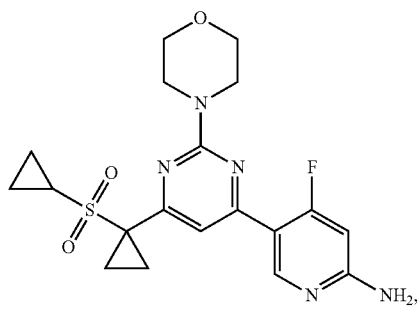

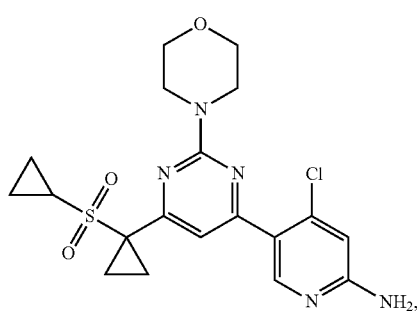

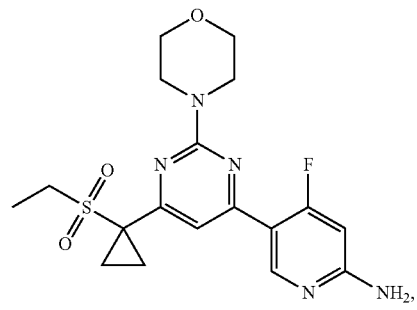

The second aspect of the present invention provides a pharmaceutical composition comprising the compound as described above, or a pharmaceutically acceptable salt, solvate, stereoisomer, or prodrug thereof; and a pharmaceutically acceptable carrier.

The third aspect of the present invention provides a use of the compound as described above, or a pharmaceutically acceptable salt, solvate, stereoisomer, or prodrug thereof or the pharmaceutical composition as described above, in the manufacture of a medicament for treating a protein tyrosine kinase-mediated disease.

Preferably, said protein tyrosine kinase-mediated disease is a PI3K kinase-mediated disease.

The fourth aspect of the present invention provides a use of the compound as described above, or a pharmaceutically acceptable salt, solvate, stereoisomer, or prodrug thereof, or the pharmaceutical composition as described above, in the manufacture of a medicament for inhibiting the PI3K kinase.

The fifth aspect of the present invention provides a use of the compound as described above, or a pharmaceutically acceptable salt, solvate, stereoisomer, or prodrug thereof, or the pharmaceutical composition as described above, in the manufacture of a medicament for treating cancer or a tissue proliferative disease.

Preferably, the cancer is selected from the group consisting of melanoma, papillary thyroid neoplasms, cholangiocarcinoma, colon cancer, ovarian cancer, endometrial cancer, cervical cancer, lung cancer, esophageal cancer, brain cancer, malignant lymphoma, liver cancer, stomach cancer, kidney cancer, bladder cancer, prostate cancer, breast cancer, pancreatic cancer or sarcoma, and primary or recurrent solid tumors of the skin, colon, thyroid, lung, and ovary, leukemia, head and neck cancer, glioma, glioblastoma.

The utilization of the compound of the present invention, or the pharmaceutically acceptable salt, solvate, stereoisomer or prodrug thereof, or the pharmaceutical composition and use thereof, has a significant PI3K kinase inhibitory activity, not only exhibiting high inhibitory activity on PI3K and especially PI3K-α kinase on enzyme level, but also exhibiting high inhibitory effect on PIK3CA mutant breast cancer cell lines T47D and MCF-7, while at the same time showing low cytotoxicity. Moreover, these compounds have relatively low cytotoxicity in normal cell lines (such as NIH-3T3 cells), thereby significantly reducing nonspecific side effects. They may be formulated with one or more pharmaceutically acceptable carriers in a suitable dosage form to be administered. These dosage forms are suitable for oral administration, rectal administration, topical administration, intraoral administration, and other parenteral (e.g., subcutaneous, intramuscular, intravenous, etc.) administration. For example, the dosage forms suitable for oral administration include capsules, tablets, granules, syrups and the like. The compounds of the present invention contained in these formulations may be solid powders or granules; solutions or suspensions in aqueous or non-aqueous liquids; water-in-oil or oil-in-water emulsions and the like. They have very practical values.

DETAILED DESCRIPTION OF THE INVENTION

In order to provide a clearer understanding of the technical contents of the present invention, the specific embodiments of the present invention will be further illustrated as follows.

"$C_{1-10}$ alkyl" refers to a straight or branched saturated aliphatic hydrocarbyl having from 1 to 10 carbon atoms, including but not limited to methyl, ethyl, propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, various branched isomers thereof and the like. Alkyl may be substituted or unsubstituted. When it is substituted, the substituent may be substituting at any possible attachment point, preferably one or more of the following groups, independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocycloalkylthio, oxo, amino, ¾ substituted alkyl, hydroxyalkyl, carboxyl and carboxylate.

"$C_{1-10}$ haloalkyl" means that $C_{1-10}$ alkyl is substituted with 1, 2 or 3 halogen atoms (preferably fluorine atom), preferably $C_{1-6}$ haloalkyl, more preferably $C_{1-3}$ haloalkyl, such as monochloroethyl, dichloromethyl, 1,2-dichloroethyl, monobromoethyl, monofluoroethyl, monofluoromethyl, difluoromethyl, trifluoromethyl and the like.

"$C_{3-10}$ cycloalkyl" refers to a cycloalkyl having 3 to 10 carbon atoms. Examples of cycloalkyl are cyclopropyl, cyclobutyl, cyclopentyl, cyclohexyl and the like.

"$C_{3-8}$ cycloalkoxy" refers to $C_{3-8}$ cycloalkyl-O—, such as cyclopropyloxy, cyclobutoxy, cyclopentyloxy, cyclohexyloxy and the like.

"$C_{1-10}$ alkoxy" refers to $C_{1-10}$ alkyl-O—, such as methoxy, ethoxy, propoxy, butoxy and the like.

"$C_{2-10}$ alkenyl" refers to a linear or branched unsaturated aliphatic hydrocarbyl having a carbon-carbon double bond (C=C) having 2 to 10 (preferably 2 to 6) carbon atoms, such as vinyl, propenyl, isopropenyl, n-butenyl, isobutenyl, pentenyl, hexenyl and the like.

"$C_{6-10}$ aryl" and "$C_{6-10}$ aromatic ring" are used interchangeably and refer to an aromatic hydrocarbyl having 6 to 10 carbon atoms, such as phenyl, naphthyl and the like.

"halogen" refers to fluoro, chloro, bromo or iodo.

"$C_{4-10}$ cycloalkenyl" refers to a partially unsaturated monocyclic carbon ring containing from 4 to 10 ring atoms, preferably $C_{4-8}$ cycloalkenyl, for example, including, but not limited to, cyclopentenyl, 1,3-cyclohexadienyl, 1,4-cyclohexadienyl, cyclohexenyl, cycloheptenyl and the like.

"Heteroaromatic ring" and "heteroaryl" are used interchangeably and refer to a radical that has 5-10 ring atoms, preferably 5, 6, 9 or 10 ring atoms, shares 6, 10 or 14 π electrons in the ring array, and has 1 to 5 heteroatoms in addition to carbon atoms. The term "heteroatom" refers to nitrogen, oxygen or sulfur.

"Partially unsaturated" refers to a t-electron system that contains one or more unsaturated bonds but is not fully conjugated.

"5- to 6-membered monocyclic heteroaryl ring" refers to a monocyclic heteroaryl ring containing 5 to 6 ring atoms, including, but not limited to, thiophene rings, furan rings, thiazole rings, imidazole rings, oxazole ring, pyrrole ring, pyrazole ring, triazole ring, tetrazole ring, isoxazole ring, oxadiazole ring, thiadiazole ring, pyridine ring, pyridazine ring, pyrimidine ring, pyrazine ring and the like.

"8- to 10-membered bicyclic heteroaryl ring" refers to a bicyclic heteroaryl ring containing from 8 to 10 ring atoms, including but not limited to, benzofuran ring, benzothiophene ring, indole ring, isoindole ring, quinoline ring, isoquinoline ring, indazole ring, benzothiazole ring, benzimidazole ring, quinazoline ring, quinoxaline ring, cinnoline ring, and phthalazine ring.

"3- to 10-membered saturated or partially unsaturated mono-heterocyclic ring" means that 1, 2 or 3 carbon atoms are replaced by nitrogen, oxygen or sulfur atoms in the mono-heterocyclic ring.

"3- to 10-membered saturated or partially unsaturated monocyclic ring" refers to saturated monocyclic carbon ring or partially unsaturated monocyclic carbon ring containing 3-10 ring atoms, such as (but not limited to) cyclopropyl ring, cyclobutyl ring, cyclopentyl ring, cyclohexyl ring, cyclohexadienyl ring, cycloheptyl ring, cycloheptatrienyl ring and the like.

Pharmaceutical Compositions

The phrase "the active substance of the present invention" or "the active compound of the present invention" refers to the compound of formula (I) of the present invention, or a pharmaceutically acceptable salt, solvate, stereoisomer, or prodrug thereof, which has significant PI3K kinase inhibitory activity, and which not only has high inhibitory activity on PI3K, especially PI3K-α kinase, on enzyme level, but also has high inhibitory effect on PIK3CA mutant breast cancer cell lines T47D and MCF-7, while at the same time has low cytotoxicity.

Said "pharmaceutically acceptable salt" includes a pharmaceutically acceptable acid addition salt and a pharmaceutically acceptable base addition salt.

"Pharmaceutically acceptable acid addition salt" refers to a salt formed with an inorganic acid or an organic acid that is capable of retaining the bioavailability of the free base without any other side effects. Inorganic acid salt includes, but is not limited to, hydrochloride, hydrobromide, sulfate, phosphate and the like; and organic acid salt includes, but is not limited to, formate, acetate, propionate, glycolate, gluconate, lactate, oxalate, maleate, succinate, fumarate, tartrate, citrate, glutamate, aspartate, benzoate, methanesulfonate, p-toluenesulfonate, salicylate and the like. These salts can be prepared by the methods known in the art.

"Pharmaceutically acceptable base addition salt" includes, but is not limited to, salt of an inorganic base such as sodium, potassium, calcium and magnesium salts and the like, and includes, but is not limited to, salt of an organic base such as ammonium salt, triethylamine salt, lysine salt, arginine salt and the like. These salts can be prepared by the methods known in the art.

The compounds of formula (I) may be present in one or more crystalline forms, and the active compounds of the present invention include various crystalline forms and mixtures thereof.

"Solvate" mentioned in the present invention refers to a complex formed by the compound of the present invention with a solvent. They either react in a solvent or precipitate or crystallize out of the solvent. For example, a complex formed with water is called a "hydrate". Solvates of the compounds of formula (I) are within the scope of this invention.

The compounds represented by formula (I) of the present invention may contain one or more chiral centers and exist in different optically active forms. When the compound contains one chiral center, the compound comprises an enantiomer. The present invention includes both isomers and mixtures thereof, such as racemic mixtures. Enantiomers can be resolved by methods known in the art, such as crystallization, chiral chromatography and the like. When the compound of formula (I) contains more than one chiral centers, diastereomers may be present. The present invention includes specific optically pure isomers which have been resolved, as well as mixtures of diastereomers. Diastereomers can be resolved by methods known in the art, such as crystallization and preparative chromatography.

The present invention includes prodrugs of the abovementioned compounds. Prodrugs include known aminoprotecting group and carboxy-protecting group, which are released to yield the parent compound via hydrolyzation or enzymatic reactions under physiological conditions. For specific preparation methods of prodrug, one can refer to Saulnier, M. G.; Frennesson, D. B.; Deshpande, M. S.; Hansel, S. B and Vysa, D. M. Bioorg. Med. Chem Lett. 1994, 4, 1985-1990; and Greenwald, R. B.; Choe, Y. H.; Conover, C. D.; Shum, K.; Wu, D.; Royzen, M. J. Med. Chem. 2000, 43, 475.

In general, the compound of the present invention or pharmaceutically acceptable salt, solvate, stereoisomer, or prodrug thereof may be administered in a suitable dosage form with one or more pharmaceutically acceptable carriers. These dosage forms are suitable for oral administration, rectal administration, topical administration, intraoral administration, and other parenteral (e.g., subcutaneous, intramuscular, intravenous, etc.) administration. For example, dosage forms suitable for oral administration include capsules, tablets, granules, syrups and the like. The compound of the present invention contained in these formulations may be solid powders or granules; solutions or suspensions in aqueous or non-aqueous liquids; water-in-oil or oil-in-water emulsions and the like. The above dosage forms may be made from the active compound and one or more carriers or excipients via a general pharmaceutical method. The aforementioned carrier needs to be compatible with the active compound or other excipients. For solid preparations, non-toxic carriers commonly used include, but are not limited to, mannitol, lactose, starch, magnesium stearate, cellulose, glucose, sucrose and the like. Carriers for liquid preparations include water, physiological saline, aqueous dextrose solution, ethylene glycol, polyethylene glycol and the like. The active compound may form a solution or a suspension with the above carrier.

The compositions of the present invention are formulated, quantified and administered in a manner consistent with medical practice. The "therapeutically effective amount" of the compound to be administered is determined by factors such as the particular condition to be treated, the subject being treated, the cause of the disorder, the target of the drug, the mode of administration and the like.

The phrase "therapeutically effective amount" refers to an amount that can be functional or active to humans and/or animals and also can be accepted by humans and/or animals.

The therapeutically effective amount of the compound of the present invention or the pharmaceutically acceptable salt, solvate, stereoisomer, or prodrug thereof contained in the pharmaceutical composition or medicinal composition of the present invention is preferably from 0.1 mg to 5 g/kg (body weight).

Preparation Methods

The experimental methods which do not specify specific conditions in the following examples are generally carried out according to conventional conditions such as those described in Sambrook et al., Molecular Cloning: Laboratory Manual (New York: Cold Spring Harbor Laboratory Press, 1989), or conditions as recommended by the manufacturers. Unless otherwise indicated, percentages and parts are by weight.

Unless otherwise defined, terms used herein are of the same meanings that are familiar to those skilled in the art. In addition, any methods and materials similar with or equivalent to those described herein can be applied to the present invention.

Reagents and Instruments

$^1$HNMR: Bruker AVANCE-400 NMR instrument, internal standard is tetramethylsilane (TMS).

LC-MS: Agilent 1200 HPLC System/6140 MS spectrometer (manufacturer: Agilent), WatersX-Bridge column, 150× 4.6 mm, 3.5 μm.

Preparative high performance liquid chromatography (pre-HPLC): Waters PHW007, XBridge C18 column, 4.6*150 mm, 3.5 μm.

ISCO Combiflash-Rf75 or Rf200 automatic column instrument as well as Agela 4 g, 12 g, 20 g, 40 g, 80 g, and 120 g disposable silica gel column were used.

Known starting materials may be synthesized using methods known in the art, or can be purchased from ABCR GmbH & Co. KG, Acros Organics, Aldrich Chemical Company, Accela ChemBio Inc, Darryl Chemicals and so on.

Unless otherwise specified, the reactions in the examples were carried out in a nitrogen or argon atmosphere.

Unless otherwise stated, the solutions in the examples were aqueous solutions.

DMF: dimethylformamide, DMSO: dimethylsulfoxide, THF: tetrahydrofuran, DIEA: N,N-diisopropylethylamine, EA: ethyl acetate, PE: petroleum ether, BINAP: (2R,3S)-2, 2'-bis-diphenylphosphino-1,1'-binaphthalene. NBS (N-bromosuccinimide), NCS (N-chlorosuccinimide), $Pd_2(dba)_3$ (tris (dibenzylideneacetone) dipalladium), $Pd(dppf)Cl_2$ ([1, 1'-bis (diphenylphosphino) ferrocene] dichloropalladium).

As used herein, room temperature refers to about 20-30° C.

Preparation Method of Compound 1a

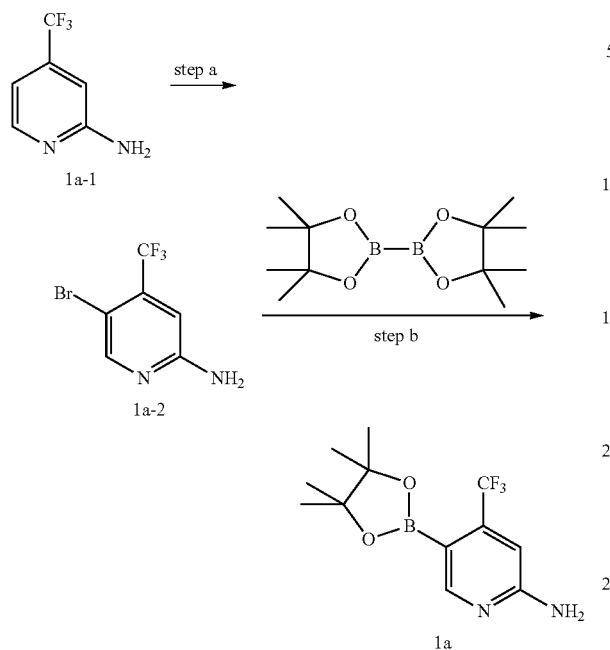

Step a: N-bromosuccinimide (6.0 g, 34 mmol) was added to a solution of 1a-1 (5.0 g, 30 mmol) in trichloromethane (100 ml) and the mixture was stirred at room temperature for 2 hours. The reaction was complete and the mixture was concentrated under reduced pressure and extracted with dichloromethane. The organic phase was separated and concentrated under reduced pressure to give crude product which was purified by Combi-flash column chromatography to obtain compound 1a-2 (6.0 g). Purity: 80%, spectrum data: MS m/z(ESI): 241[M+H]+.

Step b: Compound 1a-2 (3.0 g, 12.5 mmol), bis(pinacol) diboron (3.49 g, 13.75 mmol), potassium acetate (3.68 g, 37.5 mmol) and Pd(dppt)Cl$_2$ (50 mg, 0.625 mmol) were added to the solution of 1,4-dioxane (50 ml) and the mixture was stirred at 115° C. overnight. The reaction was complete and the mixture was cooled to room temperature, filtered, extracted with water and ethyl acetate. The organic phase was separated and concentrated under reduced pressure to give the crude product which was purified by Combi-flash column chromatography to give compound 1a (1.5 g). Purity: 80%, spectrum data: MS m/z(ESI): 289[M+H]+.

Preparation Method of Compound 2a

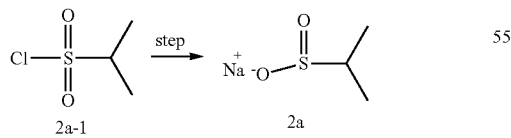

Step: Compound 2a-1 (500 mg, 3.5 mmol) was added to sodium sulphite (485 mg, 3.85 mmol) in 7 ml of water at room temperature and heated to 50° C. A saturated aqueous solution of sodium bicarbonate was added dropwise to adjust the pH to 8 and the mixture was stirred at 50° C. for 4 hours. The reaction was completed and the mixture was cooled to room temperature, concentrated under reduced pressure, dissolved in ethanol and filtered. The filtrate was concentrated under reduced pressure to give crude product 2a (400 mg) which was used directly in the next reaction.

Preparation Method of Compound 3a

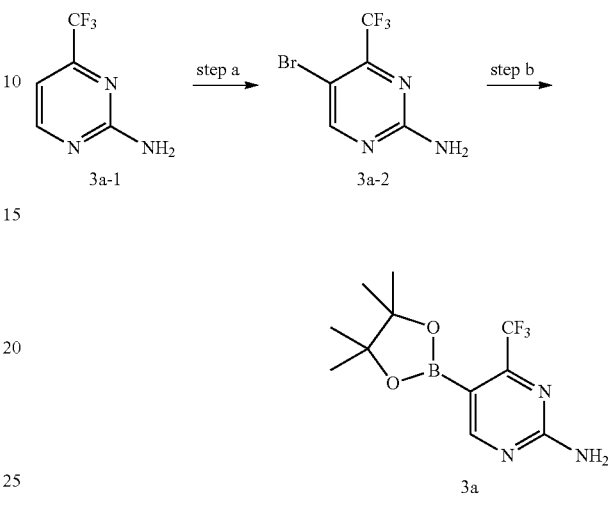

Step a: Compound 3a-2 (600 mg) was obtained in a manner similar to the preparation method of step a in compound 1a using compound 3a-1 (500 mg) as the starting material, and the purity was 82%.

Step b: Compound 3a (320 mg) was obtained in a manner similar to the preparation method of step b in compound 1a using compound 3a-2 (600 mg) as the starting material. Purity: 74%, yield: 40%, spectrum data: MS m/z(ESI): 290[M+H]+.

Preparation Method of Compound 4a

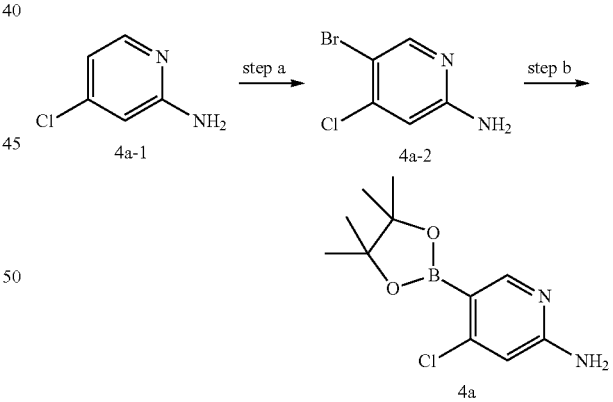

Step a: Compound 4a-2 (1.2 g) as a yellow solid was obtained in a manner similar to the preparation method of step a in compound 1a using compound 4a-1 (1.0 g) as the starting material. Purity: 84%, spectrum data: MS m/z(ESI): 207[M+H]+.

Step b: Compound 4a (100 mg) as a yellow solid was obtained in a manner similar to the preparation method of step b in compound 1a using compound 4a-2 (1.2 g) as the starting material. Purity: 82%, yield: 5%, spectrum data: MS m/z(ESI): 255[M+H]+.

Preparation Method of Compound 5a

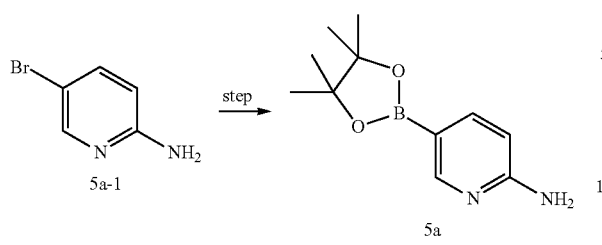

Step: Compound 5a (800 mg) was obtained in a manner similar to the preparation method of step b in compound 1a using compound 5a-1 (500 mg) as the starting material. Spectrum data: MS m/z(ESI): 221 [M+H]+.

Preparation Method of Compound 6a

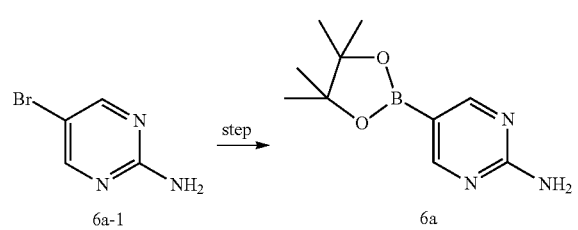 [SMILES: Nc1ncc(Br)cn1 ; CC1(C)OB(c2cnc(N)nc2)OC1(C)C]

Step: Compound 6a (800 mg) was obtained in a manner similar to the preparation method of step b in compound 1a using compound 6a-1 (500 mg) as the starting material. Purity: 37%, spectrum data: MS nm/z(ESI): 222[M+H]+.

Preparation Method of Compound 7a

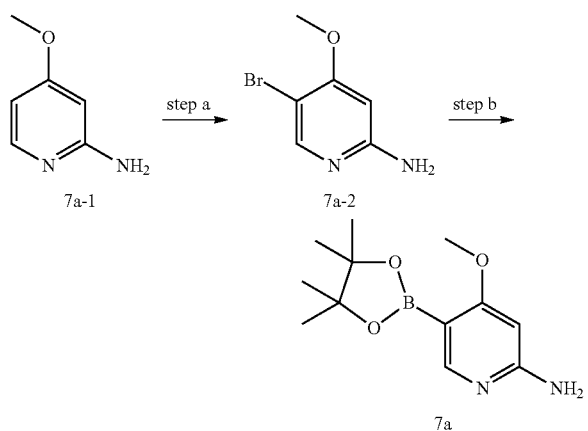

Step a: A solution of compound 7a-1 (500 mg, 4 mmol) in 10 ml of acetic acid was added to a solution of bromine (4 ml, 1 M in acetic acid) and stirred at room temperature for 1 hour. The reaction was complete and the mixture was filtered and extracted with ethyl acetate and saturated sodium bicarbonate. The organic phase was dried over anhydrous sodium sulfate, separated and concentrated under reduced pressure to give the crude product which was purified by Combi-flash column chromatography to give the compound 7a-2 (340 mg). Purity: 78%, yield: 41%. spectrum data: MS m/z(ESI): 203[M+H]+.

Step b: Compound 7a was obtained in a manner similar to the preparation method of step b in compound 1a using compound 7a-2(390 mg) as the starting material, and directly used in the next step. Spectrum data: MS m/z(ESI): 251[M+H]+.

Preparation Method of Compound 8a

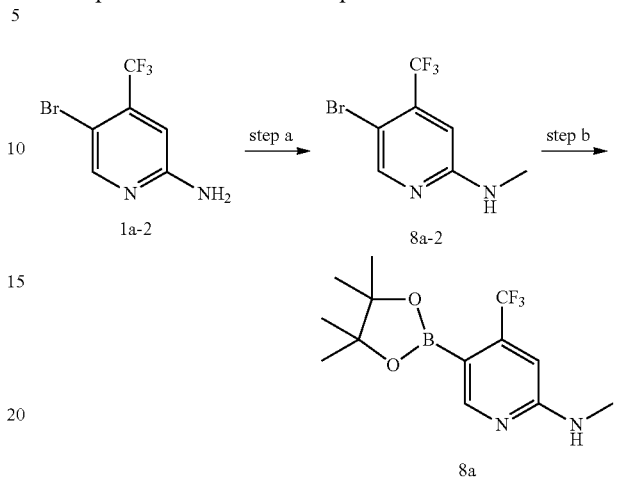

Step a: Compound 1a-2 (1.5 g, 6.28 mmol), formaldehyde (1.13 g, 37.66 mmol) and sodium methoxide (3.39 g, 62.8 mmol) were added to 25 ml of methanol and stirred at 65° C. for 4 hours. The mixture was cooled to room temperature and sodium borohydride (1.43 g, 37.68 mmol) was added and stirred at 70° C. for 2 hours. The reaction was completed and the mixture was cooled to room temperature, concentrated under reduced pressure, and extracted with saturated brine and ethyl acetate. The organic phase was separated and concentrated under reduced pressure to give compound 8a-2 (1.2 g). Spectrum data: MS m/z(ESI): 255[M+H]+.

Step b: Compound 8a (500 mg) was obtained in a manner similar to the preparation method of step b in compound 1a using compound 8a-2 (650 mg) as the starting material. Spectrum data: MS m/z(ESI): 303[M+H]+.

Preparation Method of Compound 9a

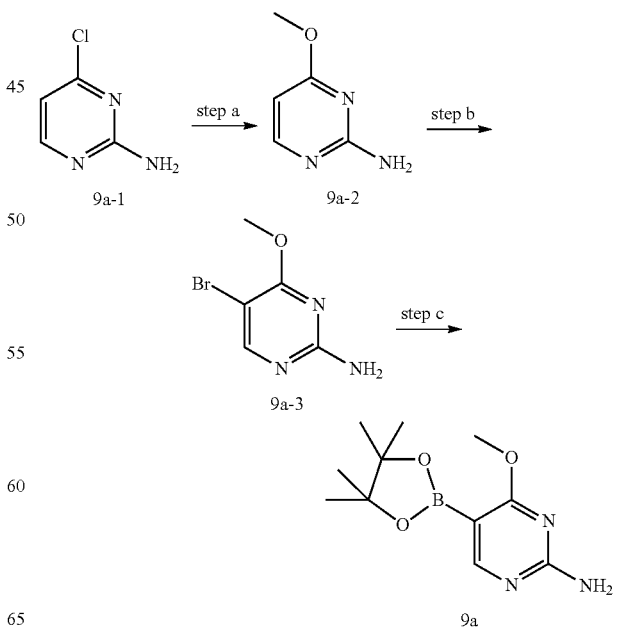

Step a: Sodium methoxide (0.83 g, 15.2 mmol) was added to the solution of compound 9a-1 (1.0 g, 7.6 mmol) in 30 ml of methanol and the mixture was stirred at 80° C. for 2 hours. The reaction was complete and the mixture was cooled to room temperature, concentrated under reduced pressure and purified by Combi-flash column chromatography to give compound 9a-2 (630 mg). Purity: 84%, spectrum data: MS m/z(ESI): 126[M+H]+.

Step b: Compound 9a-3 (630 mg) was obtained in a manner similar to the preparation method of step a in compound 1a using compound 9a-2 (500 mg) as the starting material.

Step c: Compound 9a (351 mg) was obtained in a manner similar to the preparation method of step b in compound 1a using compound 9a-3 (300 mg) as the starting material. Spectrum data: MS m/z(ESI): 170[M−81]+.

Preparation Method of Compound 10a

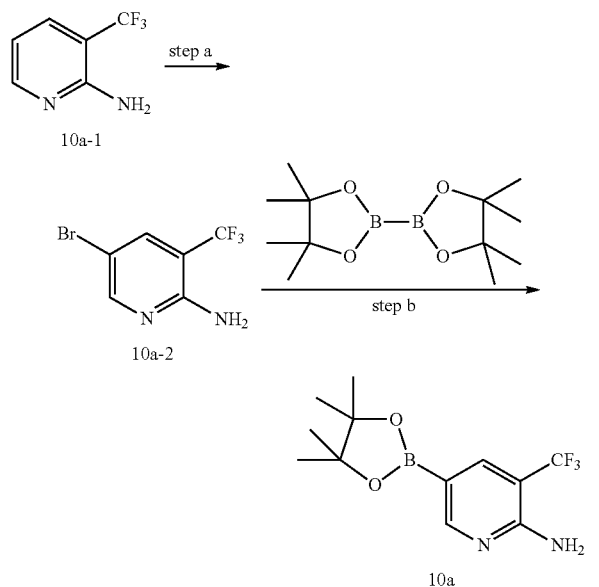

Step a: Compound 10a-2 (2.97 g) was obtained in a manner similar to the preparation method of step a in compound 1a using compound 10a-1 (2 g) as the starting material. Purity: 95%, spectrum data: MS m/z(ESI): 241 [M+H]+.

Step b: Compound 10a (3.6 g) was obtained in a manner similar to the preparation method of step b in compound 1a using compound 10a-2 (2.97 g) as the starting material. Purity: 32%, spectrum data: MS m/z(ESI): 289[M+H]+.

Preparation Method of Compound 11a

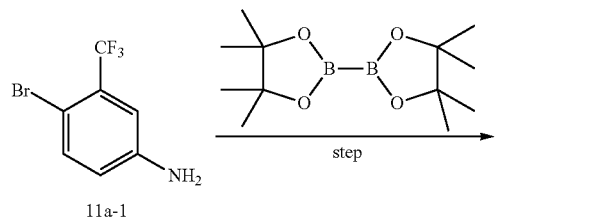

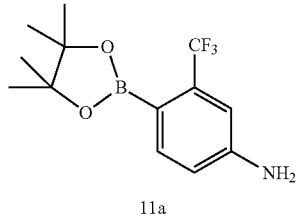

Step: Compound 11a (900 mg) was obtained in a manner to the preparation method of step b in compound 1a using compound 11a-1 (1 g) as the starting material. Purity: 55%, spectrum data: MS m/z(ESI): 288[M+H]+.

Example 1 The preparation of 5-(6-(1-(methylsulfonyl)cyclopropyl)-2-morpholinopyrimidin-4-yl)-4-(trifluoromethyl)pyridin-2-amine (S-1)

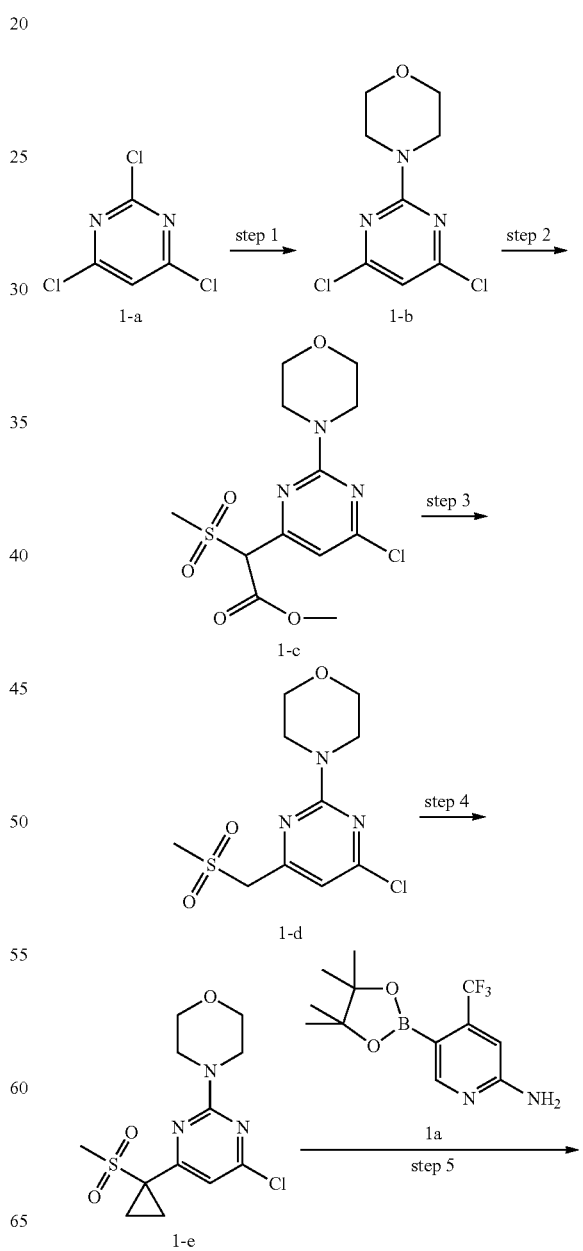

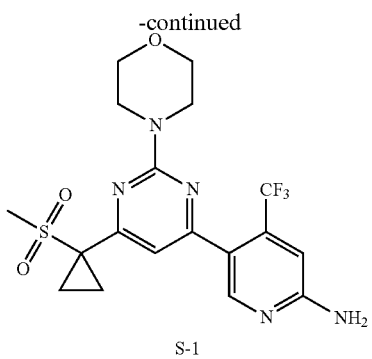

S-1

Step 1: 4-(4,6-dichloropyrimidin-2-yl)morpholine

The solution of compound 1-a (5.0 g, 27.5 mmol) and triethylamine (3.0 g, 30 mmol) in 25 ml of dichloromethane was added dropwise to a solution of morpholine (2.4 g, 27.5 mmol) in 5 ml of dichloromethane at 5 to 15° C. and stirred at room temperature for 2 hours. The reaction was completed and the mixture was extracted with dichloromethane. The combined organic phases were separated and concentrated under reduced pressure to give the crude product which was purified by Combi-flash column chromatography to give compound 1-b (1.4 g). Purity: 95%. Spectrum data: MS m/z(ESI): 234[M+H]+.

Step 2: Methyl 2-(6-chloro-2-morpholin-4-yl)-2-(methylsulfonyl) acetate

A mixture of compound 1-b (1.4 g, 6 mmol), methyl 2-(methylsulfonyl) acetate (1.0 g, 6.6 mmol), sodium hydride (500 mg, 12 mmol) and dimethylsulfoxide (30 mL) was added to a sealed tube and stirred at 120° C. under microwave for 15 minutes. The reaction was completed, the mixture was cooled to room temperature and extracted with ethyl acetate. The combined organic phase was separated and concentrated under reduced pressure to give crude product which was purified by Combi-flash column chromatography to give compound 1-c (500 mg). Purity: 95%. Spectrum data: MS m/z(ESI): 350[M+H]+.

Step 3: 4-(4-chloro-6-(methylsulfonylmethyl)pyrimidin-2-yl)morpholine

Compound 1-c (500 mg, 1.4 mmol) and sodium hydroxide (170 mg, 4.3 mmol) were added to methanol/water (10 ml/2.5 ml) and stirred at 60° C. for 1 hour. The reaction was completed. The mixture was cooled to room temperature, extracted with ethyl acetate, washed with water and the organic phase was separated and concentrated under reduced pressure to give crude compound 1-d (500 mg). Purity: 10%, spectrum data: MS m/z(ESI): 292[M+H]+.

Step 4: 4-(4-chloro-6-(1-(methylsulfonyl)cyclopropyl)pyrimidin-2-yl)morpholine 1,2-dibromoethane (1.3 g, 7 mmol) and sodium hydride (300 mg, 7 mmol) were added to the solution of compound 1-d (500 mg, 1.7 mmol) in 15 ml of dimethylformamide and stirred at room temperature for 1 hour. The reaction was completed, and the reaction mixture was extracted with water and ethyl acetate. The combined organic phase was separated, dried over anhydrous sodium sulfate and filtered. The filtrate was concentrated under reduced pressure to give crude compound 1-e (48 mg). Purity: 12%, spectrum data: MS m/z(ESI): 318[M+H]+.

Step 5: 5-(6-(1-(methylsulfonyl)cyclopropyl)-2-morpholinopyrimidin-4-yl)-4-(trifluoromethyl)pyridin-2-amine Compound 1-e (450 mg, 0.17 mmol), compound 1a (65 mg, 0.17 mmol), Pd(dppf)Cl$_2$ ([1,1'-bis(diphenylphosphino)ferrocene]dichloropalladium (15 rag, 0.02 mmol), sodium carbonate (50 mg, 0.4 mmol) and acetonitrile/water (5 ml/1 ml) were added to a sealed tube and stirred at 120° C. under micromave for 10 minutes. The reaction was completed and the mixture was cooled to room temperature, filtered and the filtrate was concentrated under reduced pressure to give crude product which was purified by Combi-flash column chromatography to give compound S-1 (75 mg). Purity: 35%. Spectrum data: MS m/z(ESI): 444[M+H]+. $^1$H NMR (400 MHz, CDCl$_3$) δ 8.29 (s, 1H), 7.09 (s, 1H), 6.80 (s, 1H), 4.90 (brs, 2H), 3.89-3.80 (m, 4H), 3.79-3.73 (m, 4H), 3.07 (s, 3H), 1.86 (q, J=4.5 Hz, 2H), 1.57 (q, J=4.8 Hz, 2H).

Example 2-19

Compounds S-4, S-10, S-12, S-16, and S-17 were prepared by referring to the method in Example 1 and using compound 1-a as the starting material except that 1,2-dibromoethane in step 4 was replaced by 1,3-dibromopropane, 1,4-dibromobutane, 1,5-dibromopentane, methyl iodide, and 2-iodopropane, respectively.

Compounds S-5 and S-6 were prepared by referring to the method in Example 1 and using compound 1-a as the starting material except that morpholine in step 1 was replaced by (R)-3-methylmorpholine and (S)-3-methylmorpholine.

Compound S-9 was prepared by referring to the method in Example 1 and using compound 1-a as the starting material except that morpholine in step 1 was replaced by (S)-3-methylmorpholine and 1,2-dibromoethane in step 4 was replaced by 1,3-dibromopropane.

Compounds S-30, S-31, S-32, S-33, S-34, and S-43 were prepared by referring to the method in Example 1 and using compound 1-a as the starting material except that morpholine in step 1 was replaced by (S)-3-methylmorpholine, 1,2-dibromoethane in step 4 was replaced by 1,3-dibromopropane and compound 1a in step 5 was replaced by compound 3a, 4a, 5a, 6a, 7a, and 9a, respectively.

Compounds S-36 and S-40 were prepared by referring to the method in Example 1 and using compound 1-a as the starting material except that compound 1a in step 5 was replaced by compound 8a, and 5a, respectively.

Compound S-39 was prepared by referring to the method in Example 1 and using compound 1-a as the starting material except that 1,2-dibromoethane in step 4 was replaced by methyl iodide and compound 1a in step 5 was replaced by 5a.

Compound S-42 was prepared by referring to the method in Example 1 and using compound 1-a as the starting material except that morpholine in step 1 was replaced by (S)-3-methylmorpholine and 1,2-dibromoethane in step 4 was replaced by 1,4-dibromobutane.

| No. | Structure | MS [M + H]+ | ¹HNMR |
|---|---|---|---|
| Example 2 | s-4 | 458 | ¹H NMR (400 MHz, CDCl₃) δ 8.31 (s, 1H), 6.90 (s, 1H), 6.81 (s, 1H), 4.88 (brs, 2H), 3.90-3.82 (m, 4H), 3.81-3.73 (m, 4H), 3.13-2.99 (m, 2H), 2.86-2.75 (m, 2H), 2.71 (s, 3H), 2.32-2.17 (m, 1H), 2.07-1.93 (m, 1H). |
| Example 3 | s-5 | 458 | ¹H NMR (400 MHz, CDCl₃) δ 8.30 (s, 1H), 7.07 (s, 1H), 6.80 (s, 1H), 4.89 (brs, 2H), 4.81-4.64 (m, 1H), 4.36 (dd, J = 13.6, 2.2 Hz, 1H), 3.98 (dd, J = 11.4, 3.5 Hz, 1H), 3.77 (d, J = 11.4 Hz, 1H), 3.70 (dd, J = 11.4, 3.0 Hz, 1H), 3.55 (td, J = 12.0, 3.0 Hz, 1H), 3.27 (td, J = 13.1, 3.8 Hz, 1H), 3.08 (s, 3H), 1.92-1.80 (m, 2H), 1.60-1.54 (m, 2H), 1.30 (d, J = 6.8 Hz, 3H). |
| Example 4 | s-6 | 458 | ¹H NMR (400 MHz, CDCl₃) δ 8.30 (s, 1H), 7.07 (s, 1H), 6.80 (s, 1H), 4.87 (brs, 2H), 4.75-4.67 (m, 1H), 4.36 (dd, J = 13.9, 2.6 Hz, 1H), 3.98 (dd, J = 11.2, 3.5 Hz, 1H), 3.77 (d, J = 11.3 Hz, 1H), 3.70 (dd, J = 11.4, 3.1 Hz, 1H), 3.55 (td, J = 11.9, 3.0 Hz, 1H), 3.28 (td, J = 12.8, 3.6 Hz, 1H), 3.08 (s, 3H), 1.90-1.85 (m, 2H), 1.57 (overlap, 2H), 1.30 (d, J = 6.8 Hz, 3H). |
| Example 5 | s-9 | 472 | ¹H NMR (400 MHz, CDCl₃) δ 8.31 (s, 1H), 6.88 (s, 1H), 6.80 (s, 1H), 4.88 (brs, 2H), 4.78-4.70 (m, 1H), 4.39 (dd, J = 13.6, 2.5 Hz, 1H), 3.99 (dd, J = 11.3, 3.6 Hz, 1H), 3.78 (d, J = 11.4 Hz, 1H), 3.71 (dd, J = 11.5, 3.1 Hz, 1H), 3.56 (td, J = 11.9, 3.0 Hz, 1H), 3.28 (td, J = 12.4, 3.6 Hz, 1H), 3.12-2.99 (m, 2H), 2.88-2.73 (m, 2H), 2.71 (s, 3H), 2.33-2.18 (m, 1H), 2.06-1.93 (m, 1H), 1.30 (d, J = 6.8 Hz, 3H). |

-continued
| No. | Structure | MS [M + H]+ | ¹HNMR |
|---|---|---|---|
| Example 6 | 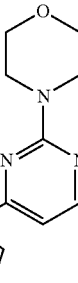<br>s-10 | 472 | ¹H NMR (400 MHz, CDCl₃) δ 8.31 (s, 1H), 7.04 (s, 1H), 6.80 (s, 1H), 4.88 (brs, 2H), 3.89-3.81 (m, 4H), 3.81-3.73 (m, 4H), 2.75 (s, 3H), 2.71-2.63 (m, 2H), 2.61-2.50 (m, 2H), 1.98-1.88 (m, 2H), 1.72-1.62 (m, 2H). |
| Example 7 | 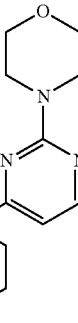<br>s-12 | 486 | ¹H NMR (400 MHz, CDCl₃) δ 8.32 (s, 1H), 7.02 (s, 1H), 6.80 (s, 1H), 4.89 (brs, 2H), 3.86-3.81 (m, 4H), 3.81-3.75 (m, 4H), 2.78-2.71 (m, 2H), 2.70 (s, 3H), 2.15-2.06 (m, 2H), 1.88-1.76 (m, 2H), 1.38-1.21 (m, 4H). |
| Example 8 | 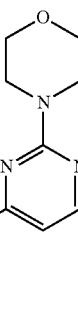<br>s-16 | 446 | ¹H NMR (400 MHz, CDCl₃) δ 8.31 (s, 1H), 7.00 (s, 1H), 6.80 (s, 1H), 4.87 (brs, 2H), 3.93-3.81 (m, 4H), 3.81-3.70 (m, 4H), 2.85 (s, 3H), 1.83 (s, 6H). |
| Example 9 | 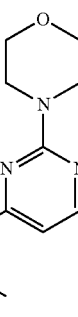<br>s-17 | 460 | ¹H NMR (400 MHz, CDCl₃) δ 8.30 (s, 1H), 6.82 (s, 1H), 6.80 (s, 1H), 4.88 (brs, 2H), 3.87-3.73 (m, 8H), 2.85 (s, 3H), 2.81-2.64 (m, 1H), 1.32 (d, J = 6.7 Hz, 3H), 0.95 (d, J = 6.7 Hz, 3H). |

| No. | Structure | MS [M + H]+ | ¹HNMR |
|---|---|---|---|
| Example 10 | s-30 | 473 | ¹H NMR (400 MHz, CDCl₃) δ 8.61 (s, 1H), 6.87 (s, 1H), 5.53 (brs, 2H), 4.78-4.68 (m, 1H), 4.39 (dd, J = 13.6, 2.4 Hz, 1H), 4.00 (dd, J = 11.4, 3.5 Hz, 1H), 3.79 (d, J = 11.4 Hz, 1H), 3.71 (dd, J = 11.5, 3.1 Hz, 1H), 3.56 (td, J = 12.0, 3.0 Hz, 1H), 3.29 (td, J = 13.0, 3.8 Hz, 1H), 3.13-2.99 (m, 2H), 2.88-2.73 (m, 2H), 2.71 (s, 3H), 2.35-2.19 (m, 1H), 2.08-1.93 (m, 1H), 1.30 (d, J = 6.8 Hz, 3H). |
| Example 11 | s-31 | 438 | ¹H NMR (400 MHz, CDCl₃) δ 8.42 (s, 1H), 7.12 (s, 1H), 6.58 (s, 1H), 4.80-4.74 (m, 1H), 4.72 (brs, 2H), 4.42 (dd, J = 13.6, 2.1 Hz, 1H), 4.00 (dd, J = 11.3, 3.3 Hz, 1H), 3.80 (d, J = 11.4 Hz, 1H), 3.72 (dd, J = 11.4, 3.1 Hz, 1H), 3.57 (td, J = 12.0, 3.0 Hz, 1H), 3.29 (td, J = 13.1, 3.8 Hz, 1H), 3.11-3.01 (m, 2H), 2.84-2.75 (m, 2H), 2.73 (s, 3H), 2.33-2.18 (m, 1H), 2.05-1.93 (m, 1H), 1.31 (d, J = 6.8 Hz, 3H). |
| Example 12 | s-32 | 404 | ¹H NMR (400 MHz, DMSO) δ 8.79 (d, J = 2.3 Hz, 1H), 8.15 (dd, J = 8.8, 2.4 Hz, 1H), 7.19 (s, 1H), 6.57 (brs, 2H), 6.52 (d, J = 8.8 Hz, 1H), 4.77-4.65 (m, 1H), 4.38 (d, J = 13.1 Hz, 1H), 3.94 (dd, J = 11.3, 3.2 Hz, 1H), 3.74 (d, J = 11.4 Hz, 1H), 3.62 (dd, J = 11.3, 2.9 Hz, 1H), 3.47 (td, J = 11.8, 2.7 Hz, 1H), 3.20 (td, J = 13.2, 3.7 Hz, 1H), 2.96-2.71 (m, 7H), 2.12-1.84 (m, 2H), 1.22 (d, J = 6.7 Hz, 3H). |
| Example 13 | s-33 | 405 | ¹H NMR (400 MHz, DMSO) δ 9.03 (s, 2H), 7.28 (s, 1H), 7.27 (brs, 2H), 4.76-4.66 (m, 1H), 4.38 (d, J = 12.6 Hz, 1H), 3.94 (dd, J = 11.3, 3.3 Hz, 1H), 3.74 (d, J = 11.4 Hz, 1H), 3.62 (dd, J = 11.5, 3.1 Hz, 1H), 3.47 (td, J = 11.9, 2.8 Hz, 1H), 3.20 (td, J = 13.1, 3.7 Hz, 1H), 2.94-2.65 (m, 7H), 2.11-1.99 (m, 1H), 1.96-1.84 (m, 1H), 1.22 (d, J = 6.7 Hz, 3H). |

| No. | Structure | MS [M + H]+ | ¹HNMR |
|---|---|---|---|
| Example 14 | s-34 | 434 | ¹H NMR (400 MHz, DMSO) δ 8.56 (s, 1H), 7.21 (s, 1H), 6.43 (brs, 2H), 6.09 (s, 1H), 4.72-4.61 (m, 1H), 4.32 (dd, J = 13.5, 1.8 Hz, 1H), 3.94 (dd, J = 11.1, 3.1 Hz, 1H), 3.83 (s, 3H), 3.73 (d, J = 11.3 Hz, 1H), 3.62 (dd, J = 11.4, 3.0 Hz, 1H), 3.46 (td, J = 11.9, 2.8 Hz, 1H), 3.17 (td, J = 13.1, 3.6 Hz, 1H), 2.97-2.81 (m, 5H), 2.77-2.63 (m, 2H), 2.11-2.00 (m, 1H), 1.96-1.83 (m, 1H), 1.21 (d, J = 6.7 Hz, 3H). |
| Example 15 | s-36 | 458 | ¹H NMR (500 MHz, CDCl₃) δ 8.34 (s, 1H), 7.09 (s, 1H), 6.67 (s, 1H), 4.97 (brs, 1H), 3.85-3.80 (m, 4H), 3.79-3.74 (m, 4H), 3.08 (s, 3H), 3.02 (d, J = 5.2 Hz, 3H), 1.79 (q, J = 4.6 Hz, 2H)1.61-1.56 (m, 2H). |
| Example 16 | s-39 | 378 | ¹H NMR (500 MHz, CDCl₃) δ 8.80 (d, J = 2.0 Hz, 1H), 8.10 (dd, J = 8.6, 2.3 Hz, 1H), 7.17 (s, 1H), 6.55 (d, J = 8.6 Hz, 1H), 4.73 (brs, 2H), 3.94-3.83 (m, 4H), 3.85-3.71 (m, 4H), 2.87 (s, 3H), 1.82 (s, 6H). |
| Example 17 | s-40 | 376 | ¹H NMR (500 MHz, CDCl₃) δ 8.80 (d, J = 2.1 Hz, 1H), 8.11 (dd, J = 8.7, 2.3 Hz, 1H), 7.27 (s, 1H), 6.55 (d, J = 8.7 Hz, 1H), 4.73 (brs, 2H), 3.90-3.83 (m, 4H), 3.83-3.76 (m, 4H), 3.06 (s, 3H), 1.84 (q, J = 4.6 Hz, 2H), 1.53 (q, J = 2.5 Hz, 2H). |

| No. | Structure | MS [M + H]+ | ¹HNMR |
|---|---|---|---|
| Example 18 | s-42 | 486 | ¹H NMR (400 MHz, CDCl₃) δ 8.33 (s, 1H), 7.03 (s, 1H), 6.80 (s, 1H), 4.88 (brs, 2H), 4.77-4.69 (m, 1H), 4.38 (dd, J = 13.7, 2.5 Hz, 1H), 3.99 (dd, J = 11.4, 3.6 Hz, 1H), 3.79 (d, J = 11.4 Hz, 1H), 3.72 (dd, J = 11.4, 3.1 Hz, 1H), 3.56 (td, J = 11.9, 3.0 Hz, 1H), 3.28 (td, J = 12.8, 4.0 Hz 1H), 2.74 (s, 3H), 2.72-2.53 (m, 4H), 1.98-1.88 (m, 2H), 1.71-1.64 (m, 2H), 1.30 (d, J = 6.8 Hz, 3H). |
| Example 19 | s-43 | 435 | ¹H NMR (400 MHz, CDCl₃) δ 8.97 (s, 1H), 7.37 (s, 1H), 5.14 (brs, 2H), 4.78-4.71 (m, 1H), 4.41 (dd, J = 13.1, 2.1 Hz, 1H), 4.03-3.98 (m, 4H), 3.80 (d, J = 11.3 Hz, 1H), 3.72 (dd, J = 11.3, 3.1 Hz, 1H), 3.57 (td, J = 12.1, 3.1 Hz, 1H), 3.28 (td, J = 12.0, 4.0 Hz, 1H), 3.10-3.01 (m, 2H), 2.81-2.77 (m, 2H), 2.72 (s, 3H), 2.27-2.20 (m, 1H), 1.99-1.94 (m, 1H), 1.29 (d, J = 6.8 Hz, 3H). |

Example 20 The preparation of 4-chloro-5-(6-(1-(methylsulfonyl)cyclopropyl)-2-morpholinopyrimidin-4-yl)pyridin-2-amine (S-37)

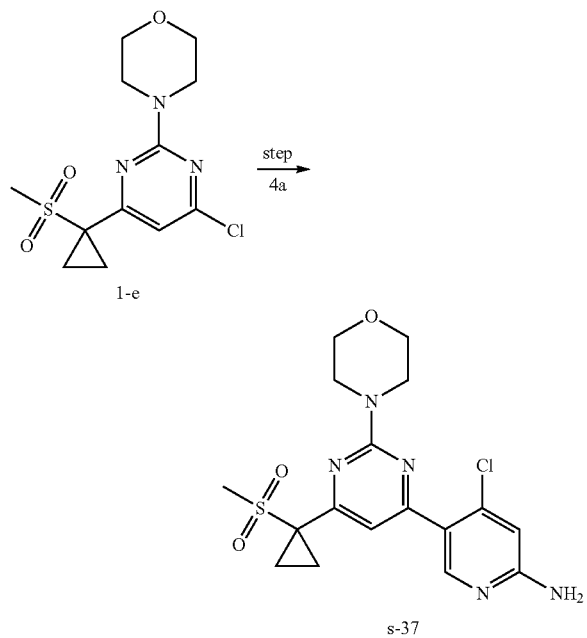

Step: 4-chloro-5-(6-(1-(methylsulfonyl)cyclopropyl)-2-morpholinopyrimidin-4-yl) pyridin-2-amine The mixture of compound 1-e (50 mg, 0.157 mmol), compound 4a (120 mg, 0.47 mmol), Pd(dppf)Cl₂ ([1,1'-bis(diphenylphosphino)ferrocene]dichloropalladium) (11.52 g, 0.016 mmol), sodium carbonate (24 mg, 0.314 mmol), and acetonitrile/water (5 ml/1 ml) was added to a sealed tube and stirred at 120° C. under microwave for 10 minutes. The reaction was completed and the mixture was cooled to room temperature, filtered, and extracted with water and ethyl acetate. The organic phase was separated and dried over sodium sulfate. The organic phase was separated and concentrated under reduced pressure to give the crude product which was separated and purified by preparative liquid chromatography to obtain compound S-37 (7.06 mg). Purity: 98.25%. Spectrum data: MS m/z(ESI): 410[M+H]+. ¹H NMR (500 MHz, CDCl₃) δ 8.40 (s, 1H), 7.31 (s, 1H), 6.58 (s, 1H), 4.69 (brs, 2H), 3.88-3.81 (m, 4H), 3.80-3.76 (m, 4H), 3.09 (s, 3H), 1.86 (q, J=4.5 Hz, 2H), 1.54-1.49 (m, 2H).

Example 21 The preparation of 4-chloro-5-(6-(2-(methylsulfonyl)prop-2-yl)-2-morpholinopyrimidin-4-yl)pyridin-2-amine (S-38)

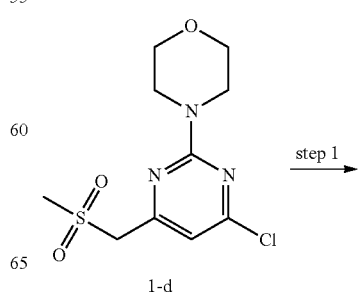

-continued

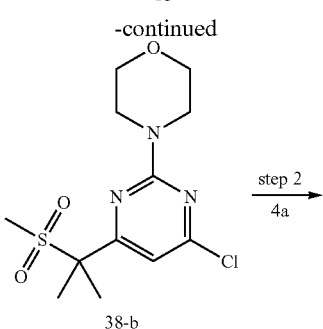

38-b

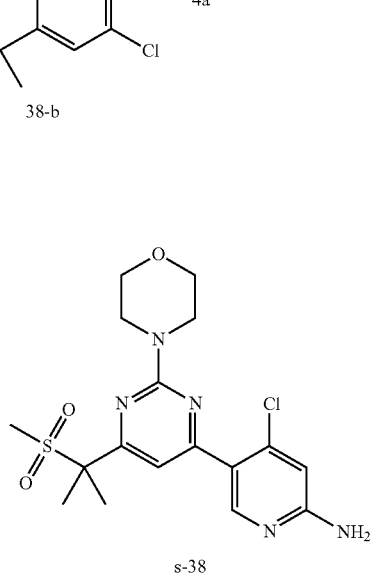

s-38

Step 1: 4-(4-chloro-6-(2-(methylsulfonyl)prop-2-yl)pyrimidin-2-yl)morpholine Compound 1-d (100 mg, 0.344 mmol), methyl iodide (146 mg, 1.031 mmol) and sodium hydride (53 mg, 1.376 mmol) were added to 5 ml of dimethylformamide and stirred at room temperature for 2 h. The reaction was completed and the mixture was extracted with water and ethyl acetate. The organic phases were separated, combined, and concentrated under reduced pressure to give crude compound 38-b (120 mg). Purity: 93%, spectrum data: MS m/z(ESI): 320[M+H]+. stirred at 120° C. under microwave for 10 minutes

Step 2: 4-chloro-5-(6-(2-(methylsulfonyl)prop-2-yl)-2-morpholinopyrimidin-4-yl) pyridin-2-amine The mixture of compound 38-b (50 mg, 0.157 mmol), compound 4a (120 mg, 0.47 mmol), Pd(dppf)Cl$_2$ ([1,1'-bis(diphenylphosphino)ferrocene]dichloropalladium) (5.76 mg, 0.0208 mol), sodium carbonate (34 mg, 0.314 mmol), and acetonitrile/water (4 ml/1 ml) was added to a sealed tube and stirred at 120° C. under microwave for 10 minutes. The reaction was completed and the mixture was cooled to room temperature and filtered. The filtrate was concentrated under reduced pressure to give crude product which was purified by Combi-flash column chromatography to obtain compound S-38 (7.68 mg). Purity: 100%. Spectrum data: MS m/z(ESI): 412[M+H]+. $^1$H NMR (500 MHz, CDCl$_3$) δ 8.41 (s, 1H), 7.24 (s, 1H), 6.59 (s, 1H), 4.70 (brs, 2H), 3.90-3.83 (m, 4H), 3.82-3.76 (m, 4H), 2.88 (s, 3H), 1.84 (s, 6H).

Example 22: The preparation of 1-(6-(6-amino-4-(trifluoromethyl)pyridin-3-yl)-2-morpholinopyrimidin-4-yl)cyclopropanecarboxylic acid (S-2)

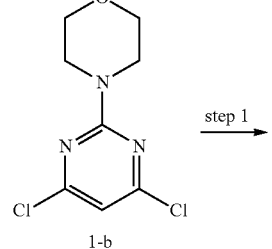

1-b

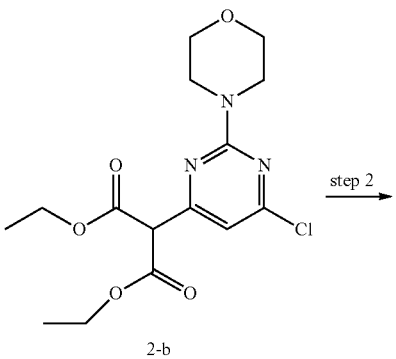

2-b

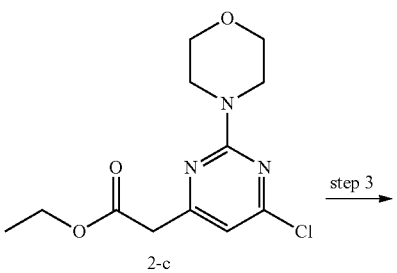

2-c

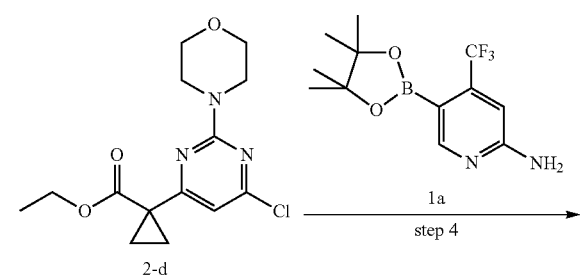

2-d

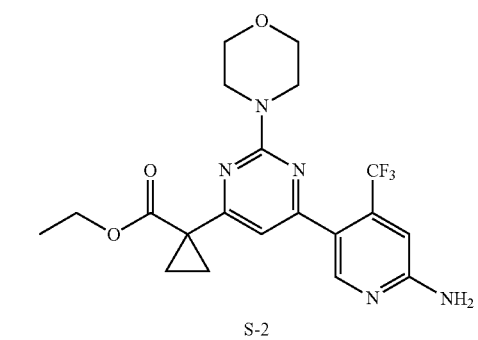

S-2

Step 1: diethyl 2-(6-chloro-2-morpholin-4-yl)malonate

The crude compound 2-b (440 mg) was obtained by referring to the synthesis method of step 2 in Example 1 and using compound 1-b (1.2 g) as the starting material except that methyl 2-(methylsulfonyl) acetate was replaced by diethyl malonate. Purity: 40%, spectrum data: MS m/z(ESI): 358[M+H]+.

Step 2: methyl 2-(6-chloro-2-morpholin-4-yl) acetate

Sodium chloride (80 mg, 1.35 mmol) was added to the solution of compound 2-b (320 mg, 0.9 mmol) in dimethyl sulfoxide/water (10 ml/0.5 ml) and stirred at 140° C. for 4 h. The reaction was completed. The mixture was cooled to room temperature and extracted by adding water and ethyl acetate. The combined organic phases were separated and concentrated under reduced pressure to give crude compound 2-c (280 mg) as an oil. Purity: 70%, spectrum data: MS m/z(ESI): 286[M+H]+.

Step 3: 1-(6-chloro-2-morpholin-4-yl)cyclopropane

The crude compound 2-d (140 mg) was obtained by referring to the synthesis method of step 4 in Example 1 and using compound 2-c (130 mg) as the starting material. Purity: 60%, spectrum data: MS m/z(ESI): 312[M+H]+.

Step 4: 1-(6-(6-amino-4-(trifluoromethyl)pyridin-3-yl)-2-morpholinopyrimidin-4-yl) cyclopropanecarboxylic acid The compound S-2 (54 mg) was obtained by referring to the synthesis method of step 5 in Example 1 and using compound 2-d (160 mg) as the starting material. Purity: 100%. Spectrum data: MS m/z(ESI): 438[M+H]+. $^1$H NMR (400 MHz, CDCl$_3$) δ 8.30 (s, 1H), 7.12 (s, 1H), 6.80 (s, 1H), 4.84 (brs, 2H), 4.20 (q, J=7.1 Hz, 2H), 3.86-3.67 (m, 8H), 1.64 (overlap, 4H), 1.26 (t, J=7.1 Hz, 3H).

Example 23 The preparation of (1-(6-(6-amino-4-(trifluoromethyl)pyridin-3-yl)-2-morpholinopyrimidin-4-yl)cyclopropyl)(morpholino)ketone (S-3)

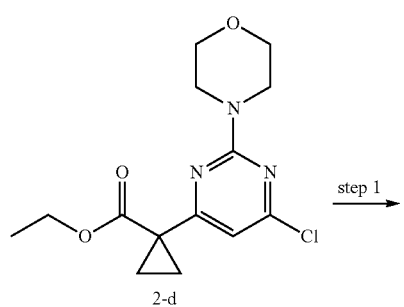

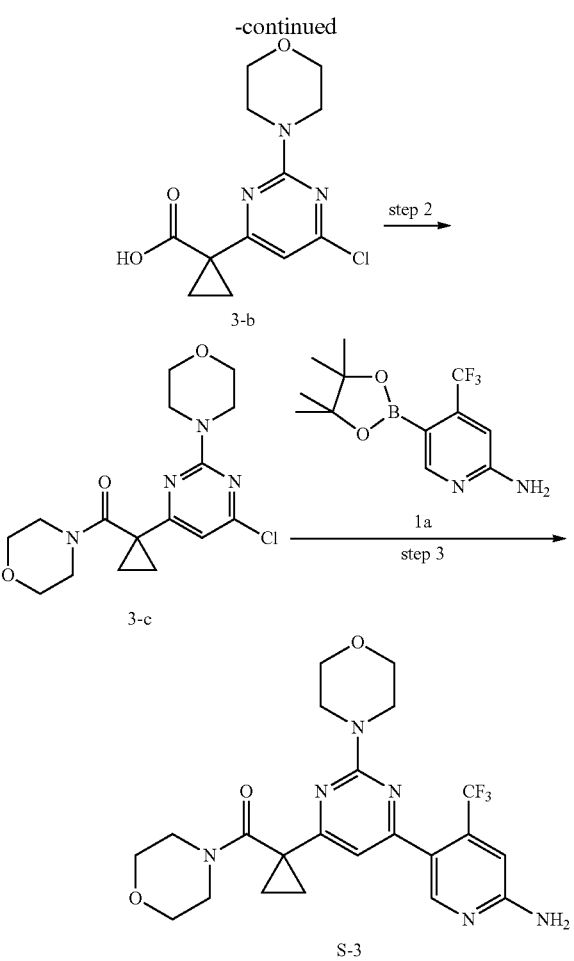

Step 1: 1-(6-chloro-2-morpholin-4-yl)cyclopropanecarboxylic acid

Sodium hydroxide (5N, 2.5 ml) was added to the solution of compound 2-d (50 mg, 0.16 mmol) in methanol (2.5 ml) and stirred at room temperature for 4 hours. The reaction was complete, and extracted by adding water and ethyl acetate. The combined organic phases were separated, and concentrated under reduced pressure to give compound 3-b (70 mg). Purity: 80%, spectrum data: MS m/z(ESI): 284 [M+H]+.

Step 2: (1-(6-chloro-2-morpholin-4-yl)cyclopropyl)(morpholino)ketone

Morpholine (32 mg, 0.36 mmol), triethylamine (50 mg, 0.48 mmol), 4-dimethylaminopyridine (5 mg, 0.024 mmol), and HATU (2-(7-azobenzotriazole)-N,N,N',N'-tetramethyluronium hexafluorophosphate) (110 mg, 0.288 mmol) were added to the solution of compound 3-b (70 mg, 0.24 mmol) in dichloromethane (5 ml) and stirred at room temperature for 2 hours. The reaction was completed, and extracted by adding water and dichloromethane. The combined organic phases were separated and concentrated under reduced pressure to give compound 3-c (80 mg). Purity: 80%, spectrum data: MS m/z(ESI): 353[M+H]+.

Step 3: (1-(6-(6-amino-4-(trifluoromethyl)pyridin-3-yl)-2-morpholinopyrimidin-4-yl) cyclopropyl)(morpholino)ketone Compound S-3 (100 mg) was obtained by referring to the synthesis method of step 5 in Example 1 and using compound 3-c (85 mg) as the starting material. Purity: 33%. Spectrum data: MS m/z(ESI): 479 [M+H]+. $^1$H NMR (400 MHz, CDCl$_3$) δ 8.24 (s, 1H), 6.79 (s, 1H), 6.53 (s, 1H), 4.84 (brs, 2H), 3.83-3.77 (m, 4H), 3.77-3.73 (m, 4H), 3.70-3.65 (m, 4H), 3.57-3.43 (m, 4H), 1.54-1.51 (m, 2H), 1.36 (q, J=4.4 Hz, 2H).

Example 24

Compound S-7 was obtained by referring to the synthesis method in Example 23 and using compound 2-d as the starting material except that morpholine was replaced by piperidine.

Step: borane (1 ml) was added to the solution of compound S-3 (120 mg, 0.2 mmol) in 10 ml of tetrahydrofuran and the mixture was stirred at room temperature for 1 hour. The reaction was completed and methanol was added. The mixture was concentrated under reduced pressure and extracted with water and ethyl acetate. The combined organic phases were separated and concentrated under reduced pressure to give the crude product which was separated and purified by preparative liquid chromatography to obtain compound S-8 (8.5 mg). Purity: 10%. Spectrum data: MS m/z(ESI): 465[M+H]+. $^1$H NMR (400 MHz, CDCl$_3$) δ 8.32 (s, 1H), 7.20 (s, 1H), 6.81 (s, 1H), 4.81 (brs, 2H), 3.79-3.72 (m, 8H), 3.65 (t, J=4.4 Hz, 4H), 2.67 (s, 2H), 2.48 (brs, 4H), 1.58 (overlap, 2H), 1.41 (q, J=3.6 Hz, 2H).

| No. | Structure | MS [M + H]+ | $^1$HNMR |
|---|---|---|---|
| example 24 | 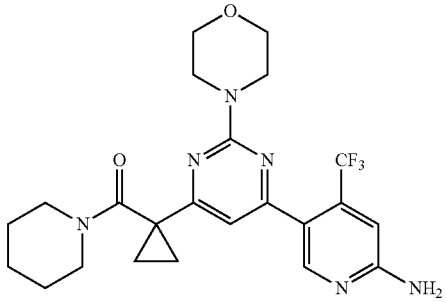 s-7 | 477 | $^1$H NMR (400 MHz, CDCl$_3$) δ 8.23 (s, 1H), 6.79 (s, 1H), 6.54 (s, 1H), 4.87 (brs, 2H), 3.84-3.71 (m, 8H), 3.61 (t, J = 4.8 Hz, 2H), 3.39 (t, J = 5.2 Hz, 2H), 1.62-1.52 (m, 6H), 1.46-1.37 (m, 4H). |

Example 25 The preparation of 5-(2-morpholino-6-(1-(morpholinomethyl)cyclopropyl)pyrimidin-4-yl)-4-(trifluoromethyl)pyridin-2-amine (S-8)

Example 26 The preparation of 5-(6-(1-(methylsulfonylmethyl)cyclopropyl)-2-morpholin-4-yl)-4-(trifluoromethyl)pyridin-2-amine (S-11)

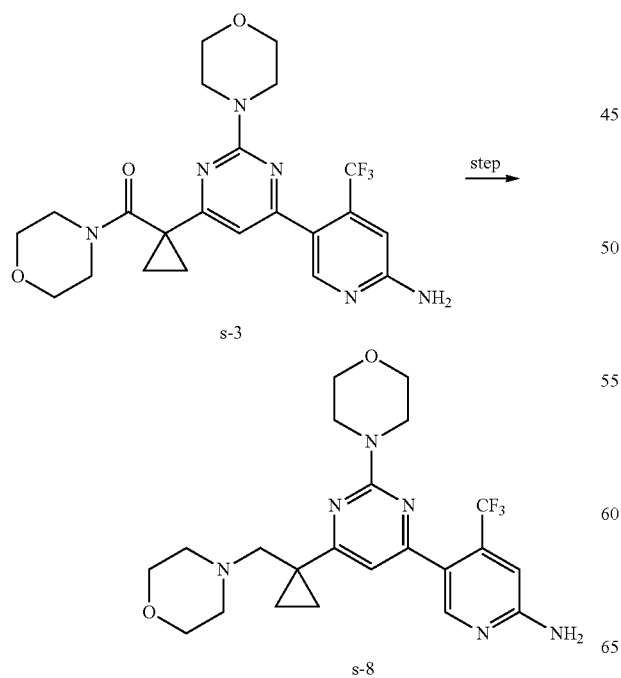

-continued

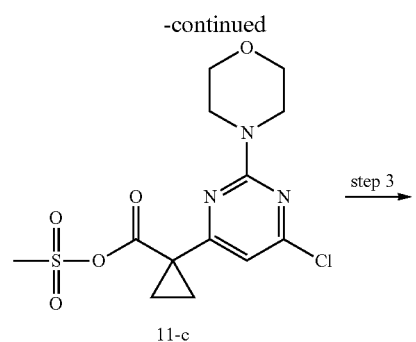

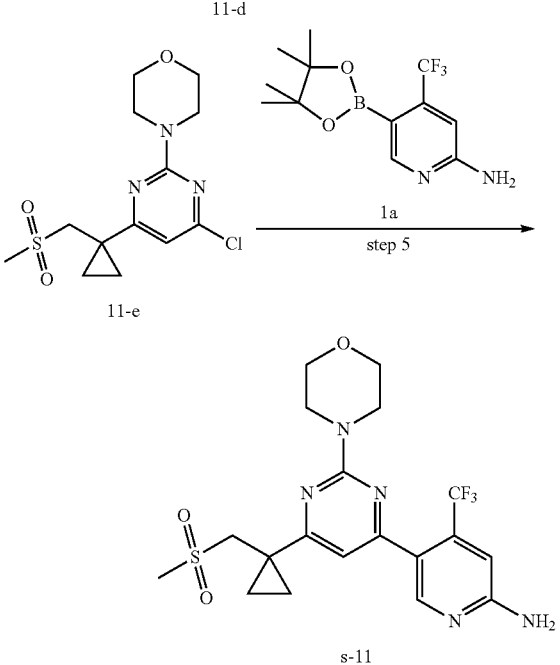

Step 1: (1-(6-chloro-2-morpholin-4-yl)cyclopropyl)methanol

Lithium aluminum hydride (32 mg, 0.28 mmol) was added to the solution of compound 2-d (50 mg, 0.18 mmol) in 5 ml of tetrahydrofuran at 0° C. and stirred at 0° C. to room temperature for 2 hours. The reaction was complete, and 3 drops of water, sodium hydroxide (5N, 3 drops), and 1 ml of water were added. The mixture was filtered and the filtrate was concentrated under reduced pressure to give the crude product which was purified by Combi-flash column chromatography to give compound 11-b (50 mg). Purity: 90%, yield: 30%. Spectrum data: MS m/z(ESI): 270[M+H]+.

Step 2: (1-(6-chloro-2-morpholin-4-yl)cyclopropyl)methylmethanesulfonate

Methanesulfonyl chloride (32 mg, 0.28 mmol) and triethylamine (40 mg, 0.37 mmol) were added to the solution of compound 11-b (50 mg, 0.18 mmol) in 5 ml of dichloromethane at 0° C. and stirred at 0° C. to room temperature for 2 hours. The reaction was completed and the mixture was extracted by adding water and dichloromethane, and dried over sodium sulfate. The organic phase was separated and concentrated under reduced pressure to give crude compound 11-c (60 mg). Purity: 80%. Spectrum data: MS m/z(ESI): 348[M+H]+.

Step 3: 4-(4-chloro-6-(1-(iodomethyl)cyclopropyl)pyrimidin-2-yl)morpholine

Sodium iodide (52 mg, 0.35 mmol) was added to the solution of compound 11-c (60 mg, 0.17 mmol) in 5 ml of acetone and stirred at room temperature overnight. The reaction was completed. The mixture was extracted by adding water and ethyl acetate, and dried over sodium sulfate. The organic phase was separated, and concentrated under reduced pressure to give crude compound 11-d (60 mg). Purity: 73%. Spectrum data: MS m/z(ESI): 380[M+H]+.

Step 4: 4-(4-chloro-6-(1-(methylsulfonylmethyl)cyclopropyl)pyrimidin-2-yl) morpholine Sodium methanesulfinate (30 mg, 0.24 mmol) was added to the solution of compound 11-d (60 mg, 0.16 mmol) in 5 ml of dimethylformamide and stirred at room temperature for 2 h. The reaction was completed and the mixture was extracted by adding water and ethyl acetate, and dried over sodium sulfate. The organic phase was separated and concentrated under reduced pressure to give crude compound 11-e (60 mg). Purity: 60%. Spectrum data: MS m/z(ESI): 332[M+H]+.

Step 5: 5-(6-(1-(methylsulfonylmethyl)cyclopropyl)-2-morpholin-4-yl)-4-(trifluoromethyl)pyridin-2-amine Compound S-11 (30 mg) as a white solid was obtained by referring to the synthesis method of step 5 in Example 1 and using compound 11-e (60 mg) as the starting material. Purity: 100%. Spectrum data: MS m/z(ESI): 458 [M+H]+. $^1$H NMR (400 MHz, CDCl$_3$) δ 8.25 (s, 1H), 6.79 (s, 1H), 6.34 (s, 1H), 4.86 (brs, 2H), 3.88-3.80 (m, 4H), 3.79-3.75 (m, 4H), 3.74 (s, 2H), 2.77 (s, 3H), 1.51-1.46 (m, 2H), 1.41-1.36 (m, 2H).

Example 27 The preparation of (S)-5-(6-(1-(isopropylsulfonyl)cyclobutyl)-2-(3-methylmorpholino)pyrimidin-4-yl)-4-(trifluoromethyl)pyridin-2-amine (S-13)

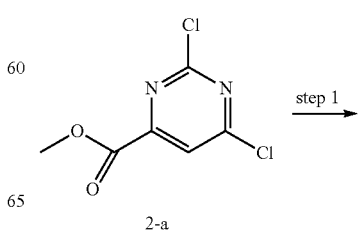

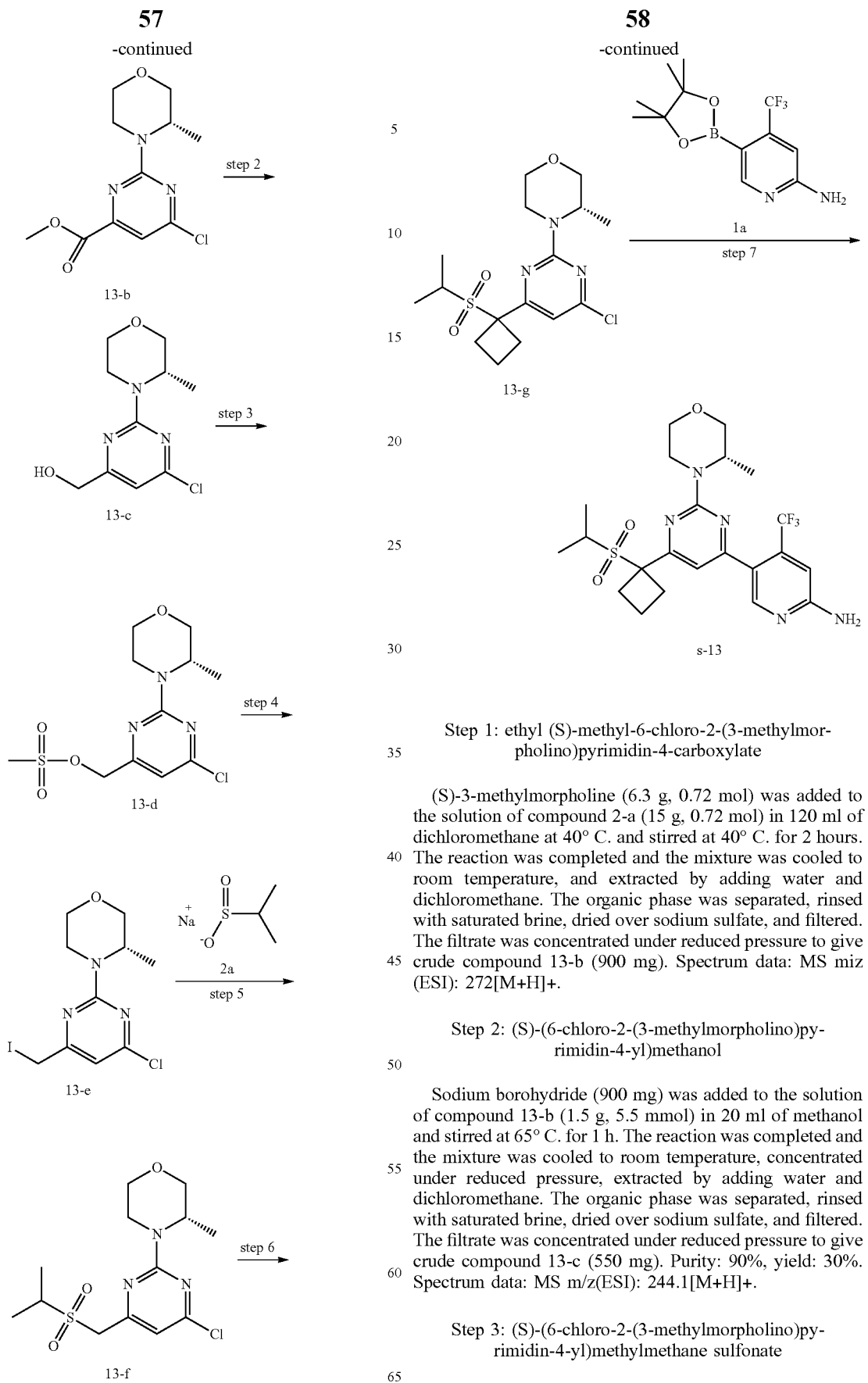

Step 1: ethyl (S)-methyl-6-chloro-2-(3-methylmorpholino)pyrimidin-4-carboxylate (S)-3-methylmorpholine (6.3 g, 0.72 mol) was added to the solution of compound 2-a (15 g, 0.72 mol) in 120 ml of dichloromethane at 40° C. and stirred at 40° C. for 2 hours. The reaction was completed and the mixture was cooled to room temperature, and extracted by adding water and dichloromethane. The organic phase was separated, rinsed with saturated brine, dried over sodium sulfate, and filtered. The filtrate was concentrated under reduced pressure to give crude compound 13-b (900 mg). Spectrum data: MS m/z (ESI): 272[M+H]+.

Step 2: (S)-(6-chloro-2-(3-methylmorpholino)pyrimidin-4-yl)methanol

Sodium borohydride (900 mg) was added to the solution of compound 13-b (1.5 g, 5.5 mmol) in 20 ml of methanol and stirred at 65° C. for 1 h. The reaction was completed and the mixture was cooled to room temperature, concentrated under reduced pressure, extracted by adding water and dichloromethane. The organic phase was separated, rinsed with saturated brine, dried over sodium sulfate, and filtered. The filtrate was concentrated under reduced pressure to give crude compound 13-c (550 mg). Purity: 90%, yield: 30%. Spectrum data: MS m/z(ESI): 244.1[M+H]+.

Step 3: (S)-(6-chloro-2-(3-methylmorpholino)pyrimidin-4-yl)methylmethane sulfonate Compound 13-d (740 mg) was obtained by referring to the synthesis method of step 2 in Example 26 and using compound 13-c (550 mg) as the starting material. Purity: 96%. Spectrum data: MS m/z(ESI): 322.0[M+H]+.

Step 4: (S)-4-(4-chloro-6-(iodomethyl)pyrimidin-2-yl)-3-methylmorpholine

Compound 13-e (680 mg) was obtained by referring to the synthesis method of step 3 in Example 26 and using compound 13-d (740 mg) as the starting material. Spectrum data: MS m/z(ESI): 354.0[M±H]+.

Step 5: (S)-4-(4-chloro-6-(isopropylsulfonylmethyl)pyrimidin-2-yl)-3-methyl morpholine Compound 13-f (45 mg) was obtained by referring to the synthesis method of step 4 in Example 26 and using compound 13-e (225 mg) as the starting material except that sodium methanesulfinate in the step was replaced by 2a. Spectrum data: MS m/z(ESI): 334.1 [M+H]+.

Step 6: (S)-4-(4-chloro-6-(1-(isopropylsulfonyl)cyclobutyl)pyrimidin-2-yl)-3-methyl morpholine Compound 13-g (0.02 g) as a pale yellow oil was obtained by referring to the synthesis method of step 4 in Example 1 and using compound 13-f (0.045 g) as the starting material except that 1,2-dibromoethane was replaced by 1,3-dibromoethane. Purity: 46.4%, yield: 39.7%. Spectrum data: MS m/z(ESI): 374.12[M+H]+.

Step 7: (S)-5-(6-(1-(isopropylsulfonyl)cyclobutyl)-2-(3-methylmorpholino)pyrimidin-4-yl)-4-(trifluoromethyl)pyridin-2-amine Compound S-13 (3.2 mg) as a yellow solid was obtained by referring to the synthesis method of step 5 in Example 1 and using compound 13-g (0.02 g) as the starting material. Purity: 20.5%, yield: 11.96%. Spectrum data: MS m/z(ESI): 500.19[M+H]+. $^1$H NMR (400 MHz, DMSO) δ 8.25 (s, 1H), 6.96 (s, 1H), 6.95 (s, 21H), 6.86 (s, 1H), 4.66 (d, J=6.6 Hz, 1H), 4.30 (d, J=11.9 Hz, 1H), 3.94 (d, J=8.4 Hz, 1H), 3.73 (d, J=11.5 Hz, 1H), 3.61 (d, J=8.7 Hz, 1H), 3.49-3.41 (m, 1H), 3.21 (m, 1H), 2.94 (m, 2H), 2.83 (m, 2H), 2.77 (m, 1H), 2.02-1.86 (m, 2H), 1.22 (d, J=6.8 Hz, 3H), 1.14 (m, 6H).

Examples 28-38

Compounds S-15 and S-23 were obtained by referring to the method in Example 27 and using compound 2-a as the starting material except that 2a in step 5 was replaced by sodium benzenesultinate and sodium ethanesulfinate, respectively.

Compounds S-18 and S-22 were obtained by referring to the method in Example 27 and using compound 2-a as the starting material except that (S)-3-methylmorpholine in step 1 was replaced by morpholine and 1,3-dibromopropane in step 6 was replaced by 1,2-dibromoethane and methyl iodide, respectively.

Compound S-19 was obtained by referring to the method in Example 27 and using compound 2-a as the starting material except that (S)-3-methylmorpholine in step 1 was replaced by morpholine.

Compound S-20 was obtained by referring to the method in Example 27 and using compound 2-a as the starting material except that (S)-3-methylmorpholine in step 1 was replaced by morpholine, and sodium propane-2-sulfonic acid in step 5 was replaced by sodium benzenesulfinate.

Compounds S-21, S-25, S-28, and S-29 were obtained by referring to the method in Example 27 and using compound 2-a as the starting material except that (S)-3-methylmorpholine in step 1 was replaced by morpholine, 2a in step 5 was replaced by sodium benzenesulfinate, sodium benzenesulfinate, sodium ethanesulfinate, and sodium ethanesulfinate, respectively, and 1,3-dibromopropane in step 6 was replaced by methyl iodide, 1,2-dibromoethane, 1,2-dibromoethane, and methyl iodide, respectively.

Compound S41 was obtained by referring to the method in Example 27 and using compound 2-a as the starting material except that 2a in step 5 was replaced by sodium methylsulfinate, and 1,3-dibromopropane in step 6 was replaced by methyl iodide.

| No. | structure | MS [M + H]+ | $^1$HNMR |
|---|---|---|---|
| Example 28 | 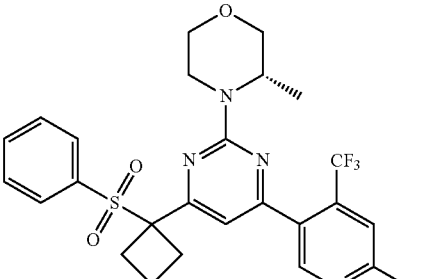<br>s-15 | 534.17 | $^1$H NMR (400 MHz, DMSO) δ 8.43 (brs, 1H, HCOOH), 8.14 (s, 1H), 7.68 (s, 1H), 7.46 (t, J = 7.7 Hz, 2H), 7.38 (d, J = 7.8 Hz, 2H), 6.92 (brs, 2H), 6.85 (s, 1H), 6.79 (s, 1H), 4.32-4.19 (m, 1H), 3.76 (d, J = 11.4 Hz, 1H), 3.58 (d, J = 11.2 Hz, 1H), 3.25-3.15 (m, 3H), 3.05-2.93 (m, 2H), 2.81-2.69 (m 2H), 2.13-1.97 (m, 2H), 0.97 (d, J = 6.5 Hz, 3H). |

-continued

| No. | structure | MS [M + H]+ | ¹HNMR |
|---|---|---|---|
| Example 29 | s-18 | 472 | ¹H NMR (500 MHz, CDCl₃) δ 8.29 (s, 1H), 7.20 (s, 1H), 6.80 (s, 1H), 4.85 (brs, 2H), 3.84-3.80 (m, 4H), 3.79-3.74 (m, 4H), 3.47-3.26 (m, 1H), 1.83-1.79 (m-2H), 1.60-1.53 (m, 2H), 1.40 (s, 3H), 1.38 (s, 3H). |
| Example 30 | s-19 | 486 | ¹H NMR (500 MHz, CDCl₃) δ 8.30 (s, 1H), 7.02 (s, 1H), 6.80 (s, 1H), 4.88 (brs, 2H), 3.89-3.84 (m, 4H), 3.75-3.80 (m, 4H), 3.22-3.12 (m, 2H), 2.84-2.75 (m, 3H), 2.19-2.08 (m, 1H), 2.01-1.95 (m, 1H), 1.27 (s, 3H), 1.26 (s, 3H). |
| Example 31 | s-20 | 520 | ¹H NMR (500 MHz, CDCl₃) δ 8.24 (s, 1H), 7.56 (t, J = 7.4 Hz, 1H), 7.46 (d, J = 7.4 Hz, 2H), 7.37 (t, J = 7.8 Hz, 2H), 6.87 (s, 1H), 6.82 (s, 1H), 4.89 (brs, 2H), 3.64-3.55 (m, 4H), 3.51-3.42 (m, 4H), 3.27-3.08 (m, 2H), 2.83-2.66 (m, 2H), 2.32-2.28 (m, 1H), 2.01-1.91 (m, 1H). |
| Example 32 | s-21 | 508 | ¹H NMR (500 MHz, CDCl₃) δ 8.26 (s, 1H), 7.59 (t, J = 7.4 Hz, 1H), 7.50 (dd, J = 8.0, 1.0 Hz, 2H), 7.40 (t, J = 7.8 Hz, 2H), 7.01 (s, 1H), 6.83 (s, 1H), 4.88 (brs, 2H), 3.61-3.56 (m, 4H), 3.54-4.42 (m, 4H), 1.83 (s, 6H). |

| No. | structure | MS [M + H]+ | ¹HNMR |
|---|---|---|---|
| Example 33 | s-22 | 474 | ¹H NMR (500 MHz, CDCl₃) δ 8.28 (s, 1H), 7.10 (s, 1H), 6.81 (s, 1H), 4.90 (brs, 2H), 3.91-3.81 (m, 4H), 3.81-3.70 (m, 4H), 3.48-3.35 (m, 1H), 1.84 (s, 6H), 1.20 (s, 3H), 1.18(s, 3H). |
| Example 34 | s-23 | 486.2 | ¹H NMR (400 MHz, DMSO) δ 8.24 (s, 1H), 7.56 (s, 1H), 6.94 (brs, 2H), 6.86 (s, 1H), 4.65 (s, 1H), 4.29 (d, J = 13.4 Hz, 1H), 3.93 (d, J = 9.0 Hz, 1H), 3.72 (d, J = 11.2 Hz, 1H), 3.65-3.55 (m, 1H), 3.50-3.38 (m, 1H), 3.24-3.09 (m, 1H), 3.05-2.83 (m, 4H), 2.82-2.68 (m, 2H), 2.14-1.82 (m, 2H), 1.20 (d, J = 5.4 Hz, 3H), 1.16-0.94 (m, 3H). |
| Example 35 | s-25 | 506 | ¹H NMR (400 MHz, CDCl₃) δ 8.16 (s, 1H), 7.78-7.70 (m, 2H), 7.59 (t, J = 7.4 Hz, 1H), 7.47 (t, J = 7.8 Hz, 2H), 7.06 (s, 1H), 6.80 (s, 1H), 4.86 (brs, 2H), 3.63-3.59 (m, 8H), 2.01 (dd, J = 7.2, 4.4 Hz, 2H), 1.60 (dd, J = 7.2, 4.4 Hz, 2H). |
| Example 36 | s-28 | 458.1 | ¹H NMR (500 MHz, DMSO) δ 8.25 (s, 1H), 7.03 (s, 1H), 6.94 (brs, 2H), 6.86 (s, 1H), 3.75-3.69 (m, 4H), 3.68-3.64 (m, 4H), 3.36 (q, J = 7.5 Hz, 2H), 1.68-1.62 (m, 2H), 1.61-1.56 (m, 2H), 1.27 (t, J = 7.4 Hz, 3H). |

| No. | structure | MS [M + H]+ | ¹HNMR |
|---|---|---|---|
| Example 37 | 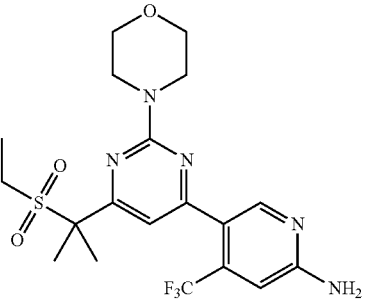 s-29 | 460.2 | ¹H NMR (500 MHz, DMSO) δ 8.23 (s, 1H), 7.05 (s, 1H), 6.94 (brs, 2H), 6.87 (s, 1H), 3.79-3.71 (m, 4H), 3.70-3.62 (m, 4H), 3.13 (q, J = 7.4 Hz, 2H), 1.74 (s, 6H), 1.13 (t, J = 7.4 Hz, 3H). |
| Example 38 | 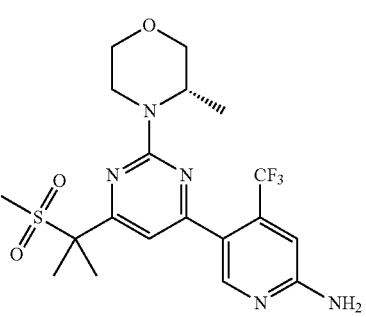 S-41 | 460 | ¹H NMR (500 MHz, CDCl₃) δ 8.31 (s, 1H), 6.99 (s, 1H), 6.80 (s, 1H), 4.87 (brs, 2H), 4.80-4.64 (m, 1H), 4.38 (dd, J = 13.6, 2.3 Hz, 1H), 3.99 (dd, J = 11.3, 3.5 Hz, 1H), 3.78 (d, J = 11.4 Hz, 1H), 3.72 (dd, J = 11.5, 3.0 Hz, 1H), 3.56 (td, J = 11.9, 3.0 Hz, 1H), 3.29 (td, J = 13.0, 3.8 Hz, 1H), 2.84 (s, 3H), 1.83 (s, 3H), 1.83 (s, 3H), 1.30 (d, J = 6.8 Hz, 4H). |
Example 39: The preparation of N-(1-(6-(6-amino-4-(trifluoromethyl)pyridin-3-yl)-2-morpholinopyrimidin-4-yl)cyclopropyl)-N-methylmethanesulfonamide (S-14)
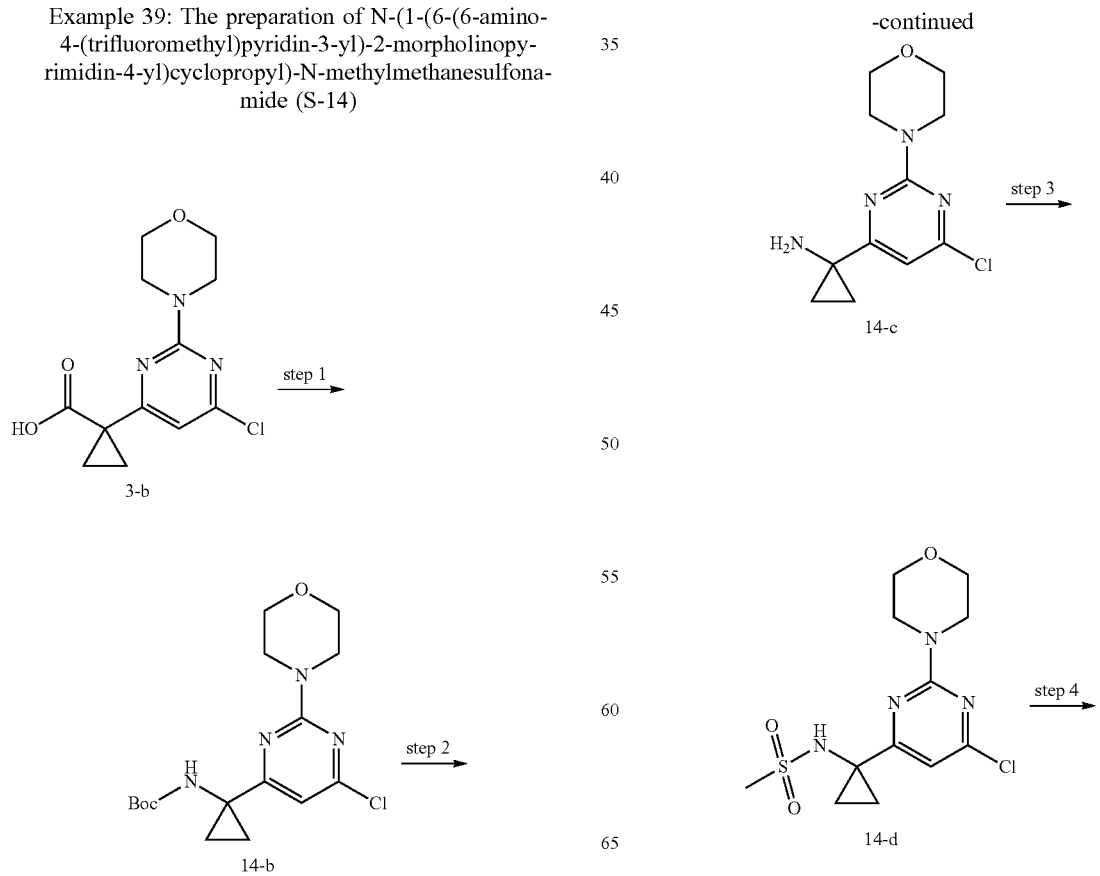

Step 4: N-(1-(6-chloro-2-morpholin-4-yl)cyclopropyl)-N-methylmethanesulfonamide

Sodium hydride (0.013 g, 0.00034 mol) was added to the solution of compound 14-d (0.087 g, 0.00026 mol) in 6 ml of dimethylformamid at 0° C. and stirred at 0° C. for 10 minutes. Methyl iodide (0.055 g, 0.00039 mol) was added and stirred at room temperature for 4-16 h. The reaction was complete, saturated ammonium chloride solution and ethyl acetate were added and the organic phase was separated and concentrated under reduced pressure to give crude product which was purified by Combi-flashcolumn chromatography to give compound 14-e (0.06 g) as a pale yellow solid. Purity: 53%. Spectrum data: MS m/z(ESI): 347.09[M+H]+.

Step 5: N-(1-(6-(6-amino-4-(trifluoromethyl)pyridin-3-yl)-2-morpholino pyrimidin-4-yl)cyclopropyl)-N-methylmethanesulfonamide Compound S-14 (33.65 mg) as a white solid was obtained by referring to the synthesis method of step 5 in example 1 and using compound 14-e (0.06 g) as the starting material. Purity: 56.7%, yield: 41.0%. Spectrum data: MS m/z(ESI): 473.15[M+H]+. $^1$H NMR (400 MHz, DMSO) δ 8.18 (s, 1H), 6.89 (brs, 2H), 6.85 (s, 1H), 6.81 (s, 1H), 3.60-3.70 (m, 8H), 2.97 (d, J=7.0 Hz, 6H), 1.42-1.67 (m, 4H).

Example 40 The preparation of N-(1-(6-(6-amino-4-(trifluoromethyl)pyridin-3-yl)-2-morpholinopyrimidin-4-yl)cyclopropyl)methanesulfon amide (S-24)

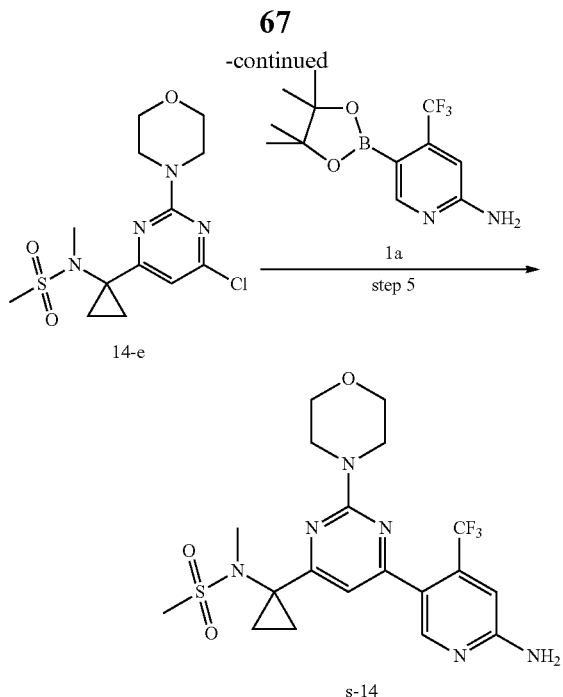

Step 1: tert-butyl-1-(6-chloro-2-morpholinopyrimidin-4-yl)cyclopropyl aminoformate Triethylamine (0.30 g, 0.0030 mol) and diphenyl azidophosphate (0.82 g, 0.0030 mol) were added to the solution of compound 3-b (0.71 g, 0.0025 mol) in 25 ml of toluene and stirred at room temperature for 1 h. Tert-butanol (7 ml) was added and stirred at 100° C. for 16 hours. The reaction was completed and the mixture was cooled to room temperature, added with water and ethyl acetate. The organic phase was separated, rinsed with 26% brine, and dried over sodium sulfate. The organic phase was separated and concentrated under reduced pressure to give the crude product which was purified by Combi-flashcolumn chromatography to give compound 14-b (0.27 g) as an orange oil. Purity: 30.3%. Spectrum data: MS m/z(ESI): 355.15[M+H]+.

Step 2: 1-(6-chloro-2-morpholin-4-yl)cyclopropylamine 5 ml of trifluoroacetic acid was added to the solution of compound 14-b (0.27 g, 0.00076 mol) in 5 ml of dichloromethane and stirred at room temperature for 2~4 h. The reaction was complete, and trifluoroacetic acid was concentrated at room temperature under reduced pressure. Dichloromethane and saturated sodium bicarbonate solution were added, and the organic phase was separated and dried over sodium sulfate. The organic phase was separated, concentrated under reduced pressure at below 50° C. to give compound 14-c (0.2 g) as a pale yellow solid. Purity: 75.5/%. Spectrum data: MS m/z(ESI): 255.09[M±H]+.

Step 3: N-(1-(6-chloro-2-morpholin-4-yl)cyclopropyl)methanesulfonamide

Compound 14-d (0.17 g) as a yellow oil was obtained by referring to the synthesis method of step 2 in example 26 and using compound 14-c (0.1 g) as the starting material. Purity: 62%. Spectrum data: MS m/z(ESI): 333.07[M+H]+.

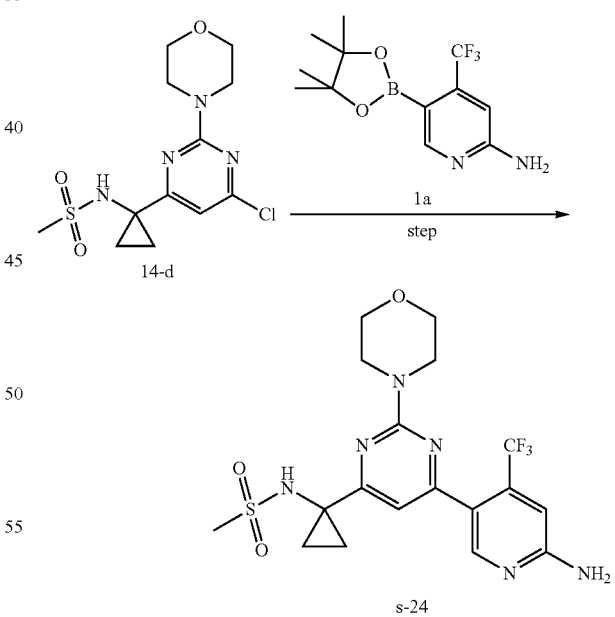

Step: Compound S-24 (5.12 mg) was obtained by referring to the synthesis method of step 5 in example 1 and using compound 14-d (50 mg) as the starting material. Spectrum data: MS m/z(ESI): 459.1[M+H]+. $^1$H NMR (400 MHz, CDCl$_3$) δ 8.25 (s, 1H), 6.80 (s, 1H), 6.58 (s, 1H), 5.77 (s, 1H), 4.87 (brs, 2H), 3.84-3.82 (m, 4H), 3.78-3.74 (m, 4H), 1.68 (dd, J=7.9, 4.8 Hz, 2H), 1.51 (dd, J=7.9, 4.8 Hz, 2H).

Example 41 The preparation of N-(1-(6-(6-amino-4-(trifluoromethyl)pyridin-3-yl)-2-morpholinopyrimidin-4-yl)cyclopropyl)acetamide (S-26)

Example 42 The preparation of (S)-5-(6-(1-(methylamino)cyclobutyl)-2-(3-methylmorpholino)pyrimidin-4-yl)-4-(trifluoromethyl)pyridin-2-amine (S-27)

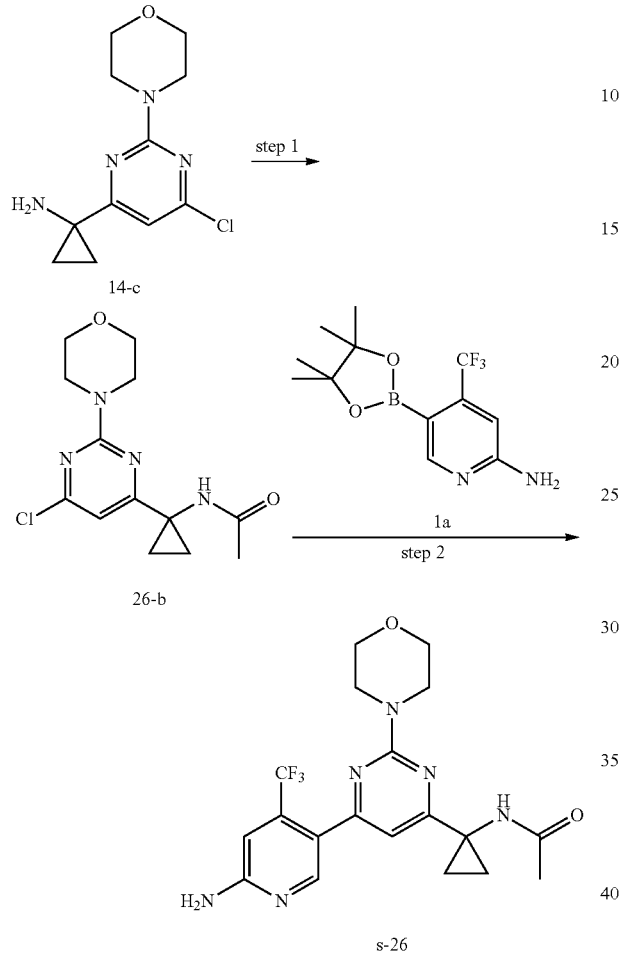

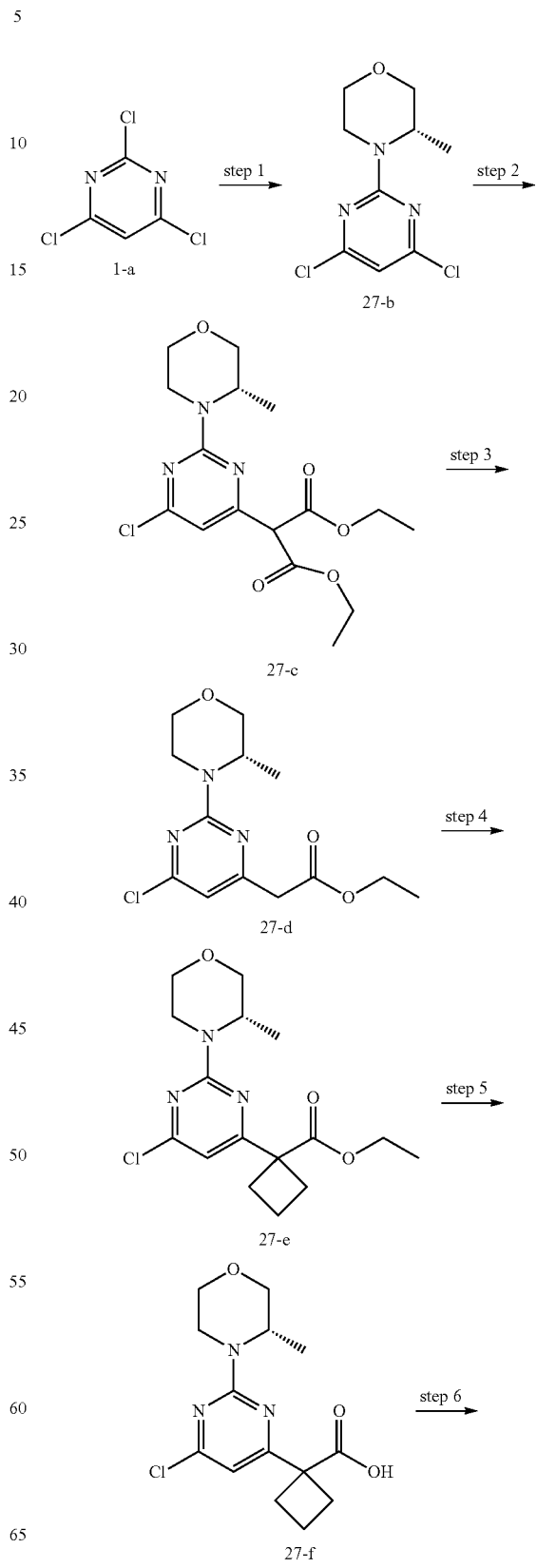

Step 1: N-(1-(6-chloro-2-morpholin-4-yl)cyclopropyl)acetamide

Compound 26-b (50 mg) as a white solid was obtained by referring to the synthesis method of step 2 in example 26 and using compound 14-c (0.09 g) as the starting material except that methanesulfonyl chloride in the step was replaced by acetyl chloride. Purity: 65.7%. Spectrum data: MS m/z (ESI): 297.10[M+H]+.

Step 2: N-(1-(6-(6-amino-4-(trifluoromethyl)pyridin-3-yl)-2-morpholino pyrimidin-4-yl)cyclopropyl)acetamide Compound S-26 (7.12 mg) as a white solid was obtained by referring to the synthesis method of step 5 in Example 1 and using compound 26-b (0.05 g) as a starting material. Spectrum data: MS m/z(ESI): 423.17[M+H]+. $^1$H NMR (400 MHz, Acetone) δ 8.19 (s, 1H), 7.82 (s, 1H), 6.94 (s, 1H), 6.87 (s, 1H), 6.21 (brs, 2H), 3.75-3.70 (m, 4H), 3.69-3.64 (m, 4H), 1.95 (s, 3H), 1.62-1.59 (m, 2H), 1.22-1.19 (m, 2H).

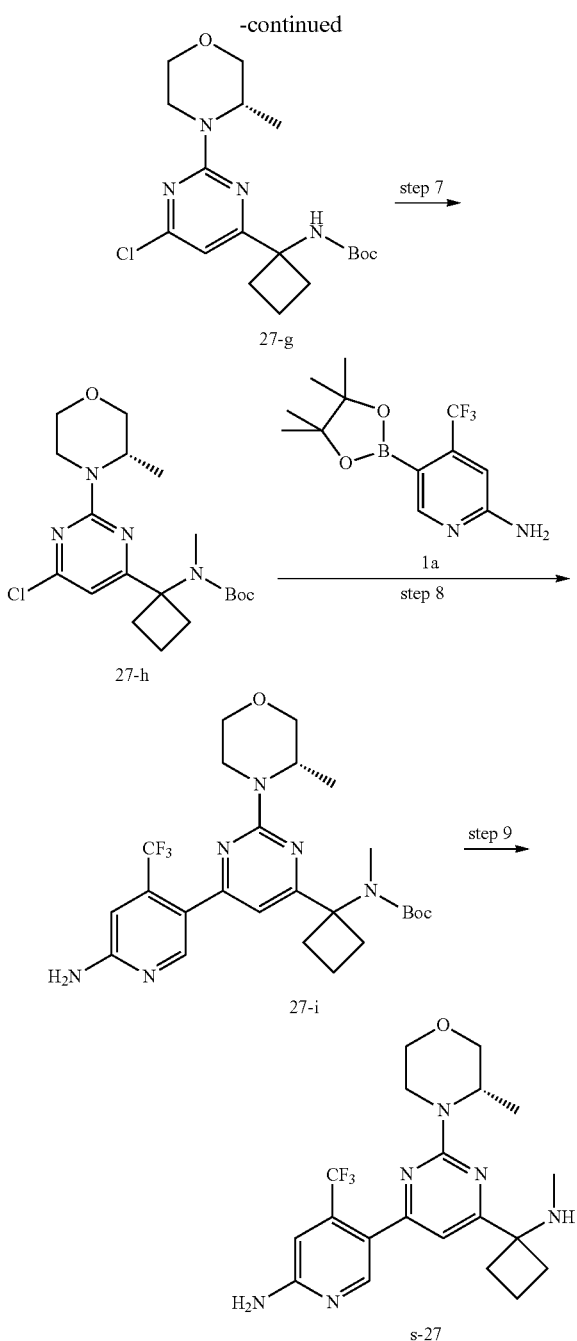

Step 1: (S)-4-(4,6-dichloropyrimidin-2-yl)-3-methylmorpholine

Compound 27-b (3.6 g) as a white solid was obtained by referring to the synthesis method of step 1 in Example 1 and using compound 1-a (10.0 g) as the starting material except that morpholine in the step was replaced by (S)-3-methylmorpholine. Purity: 44.3%, yield: 26.5%. Spectrum data: MS m/z(ESI): 248.1 [M+H]+.

Step 2: (S)-diethyl 2-(6-chloro-2-(3-methylmorpholino)pyrimidin-4-yl)malonate Diethyl malonate (2.33 g, 0.014 mol), and sodium hydride (0.87 g, 0.021 mol) were added to the compound 27-b (3.6 g, 0.014 mol) in 50 ml of dimethyl sulfoxide under Ar at 100° C. and stirred under microwave for 3-5 h. The mixture was cooled to room temperature, and diethyl malonate (2.33 g, 0.014 mol) and sodium hydride (0.87 g, 0.021 mol) were added and stirred at 100° C. under microwave for 3 h. The reaction was complete, the mixture was cooled to room temperature, and saturated ammonium chloride and ethyl acetate were added. The combined organic phases were separated, rinsed with 26% brine, and dried over sodium sulfate. The organic phase was separated and concentrated under reduced pressure to give the crude product which was purified by Combi-flash column chromatography to obtain compound 27-c (2.7 g) as an orange oil. Purity: 85%, yield: 49.9%. Spectrum data: MS m/z(ESI): 372.2[M+H]+.

Step 3: (S)-ethyl 2-(6-chloro-2-(3-methylmorpholino)pyrimidin-4-yl)acetate

Compound 27-d (1.0 g) as a pale yellow oil was obtained by using compound 27-c (2.7 g) as the starting material and referring to the synthesis method of Step 2 in Example 22. Purity: 98%, spectrum data: MS m/z(ESI): 300.0[M+H]+.

Step 4: (S)-ethyl 1-(6-chloro-2-(3-methylmorpholino)pyrimidin-4-yl)cyclobutane carboxylate Compound 27-e (1.1 g) as a yellow oil was obtained by using compound 27-d (1.0 g) as the starting material and referring to the synthesis method of Step 4 in Example 1 except that 1,2-dibromoethane in the step was replaced by 1,3-dibromopropane. Purity: 33%, spectrum data: MS m/z (ESI): 340.2[M+H]+.

Step 5: (S)-1-(6-chloro-2-(3-methylmorpholino)pyrimidin-4-yl)cyclobutane carboxylic acid Lithium hydroxide (4N, 8 ml) was added to the solution of compound 27-e (1.1 g, 0.0032 mol) in dioxane (8 ml) under Ar and stirred at room temperature for 2-4 h. The reaction was complete, and ethyl acetate was added. The aqueous phase was separated, and the pH was adjusted to 2 to 3 with 2N hydrochloric acid. The mixture was extracted with ethyl acetate. The organic phase was separated and rinsed with 26% brine, and the organic phase was separated and concentrated under reduced pressure to give compound 27-f (0.48 g) as a yellow oil. Purity: 88.4%, spectrum data: MS m/z(ESI): 312.1[M+H]+.

Step 6: (S)-tert-butyl 1-(6-chloro-2-(3-methylmorpholino)pyrimidin-4-yl)cyclobutyl aminocarboxylate Compound 27-g (210 mg) as a white solid was obtained by using compound 27-f (0.048 g) as the starting material and referring to the synthesis method of Step 1 in Example 39. Purity: 22.7%, yield: 35.6%. Spectrum data: MS m/z (ESI): 383.1[M+H]+.

Step 7: (S)-tert-butyl 1-(6-chloro-2-(3-methylmorpholino)pyrimidin-4-yl)cyclobutyl(methyl)aminoformic acid Compound 27-g (0.1 g, 0.00026 mol) and methyl iodide (0.044 g, 0.00031 mol) were added to the solution of sodium hydride (0.012 g, 0.00031 mol) in 5 ml of dimethylformamide under Ar and stirred at room temperature for 3 h. The reaction was complete and the mixture was cooled to 5-10° C., poured into water, and extracted with ethyl acetate. The organic phase was separated and rinsed with 26% brine. The organic phase was separated and concentrated under reduced pressure to give a crude product which was purified by Combi-flash column chromatography to obtain compound 27-h (30 mg) as a pale yellow oil. Purity: 95%, yield: 28.9%. Spectrum data: MS m/z(ESI): 397.3[M+H]+.

Step 8: (S)-tert-butyl 1-(6-(6-amino-4-(trifluoromethyl)pyridin-3-yl)-2-(3-methylmorpholino)pyrimidin-4-yl)cyclobutyl(methyl)aminoformic acid Compound 27-i (130 mg) as an orange oil was obtained by using compound 27-h (0.03 g) as the starting material and referring to the synthesis method of Step 5 in Example 1. Purity: 59%. Spectrum data: MS m/z(ESI): 523.3[M+H]+.

Step 9: (S)-5-(6-(1-(methylamino)cyclobutyl)-2-(3-methylmorpholino)pyrimidin-4-yl)-4-(trifluoromethyl)pyridin-2-amine Compound S-27 (13.9 mg) as a white solid was obtained by using compound 27-I (0.03 g) as the starting material and referring to the synthesis method of Step 3 in Example 39, separated and purified by preparative liquid chromatography. Purity: 100%, yield: 41.0%. Spectrum data: MS m/z (ESI): 423.2[M+H]+. $^1$H NMR (500 MHz, DMSO) δ 8.20 (s, 1H), 6.91 (s, 1H), 6.84 (s, 1H), 6.84 (brs, 2H), 4.67 (d, J=6.6 Hz, 11H), 4.33 (d, J=12.0 Hz, 1H), 3.93 (dd, J=11.1, 3.2 Hz, 1H), 3.72 (d, J=11.4 Hz, 1H), 3.61 (dd, J=11.4, 3.0 Hz, 1H), 3.49-3.41 (m, 1H), 3.20-3.12 (m, 1H), 2.41-2.33 (m, 2H), 2.11-2.03 (m, 2H), 2.02 (s, 3H), 1.92-1.80 (m, 2H), 1.20 (d, J=6.7 Hz, 3H).

Example 43 The preparation of N,N-dimethyl-5-(6-(1-(methylsulfonyl)cyclopropyl)-2-morpholinopyrimidin-4-yl)-4-(trifluoromethyl)pyridin-2-amine (S-35)

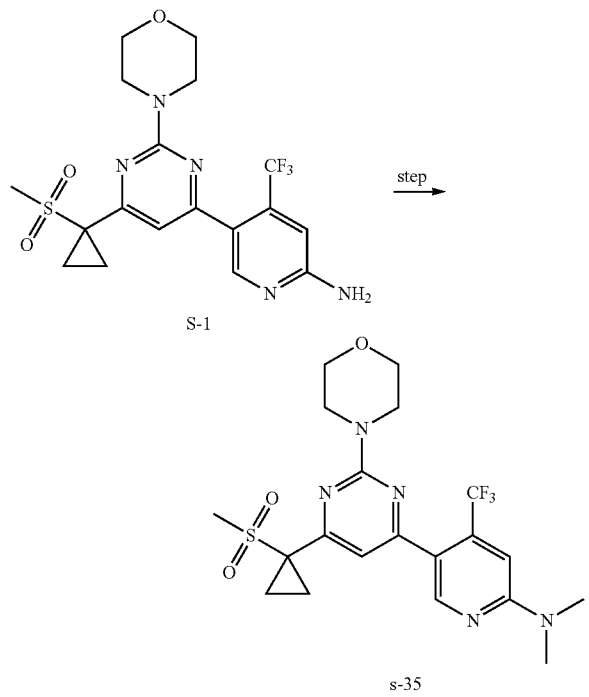

Step: an excess amount of sodium hydrogen and methyl iodide were added to the solution of compound S-1 (30 mg, 0.067 mmol) in 5 ml of dimethylformamide under argon and stirred at room temperature for 2 hours. The reaction was complete and water and ethyl acetate were added. The organic phase was separated and concentrated under reduced pressure to give the crude product which was purified by preparative liquid chromatography to obtain compound S-35 (8.5 mg). Purity: 80%. Spectrum data: MS m/z(ESI): 472 [M+H]+. $^1$H NMR (500 MHz, CDCl$_3$) δ 8.41 (s, 1H), 7.10 (s, 1H), 6.77 (s, 1H), 3.86-3.79 (m, 4H), 3.79-3.74 (m, 4H), 3.19 (s, 6H), 3.08 (s, 3H), 1.86 (q, J=4.6 Hz, 2H) 1.59-1.55 (m, 2H).

Example 44 The preparation of 5-(6-(1-(methylsulfonyl)cyclopropyl)-2-morpholinopyrimidin-4-yl)-3-(trifluoromethyl)pyridin-2-amine (S-44)

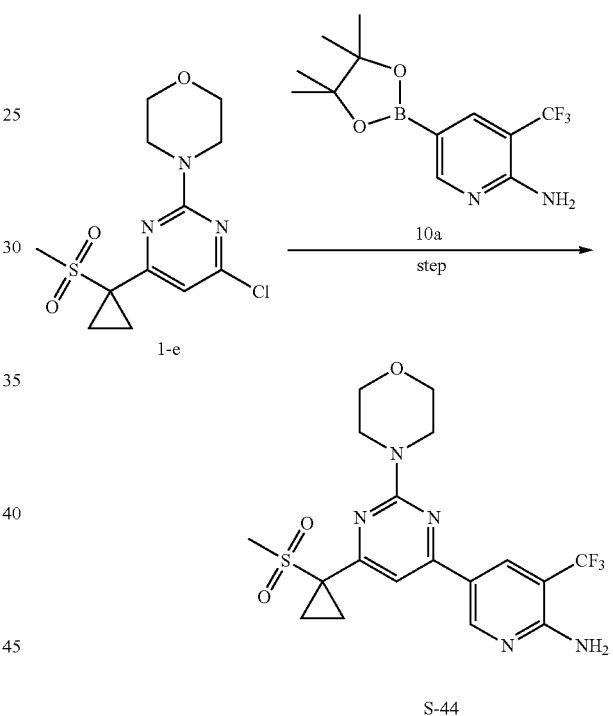

Step: Compound S-44 (10.8 mg) was obtained by using compound 1-e (50 mg) as the starting material and referring to the synthesis method of Step 5 in Example 1 except that 1a in the step was replaced by 10a. Purity: 100%. Spectrum data: MS m/z(ESI): 444[M+H]+. $^1$H NMR (500 MHz, DMSO) δ 9.03 (s, 1H), 8.44 (s, 1H), 7.34 (s, 1H), 7.11 (brs, 2H), 3.81-3.75 (m, 4H), 3.74-3.68 (m, 4H), 3.25 (s, 3H), 1.77-1.64 (m, 2H), 1.62-1.58 (m, 2H).

Example 45-46

Compound S-46 was obtained by using compound 1-a as the starting material and referring to the method in Example 1 except that 1a in step 5 was replaced by 3a.
Compound S-45 was obtained by using compound 1-a as the starting material and referring to the method in Example 1 except that 1,2-dibromoethane in step 4 was replaced by methyl iodide, and 1a in step 5 was placed by 3a.

| No. | structure | MS [M + H]+ | ¹HNMR |
|---|---|---|---|
| Example 45 | S-45 | 447 | ¹H NMR (400 MHz, CDCl₃) δ 8.61 (s, 1H), 6.99 (s, 1H), 5.48 (brs, 2H), 3.87-3.81 (m, 4H), 3.81-3.75 (m, 4H), 2.86 (s, 3H), 1.58 (s, 6H). |
| Example 46 | S-46 | 445 | ¹H NMR (400 MHz, CDCl₃) δ 8.60 (s, 1H), 7.09 (s, 1H), 5.48 (brs, 2H), 3.85-3.80 (m, 4H), 3.80-3.74 (m, 4H) 3.07 (s, 3H), 1.88 (q, J = 4.6 Hz, 2H) 1.60-1.58 (m, 2H). |

Example 47 The preparation of 5-(6-(1-(5-methyloxazol-2-yl)cyclopropyl)-2-morpholinopyrimidin-4-yl)-4-(trifluoromethyl)pyridin-2-amine (S-61)

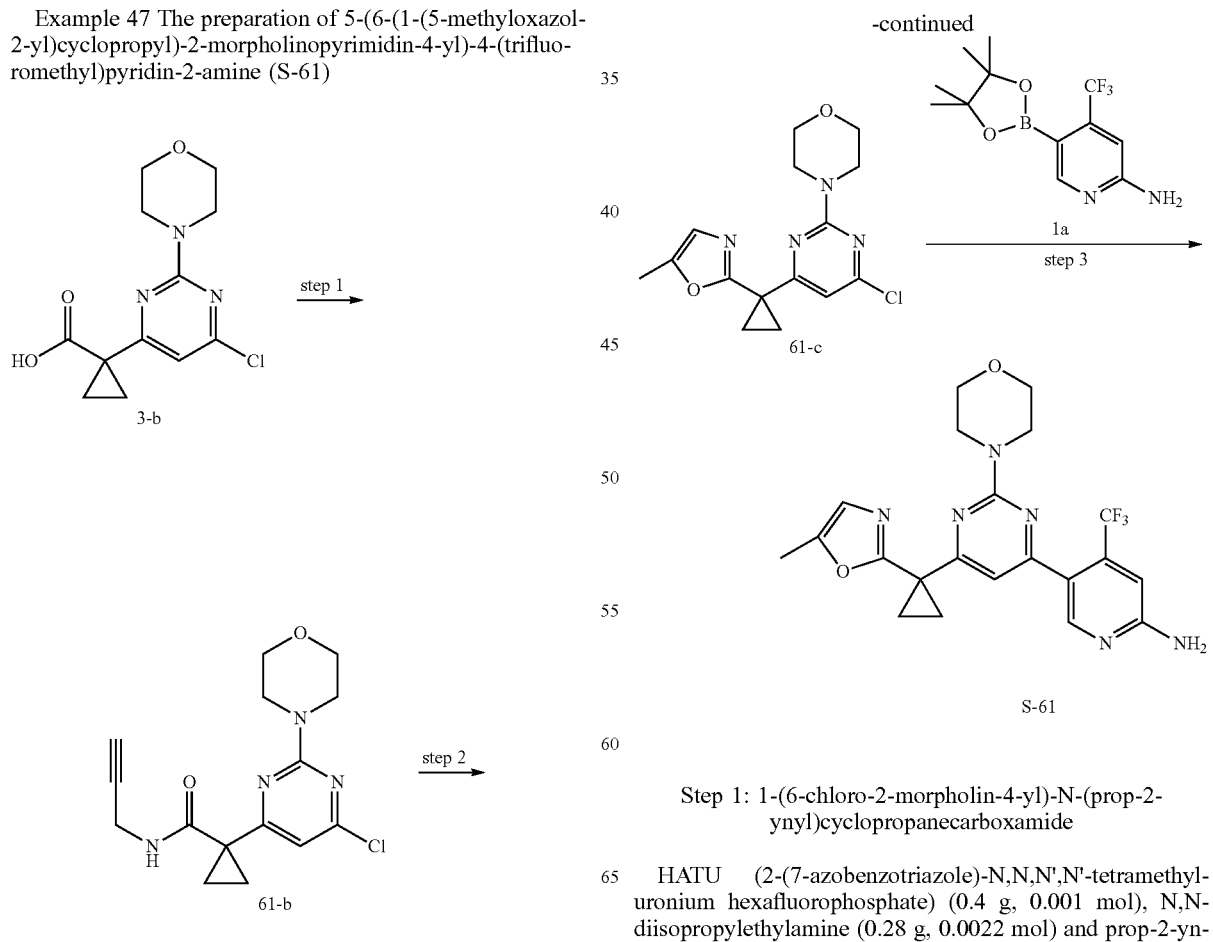

Step 1: 1-(6-chloro-2-morpholin-4-yl)-N-(prop-2-ynyl)cyclopropanecarboxamide

HATU (2-(7-azobenzotriazole)-N,N,N',N'-tetramethyluronium hexafluorophosphate) (0.4 g, 0.001 mol), N,N-diisopropylethylamine (0.28 g, 0.0022 mol) and prop-2-yn- 1-amine (0.048 g, 0.00088 mol) were added to the solution of compound 3-b (0.25 g, 0.00088 mol) in 10 ml of dichloromethane and stirred at room temperature for 2 hours. The reaction was complete, water was added, the organic phase was separated, dried over anhydrous sodium sulfate, filtered and the filtrate was concentrated at below 50° C. under reduced pressure to give compound 61-b (0.28 g) as a pale yellow oil. Purity 83%, spectrum data: MS m/z(ESI): 321.1 [M+H]+.

Step 2: 4-(4-chloro-6-(1-(5-methyloxazol-2-yl)cyclopropyl)pyrimidin-2-yl) morpholine Trifluoromethanesulfonic acid (0.056 g, 0.00037 mol) was added to the solution of compound 61-b (0.12 g, 0.00037 mol) in 4 ml of 1,4-dioxane and stirred at 90° C. for 16 hours. The reaction was complete and the mixture was cooled to room temperature and concentrated under reduced pressure. Dichloromethane and saturated sodium bicarbonate solution were added. The organic phase was separated, dried over anhydrous sodium sulfate and filtered. The filtrate was concentrated under reduced pressure to give the crude product which was purified by Combi-flash column chromatography to give compound 61-c (70 mg) as a yellow oil. Purity: 67%, yield: 58%, spectrum data: MS m/z(ESI): 321.0[M+H]+.

Step 3: 5-(6-(1-(5-methyloxazol-2-yl)cyclopropyl)-2-morpholinopyrimidin-4-yl)-4-(trifluoromethyl)pyridin-2-amine Compound S-61 (14.3 mg) as a white powder was obtained by using compound 61-c (0.07 g) as the starting material and referring to the synthesis method of step 5 in Example 1. Purity: 97.7%, yield: 14.9%. Spectrum data: MS m/z(ESI): 447.3[M+H]+. $^1$H NMR (500 MHz, DMSO) δ 8.15 (s, 1H), 6.88 (brs, 2H), 6.82 (s, 1H), 6.80 (d, J=1.5 Hz, 1H), 6.62 (s, 1H), 3.73-3.61 (m, 8H), 2.28 (d, J=1.2 Hz, 3H), 1.72 (dd, J=7.2, 3.9 Hz, 2H), 1.53 (dd, J=7.2, 3.8 Hz, 2H).

Example 48 The preparation of 5-(6-(1-(ethylsulfonyl)cyclobutyl)-2-morpholino pyrimidin-4-yl)-4-(trifluoromethyl)pyridin-2-amine (S-49)

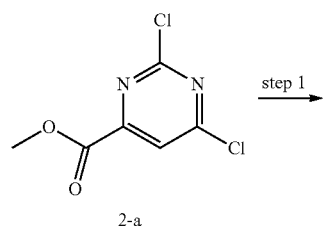
2-a

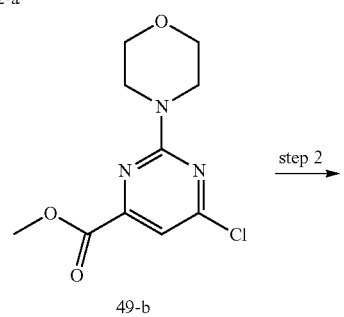
49-b

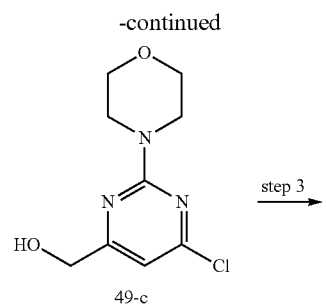
49-c

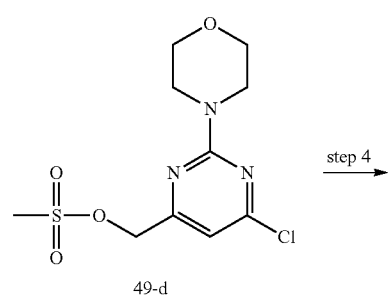
49-d

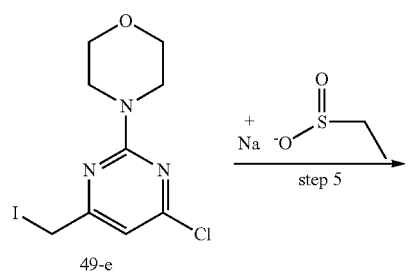
49-e

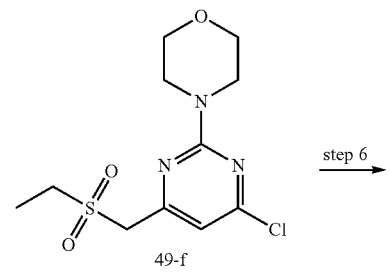
49-f

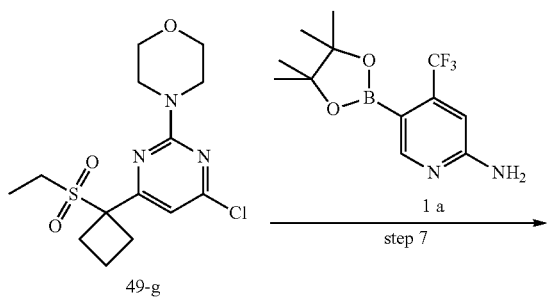
49-g

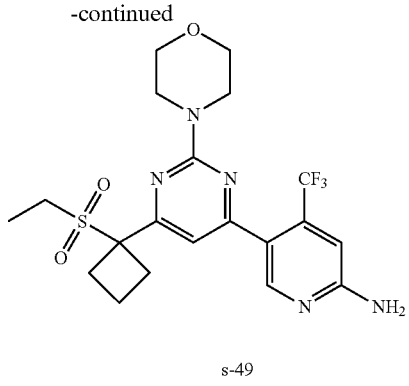

s-49

Step 1: 6-chloro-2-morpholino-4-carboxylic acid

Compound 49-b (2.0 g) as an orange solid was obtained by using compound 2-a (15 g) as the starting material and referring to the synthesis method of Step 1 in Example 27 except that (S)-3-methylmorpholine in the step was replaced by morpholine. Purity: 30.9, yield: 10.6%. Spectrum data: MS m/z(ESI): 258.1 [M+H]+.

Step 2: (6-chloro-2-morpholin-4-yl)methanol

Compound 49-c (1.16 g) as a yellow solid was obtained by using compound 49-b (2.0 g) as the starting material and referring to the synthesis method of Step 2 in Example 27. Purity: 86.8%. Spectrum data: MS m/z(ESI): 230.1[M+H]+.

Step 3: (6-chloro-2-morpholin-4-yl)methylmethanesulfonate

Compound 49-d (1.45 g) as a yellow oil was obtained by using compound 49-c (1.16 g) as the starting material and referring to the synthesis method of Step 2 in Example 26. Purity: 79%. Spectrum data: MS m/z(ESI): 308.0[M+H]+.

Step 4: 4-(4-chloro-6-(iodomethyl)pyrimidin-2-yl)morpholine

Compound 49-e (1.2 g) as an orange solid was obtained by using compound 49-d (1.45 g) as the starting material and referring to the synthesis method of Step 3 in Example 26. Purity: 62.4%. Spectrum data: MS m/z(ESI): 340.0[M+H]+.

Step 5: 4-(4-chloro-6-(ethylsulfonyl)pyrimidin-2-yl)morpholine

Compound 49-f (0.6 g) as a yellow oil was obtained by using compound 49-e (0.9 g) as the starting material and referring to the synthesis method of Step 4 in Example 26 except that sodium methanesulphinate in the step was replaced by sodium ethanesulfinate. Purity: 53%, yield: 74%. Spectrum data: MS m/z(ESI): 306.1 [M+H]+.

Step 6: 4-(4-chloro-6-(1-(ethylsulfonyl)cyclobutyl)pyrimidin-2-yl)morpholine 1,3-dibromopropane (0.049 g, 0.00024 mol), sodium hydroxide (0.28 g) and tetrabutylammonium bromide (0.0052 g, 0.000016 mol) were added to the solution of compound 49-f (0.05 g, 0.00016 mol) in 10 ml of toluene and stirred at 45° C. for 1 hour. The reaction was complete and the mixture was cooled to room temperature, extracted by adding water and ethyl acetate. The organic phase was rinsed with 26% brine and separated, dried over anhydrous sodium sulfate, filtered and the filtrate was concentrated under reduced pressure to give the crude product which was purified by Combi-flash column chromatography to give compound 49-g (20 mg) as a yellow oil. Purity: 40%, yield: 35.3%. Spectrum data: MS m/z(ESI): 346.0[M+H]+.

Step 7: 5-(6-(1-(ethylsulfonyl)cyclobutyl)-2-morpholinopyrimidin-4-yl)-4-(trifluoromethyl)pyridin-2-amine Compound S-49 (3.9 mg) as a white solid was obtained by using compound 49-g (0.02 g) as the starting material and referring to the synthesis method of Step 5 in Example 1. Purity: 100%, yield: 32.5%. Spectrum data: MS m/z(ESI): 472.1[M+H]+. $^1$H NMR (500 MHz, DMSO) δ 8.25 (s, 1H), 6.95 (brs, 2H), 6.94 (s, 1H), 6.86 (s, 1H), 3.77-3.72 (m, 4H), 3.70-3.64 (m, 4H), 2.96-2.86 (m, 4H), 2.80-2.75 (m, 2H), 2.10-2.00 (m, 1H), 1.96-1.87 (m, 1H), 1.12 (t, J=7.4 Hz, 3H).

Example 49 The preparation of 2-(6-(6-amino-4-(trifluoromethyl)pyridin-3-yl)-2-morpholin-4-yl)propan-2-ol (S-50)

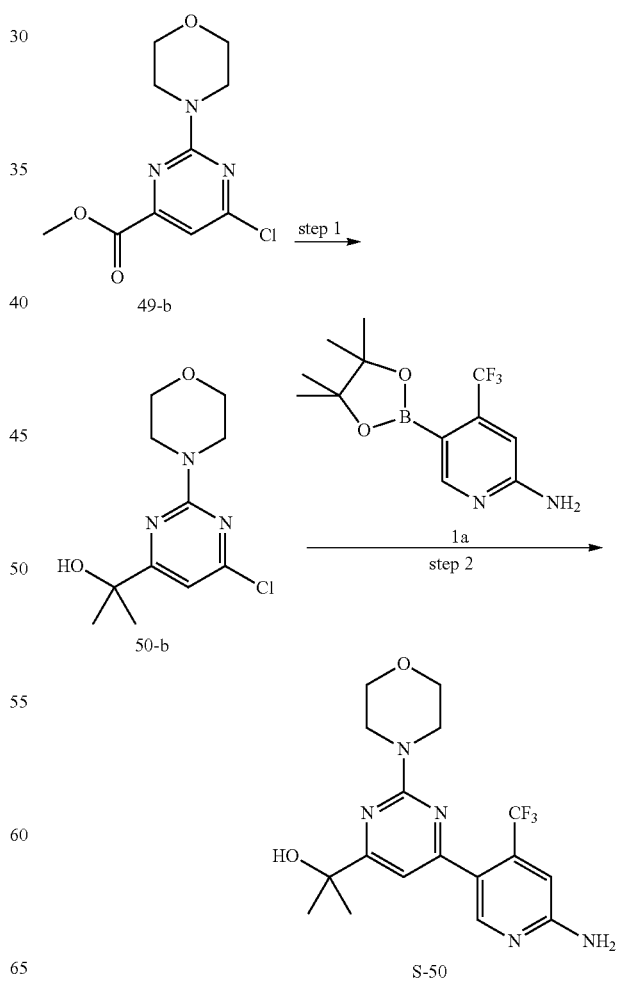

Step 1: 2-(6-chloro-2-morpholin-4-yl)propan-2-ol

Methylmagnesium bromide (0.25 ml, 0.8 mmol) was slowly added to a solution of compound 49-b (50 mg, 0.2 mmol) in 5 ml of tetrahydrofuran at 0° C. and stirred for 4 hours at 0° C. to room temperature under argon. The reaction was complete and the mixture was extracted by adding water and ethyl acetate. The organic phase was rinsed with saturated brine, separated, dried over sodium sulfate, and filtered. The filtrate was concentrated under reduced pressure to give crude compound 50-b (50 mg). Purity: 79%. Spectrum data: MS m/z(ESI): 258[M+H]+.

Step 2: 2-(6-(6-amino-4-(trifluoromethyl)pyridin-3-yl)-2-morpholin-4-yl)propan-2-ol Compound S-50 (30 mg) as a white solid was obtained by using compound 50-b (50 mg) as the starting material and referring to the synthesis method of Step 5 in Example 1. Purity: 97.32%, yield: 40%. Spectrum data: MS m/z(ESI): 384[M+H]+. $^1$H NMR (400 MHz, CDCl$_3$) δ 8.30 (s, 1H), 6.81 (s, 1H), 6.70 (s, 1H), 4.87 (brs, 2H), 4.65 (s, 1H), 3.90-3.83 (m, 4H), 3.82-3.74 (m, 4H), 1.51 (s, 6H).

Example 50 The preparation of 5-(6-(fluoro(methylsulfonyl)methyl)-2-morpholino pyrimidin-4-yl)-4-(trifluoromethyl)pyridin-2-amine (S-52)

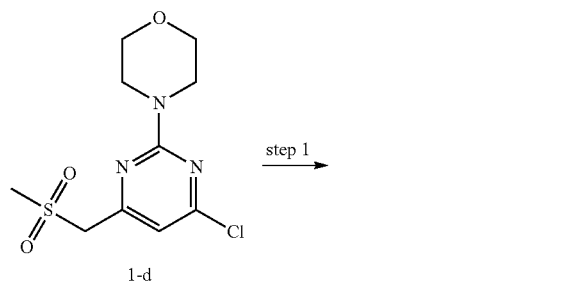

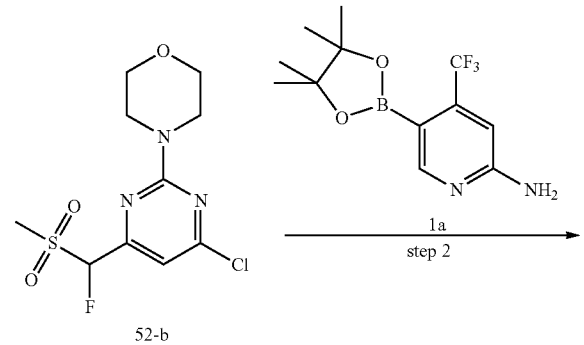

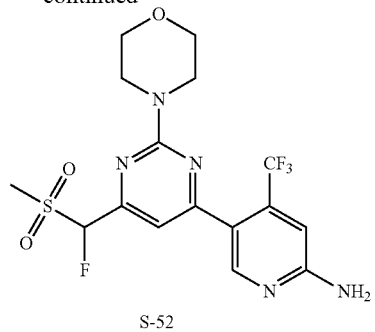

Step 1: 4-(4-chloro-6-(fluoro(methylsulfonyl)methyl)pyrimidin-2-yl)morpholine Sodium bis(trimethylsilyl)amide (2 M in tetrahydrofuran) (0.085 ml, 0.17 mmol) was added to a solution of compound 1-d (50 mg, 0.17 mol) in 10 ml of tetrahydrofuran under argon at −78° C. and stirred for 15 minutes. N-fluorobisbenzenesulfonamide (80 mg, 0.255 mmol) was then added and stirred for 1 h. Sodium bis(trimethylsilyl)amide (80 mg, 0.255 mmol) was added under argon at −78° C. and stirred for 15 minutes. N-fluorobisbenzenesulfonamide (80 mg, 0.255 mmol) was then added and stirred for 1 h. The reaction was complete and the mixture was warmed to room temperature. Saturated ammonium chloride solution was added and the mixture was extracted with ethyl acetate. The organic phase was separated without being rinsed with saturated brine, dried over anhydrous sodium sulfate, filtered and concentrated under reduced pressure to give the crude compound 52-b (23.4 mg), spectrum data: MS m/z(ESI): 310[M+H]+.

Step 2: 5-(6-(fluoro(methylsulfonyl)methyl)-2-morpholinopyrimidin-4-yl)-4-(trifluoromethyl)pyridin-2-amine Compound S-52 (7.16 mg) was obtained by using compound 52-b (60 mg) as the starting material and referring to the synthesis method of step 5 in Example 1. Purity: 100%. Spectrum data: MS m/z(ESI): 436[M+H]+. $^1$H NMR (500 MHz, CDCl$_3$) δ 8.30 (s, 1H), 6.92 (s, 1H), 6.84 (s, 1H), 5.86 (d, J=46.6 Hz, 1H), 5.10 (brs, 2H), 3.90-3.82 (m, 4H), 3.79-3.72 (m, 4H), 3.06 (d, J=1.6 Hz, 3H).

Example 51

Compound S-53 was obtained by using compound 1-d as the starting material and referring to the method in Example 50.

| No. | Structure | MS [M + H]+ | ¹HNMR |
|---|---|---|---|
| Example 51 | S-53 | 454 | ¹H NMR (500 MHz, CDCl₃) δ 8.31 (s, 1H), 7.05 (s, 1H), 6.85 (s, 1H), 5.08 (brs, 2H), 3.90-3.84 (m, 4H), 3.80-3.75 (m, 4H), 3.21 (s, 3H). |

Example 52 The preparation of 4-chloro-5-(6-(difluoro(methylsulfonyl)methyl)-2-morpholinopyrimidin-4-yl)pyridin-2-amine (S-54)

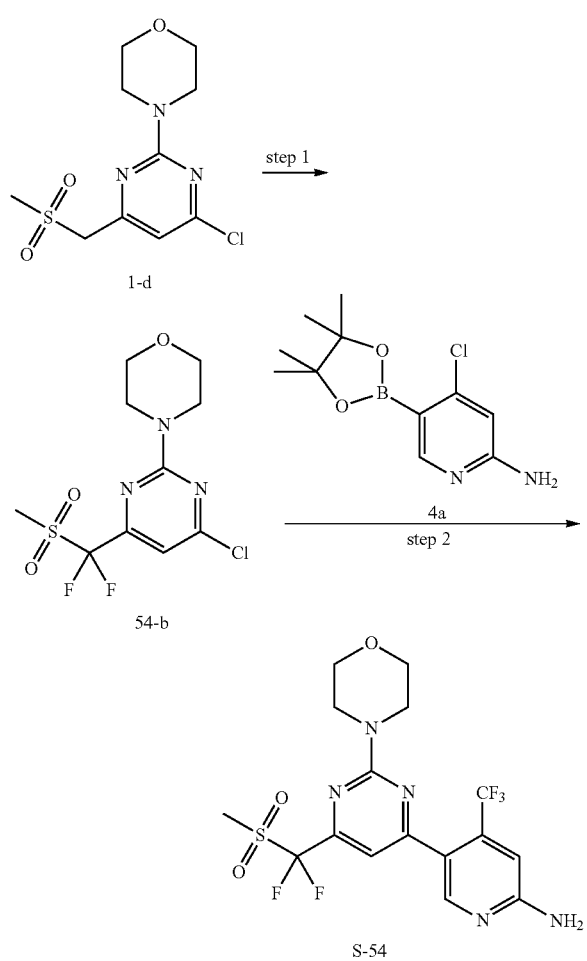

Step 1: 4-(4-chloro-6-(difluoro(methylsulfonyl)methyl)pyrimidin-2-yl)morpholine

Lithium hexamethyldisilazide (1 M in tetrahydrofuran) (0.34 ml, 0.34 mmol) was added to the solution of compound 1-d (50 mg, 0.17 mol) in 5 ml of tetrahydrofuran at 0° C., N-fluorobisbenzenesulfonamide (160 mg, 0.51 mmol) was added dropwise, and stirred at 0° C. for 3 h. The reaction was complete and the mixture was warmed to room temperature, extracted by adding water and ethyl acetate. The organic phase was separated without being rinsed with saturated brine, dried over anhydrous sodium sulfate, filtered and concentrated under reduced pressure to give the crude compound 54-b (56 mg), spectrum data: MS m/z(ESI): 328.0[M+H]+.

Step 2: 4-chloro-5-(6-(difluoro(methylsulfonyl) methyl)-2-morpholinopyrimidin-4-yl) pyridin-2-amine Compound S-54 (6.02 mg) was obtained by using compound 54-b (55 mg) as the starting material and referring to the synthesis method of step 1 in Example 1 except that 1a in the step was replaced by 4a. Purity, spectrum data: MS m/z(ESI): 420.1 [M+H]+. ¹H NMR (500 MHz, CDCl₃) δ 8.41 (s, 1H), 7.31 (s, 1H), 6.64 (s, 1H), 5.07 (brs, 2H), 3.88 (d, J=4.9 Hz, 4H), 3.81-3.76 (m, 4H), 3.21 (s, 3H).

Example 53 The preparation of 4-chloro-5-(2-morpholinyl-6-(2-(phenylsulfonyl)propan-2-yl)pyrimidin-4-yl)pyridin-2-amine (S-55)

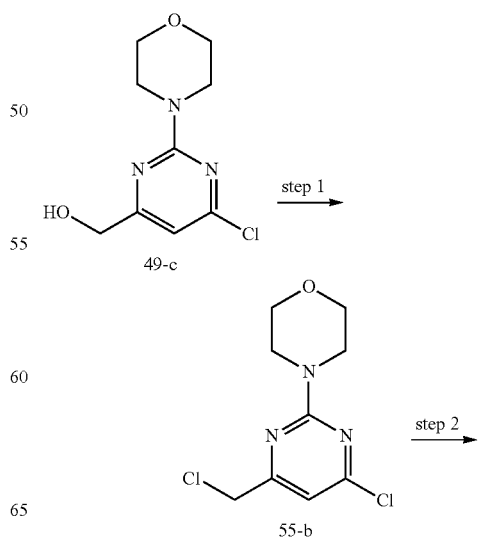

-continued

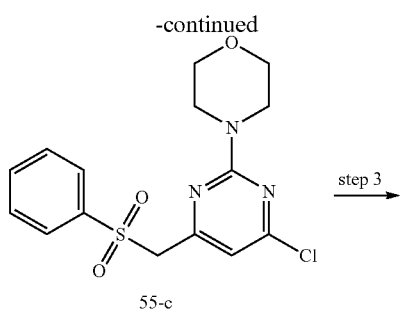

55-c

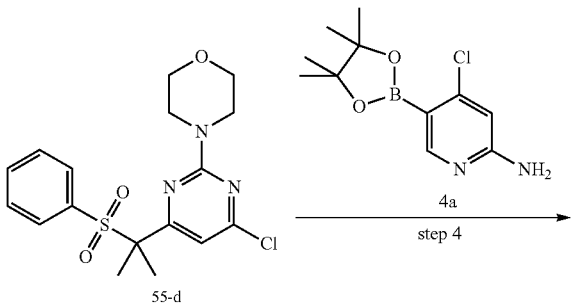

55-d

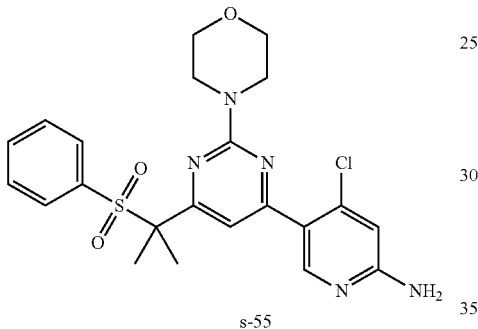

s-55

Step 1: 4-(4-chloro-6-(cloromethyl)pyrimidin-2-yl)morpholine

Thionyl chloride (0.5 ml, 5.5 mmol) was added to the solution of compound 49-c (250 mg, 1.1 mol) in 5 ml of dichloromethane and the mixture was stirred at room temperature for 20 minutes. The reaction was complete and the mixture was concentrated under reduced pressure to give crude compound 55-b (260 mg). Purity: 92%. Spectrum data: MS m/z(ESI): 248[M+H]+.

Step 2: 4-(4-chloro-6-(benzenesulfonylmethyl)pyrimidin-2-yl)morpholine

Compound 55-c (145 mg) was obtained by using compound 55-b (100 mg) as the starting material and referring to the synthesis method of step 4 in Example 26 except that sodium methanesulfinate in the step was replaced by sodium benzenesulfinate. Spectrum data: MS m/z(ESI): 354[M+H]+.

Step 3: 4-(4-chloro-6-(2-(phenylsulfonyl)propan-2-yl)pyrimidin-2-yl)morpholine Compound 55-d (160 mg) was obtained by using compound 55-c (145 mg) as the starting material and referring to the synthesis method of step 4 in Example 1 except that 1,2-dibromoethane in the step was replaced by methyl iodide. Spectrum data: MS m/z(ESI): 382[M+H]+.

Step 4: 4-chloro-5-(2-morpholinyl-6-(2-(phenylsulfonyl)propan-2-yl)pyrimidin-4-yl) pyridin-2-amine Compound S-55 (12.12 mg) was obtained by using compound 55-d (160 mg) as the starting material and referring to the synthesis method of step 5 in Example 1 except that 1a in the step was replaced by 4a. Spectrum data: MS m/z(ESI): 474[M+H]+. $^1$H NMR (400 MHz, DMSO) δ 8.23 (s, 1H), 7.73 (t, J=7.5 I-Hz, 1H), 7.56 (t, J=7.8 Hz, 2H), 7.49 (d, J=8.1 Hz, 2H), 7.12 (s, 1H), 6.77 (brs, 2H), 6.61 (s, 1H), 3.56-3.50 (m, 4H), 3.45-3.41 (m, 4H), 1.72 (s, 6H).

Example 54 The preparation of 5-(6-(2-(1H-indazol-1-yl)propan-2-yl)-2-morpholinopyrimidin-4-yl)-4-(trifluoromethyl)pyridin-2-amine (S-56)

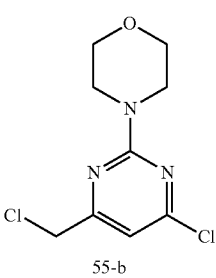

55-b

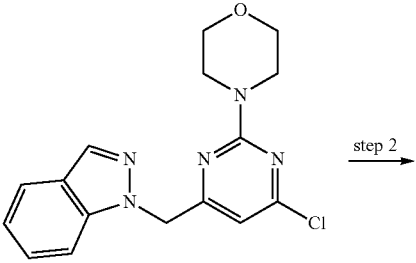

56-b

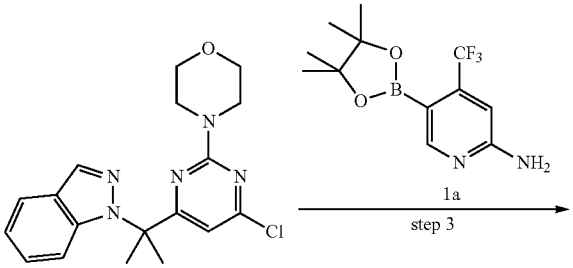

56-c

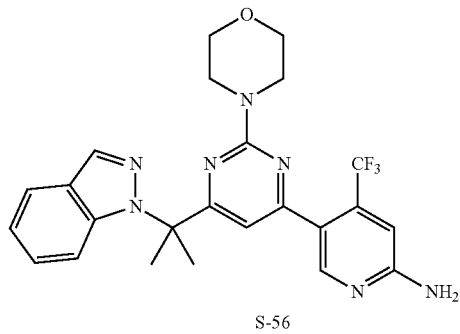

S-56

Step 1: 4-(4-((1H-indazol-1-yl)methyl)-6-chloropyrimidin-2-yl)morpholine 1H-indazole (150 mg, 1.21 mmol) and potassium carbonate (500 mg, 3.65 mmol) were added to the solution of compound 55-b (300 mg, 1.21 mol) in 10 ml of dimethylformamide and stirred at room temperature overnight. The reaction was complete, and the mixture was extracted by adding water and ethyl acetate. The organic phase was rinsed with water and saturated brine, respectively, dried over sodium sulfate and filtered. The filtrate was concentrated under reduced pressure to give crude compound 56-b (400 mg). Purity: 67%. Spectrum data: MS m/z(ESI): 330[M+H]+.

Step 2: 4-(4-(2-(1H-indazol-1-yl)propan-2-yl)-6-chloropyrimidin-2-yl)morpholine Compound 56-c (420 mg) was obtained by using compound 56-b (400 mg) as the starting material and referring to the synthesis method of step 4 in Example 1 except that 1,2-dibromoethane in the step was replaced by methyl iodide. Spectrum data: MS m/z(ESI): 358 [M+H]+.

Step 3: 5-(6-(2-(1H-indazol-1-yl)propan-2-yl)-2-morpholinopyrimidin-4-yl)-4-(trifluoromethyl)pyridin-2-amine Compound S-56 (51 mg) was obtained by using compound 56-c (200 mg) as the starting material and referring to the synthesis method of step 5 in Example 1. Spectrum data: MS m/z(ESI): 484[M+H]+. $^1$H NMR (500 MHz, CDCl$_3$) δ 8.04 (s, 1H), 7.91 (s, 1H), 7.73 (d, J=8.0 Hz, 1H), 7.17 (t, J=7.5 Hz, 1H), 7.09 (t, J=7.4 Hz, 1H), 6.93 (d, J=8.5 Hz, 1H), 6.68 (s, 1H), 6.02 (s, 1H), 4.73 (brs, 21H), 3.94-3.84 (m, 4H), 3.84-3.71 (m, 4H), 2.06 (s, 6H).

Example 55 The preparation of 5-(6-(1-(3-fluorophenylsulfonyl)cyclopropyl)-2-morpholinopyrimidin-4-yl)-4-(trifluoromethyl)pyridin-2-amine (S-57)

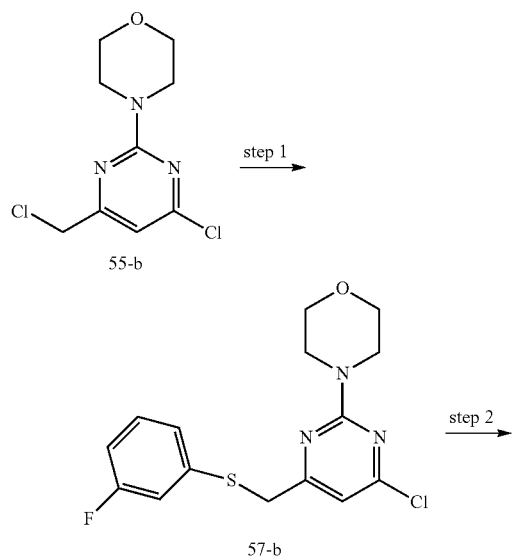

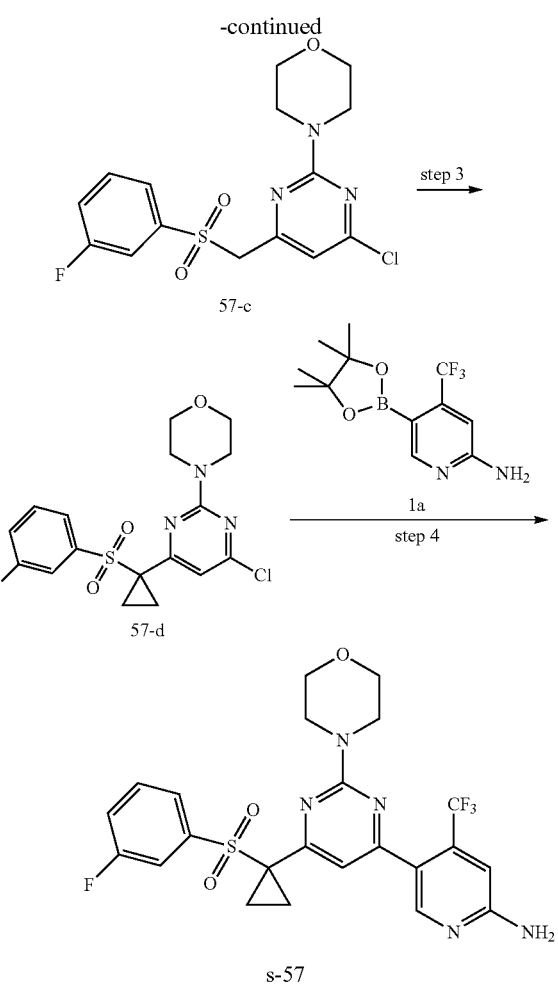

Step 1: 4-(4-chloro-6-((3-fluorophenyl)methyl)pyrimidin-2-yl)morpholine 3-fluorobenzenethiol (120 mg, 0.96 mmol) was added to the solution of potassium tert-butoxide (140 mg, 1.6 mmol) in 10 ml of acetonitrile under argon and the solution of compound 55-b (200 ing, 0.8 mmol) in acetonitrile was added and stirred at room temperature overnight. The reaction was complete and the mixture was extracted by adding water and ethyl acetate. The organic phase was rinsed with saturated sodium bicarbonate, separated, dried over anhydrous sodium sulfate and filtered and the filtrate was concentrated under reduced pressure to give the crude compound 57-b (220 mg). Purity: 71%. Spectrum data: MS m/z(ESI): 340[M+H]+.

Step 2: 4-(4-chloro-6-((3-fluorophenylsulfonyl)methyl)pyrimidin-2-yl)morpholine m-chloroperoxybenzoic acid (410 mg, 2.36 mmol) was added to the solution of compound 57-b (200 mg, 0.59 mmol) in 10 ml of dichloromethane and stirred at room temperature for 2 hours. The reaction was complete and the mixture was extracted by adding water and dichloromethane. The organic phase was rinsed with saturated brine, separated, dried over sodium sulfate, and filtered. The filtrate was concentrated under reduced pressure to give crude compound 57-c (300 mg).

Step 3: 4-(4-chloro-6-(1-(3-fluorophenylsulfonyl)cyclopropyl)pyrimidin-2-yl) morpholine Compound 57-d (320 mg) was obtained by using compound 56-c (200 mg) as the starting material and referring to the synthesis method of step 6 in Example 48 except that 1,3-dibromopropane in the step was replaced by 1,2-dibromoethane. Spectrum data: MS m/z(ESI): 398[M+H]+.

Step 4: 5-(6-(1-(3-fluorophenylsulfonyl)cyclopropyl)-2-morpholinopyrimidin-4-yl)-4-(trifluoromethyl)pyridin-2-amine Compound S-57 (39 mg) was obtained by using compound 57-d (320 mg) as the starting material and referring to the synthesis method of step 5 in Example 1. Spectrum data: MS m/z(ESI): 524[M+H]+. $^1$H NMR (500 MHz, CDCl$_3$) δ 8.20 (s, 1H), 7.53 (d, J=7.9 Hz, 1H), 7.49-7.41 (m, 2H), 7.29 (t, J=7.1 Hz, 1H), 7.06 (s, 1H), 6.80 (s, 1H), 4.87 (brs, 2H), 3.72-3.54 (m, 8H), 2.00-1.97 (m, 2H), 1.63-1.59 (m, 2H).

Examples 56-58

Compounds S-58 and S-59 were prepared by using compound 55-b as the starting material and referring to the method in Example 55 except that 3-fluorobenzenethiol in step 1 was replaced by 2-fluorobenzenethiol and 4-fluorobenzenethiol, respectively.

Compound S-60 was prepared by using compound 55-b as the starting material and referring to the synthesis method in Example 55 except that 1,2-dibromoethane in step 3 was replaced by methyl iodide.

| No. | Structure | MS [M + H]+ | $^1$HNMR |
|---|---|---|---|
| Example 56 | S-58 | 524 | $^1$H NMR (500 MHz, CDCl$_3$) δ 8.13 (s, 1H), 7.79 (t, J = 7.3 Hz, 1H), 7.58 (dd, J = 13.2, 7.2 Hz, 1H), 7.23 (t, J = 7.6 Hz, 1H), 7.18 (t, J = 9.0 Hz, 1H), 6.96 (s, 1H), 6.79 (s, 1H), 4.86 (brs, 2H), 3.68-3.49 (m, 8H), 2.15-2.10 (m, 2H), 1.70-1.62 (m, 2H). |
| Example 57 | S-59 | 524 | $^1$H NMR (500 MHz, CDCl$_3$) δ 8.21 (s, 1H), 7.74 (dd, J = 8.8, 5.1 Hz, 2H), 7.14 (t, J = 8.5 Hz, 2H), 7.09 (s, 1H), 6.81 (s, 1H), 4.87 (brs, 2H), 3.69-3.54 (m, 8H), 1.98 (dd, J = 7.0, 4.5 Hz, 2H), 1.59 (dd, J = 7.0, 4.5 Hz, 2H). |
| Example 58 | S-60 | 526.5 | $^1$H NMR (500 MHz, CDCl$_3$) δ 8.27 (s, 1H), 7.42-7.35 (m, 1H), 7.32-7.27 (m, 2H), 7.24-7.19 (m, 1H), 7.01 (s, 1H), 6.83 (s, 1H), 4.91 (brs, 2H), 3.69-3.40 (m, 8H), 1.83 (s, 6H). |

Example 59 The preparation of 5-(6-(methylsulfonylmethyl)-2-morpholino pyrimidin-4-yl)-4-(trifluoromethyl)pyridin-2-amine (S-62)

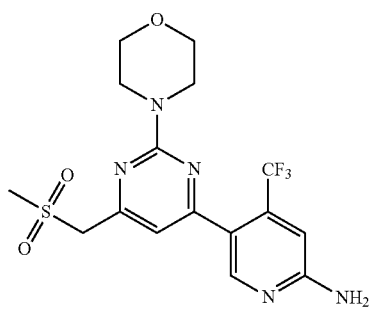

S-62

The title compound was prepared by referring to example 1 except that step 4 in Example 1 was omitted. MS m/z(ESI): 418[M+H]+. $^1$H NMR (500 MHz, CDCl$_3$) δ 8.30 (s, 1H), 6.81 (s, 2H), 4.90 (brs, 2H), 4.24 (s, 2H), 3.86-3.82 (m, 4H), 3.78-3.74 (m, 4H), 3.04 (s, 3H).

Example 60 The preparation of 5-(6-(methylsulfonylmethyl)-2-morpholino pyrimidin-4-yl)-4-(trifluoromethyl)pyridin-2-amine (S-71)

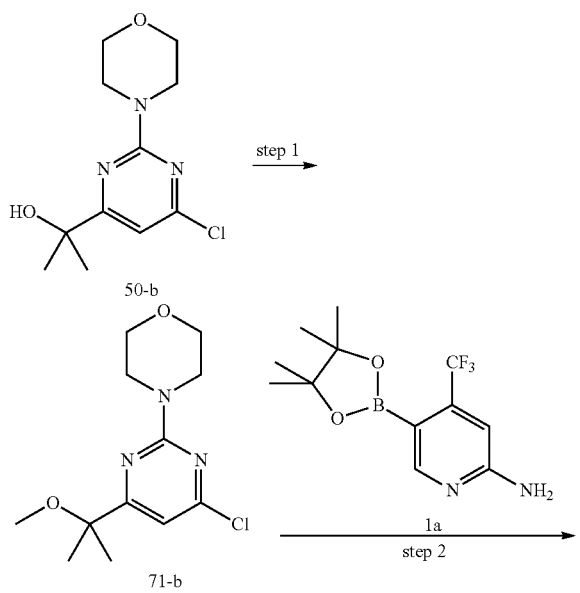

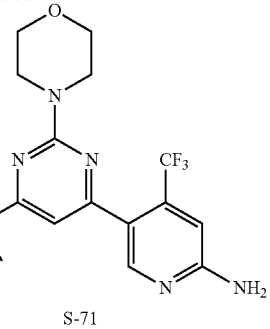

S-71

Step 1: 4-(4-chloro-6-(2-methoxypropan-2-yl)pyrimidin-2-yl)morpholine

Methyl iodide (90 mg, 0.6 mmol) and sodium hydride (30 mg, 0.6 mmol) were added to the solution of compound 50-b (50 mg, 0.2 mmol) in 5 ml of dimethylformamide and stirred at room temperature for 1 h. The reaction was complete and the mixture was extracted by adding water and ethyl acetate. The organic phase was rinsed with water and saturated brine, respectively, dried over sodium sulfate, and filtered. The filtrate was and concentrated under reduced pressure to give crude compound 62-b (60 mg). Purity: 88%, spectrum data: MS m/z(ESI): 272[M+H]+.

Step 2: 5-(6-(2-methoxypropan-2-yl)-2-morpholinopyrimidin-4-yl)-4-(trifluoromethyl) pyridin-2-amine Compound S-71 (12 mg) as a white solid was obtained by using compound 62-b (50 mg) as the starting material and referring to the synthesis method of step 5 in Example 1. Purity: 100%, yield: 16%. Spectrum data: MS m/z(ESI): 398[M+H]+. 1H NM R (500 MHz, CDCl3) δ8.31 (s, 1H), 6.92 (s, 1H), 6.80 (s, 1H), 4.85 (s, 2H), 3.87-3.81 (m, 4H), 3.80-3.74 (m, 4H), 3.21 (s, 3H), 1.50 (s, 6H).

Examples 61-64

The compounds in Examples 61-64 may be prepared in a manner similar to the preparation method of compound S-50 based on raw materials having different substituents. These raw materials are either commercially available or can be obtained according to the preparation methods well known to those skilled in the art.

| No. | structure | MS [M + H]$^+$ | $^1$HNMR |
|---|---|---|---|
| Example 61 | S-63 | 350.1 | $^1$H NMR (500 MHz, CDCl$_3$) δ 8.40 (s, 1H), 6.92 (s, 1H), 6.59 (s, 1H), 4.72 (s, 1H), 4.68 (s, 2H), 3.82-3.77 (m, 4H), 3.91-3.86 (m, 4H), 1.51 (s, 6H). |

| No. | structure | MS [M + H]+ | 1HNMR |
|---|---|---|---|
| Example 62 | 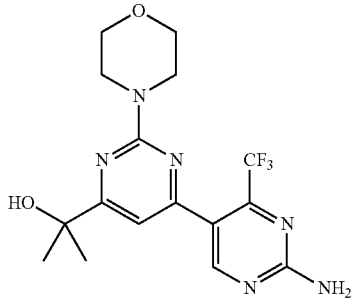<br>S-64 | 385.1 | 1H NMR (500 MHz, CDCl3) δ 8.61 (s, 1H), 6.69 (s, 1H), 5.47 (s, 2H), 4.52 (s, 1H), 3.90-3.84 (m, 4H), 3.82-3.75 (m, 4H), 1.51 (s, 6H). |
| Example 63 | 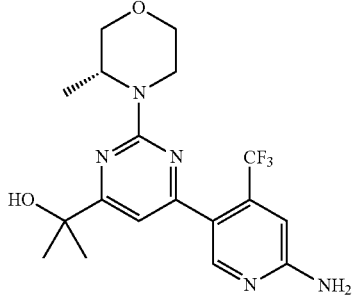<br>S-72 | 398.2 | 1H NMR (500 MHz, DMSO) δ 8.19 (s, 1H), 7.01 (s, 1H), 6.87 (s, 2H), 6.85 (s, 1H), 5.22 (s, 1H), 4.63 (d, J = 4.1 Hz, 1H), 4.29 (d, J = 12.2 Hz, 1H), 3.95-3.86 (m, 1H), 3.71 (d, J = 11.3 Hz, 1H), 3.58 (dd, J = 11.4, 3.0 Hz, 1H), 3.42 (t, J = 10.4 Hz, 1H), 3.15-3.09 (m, 1H), 1.41 (s, 6H), 1.17 (d, J = 6.7 Hz, 3H). |
| Example 64 | 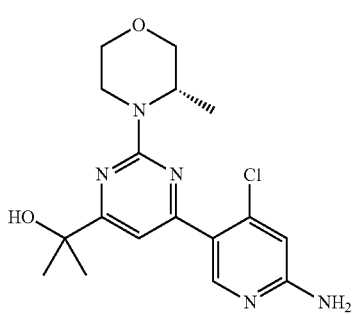<br>S-73 | 364.2 | 1H NMR (500 MHz, CDCl3) δ 8.41 (s, 1H), 6.91 (s, 1H), 6.60 (s, 1H), 4.80-4.78 (m, 2H), 4.74 (brs, 2H), 4.44 (d, J = 13.0 Hz, 1H), 4.01 (d, J = 10.9 Hz, 1H), 3.80 (d, J = 11 Hz, 1H), 3.73 (d, J = 12 Hz, 1H), 3.61-3.56 (m, 1H), 3.35-3.31 (m, 1H), 1.52 (s, 6H), , 1.34 (d, J = 6.7 Hz, 3H). |

Examples 65-67

The compounds in Examples 65-67 may be prepared in a manner similar to the preparation method of compound S-71 based on raw materials having different substituents. These raw materials are either commercially available or can be obtained according to the preparation methods well known to those skilled in the art.

| No. | structure | MS [M + H]+ | 1HNMR |
|---|---|---|---|
| Example 65 | S-74 | 412.2 | 1H NMR (500 MHz, DMSO) δ 8.21 (s, 1H), 6.88 (s, 2H), 6.85 (s, 1H), 6.84 (s, 1H), 4.62 (s, 1H), 4.29 (d, J = 12.7 Hz, 1H), 3.92 (d, J = 8.2 Hz, 1H), 3.71 (d, J = 11.3 Hz, 1H), 3.59 (d, J = 8.4 Hz, 1H), 3.43 (t, J = 10.4 Hz, 1H), 3.15 (d, J = 12.9 Hz, 1H), 3.12 (s, 3H), 1.43 (s, 6H), 1.18 (d, J = 6.7 Hz, 3H). |
| Example 66 | S-75 | 378.2 | 1H NMR (500 MHz, CDCl3) δ 8.41 (s, 1H), 7.12 (s, 1H), 6.59 (s, 1H), 4.79-4.75 (m, 1H), 4.64 (brs, 2H), 4.43 (dd, J = 13.6 Hz, 2.0 Hz, 1H), 3.99 (dd, J = 11.2, 3.4 Hz, 1H), 3.80-3.72 (m, 2H), 3.61-3.55 (m, 1H), 3.32-3.19 (m, 1H), 3.23(s, 3H), 1.50 (s, 6H), , 1.30 (d, J = 6.8 Hz, 3H). |
| Example 67 | S-76 | 364.2 | 1H NMR (500 MHz, CDCl3) δ 8.40 (s, 1H), 7.14 (s, 1H), 6.59 (s, 1H), 4.65 (s, 2H), 3.90-3.83 (m, 4H), 3.82-3.76 (m, 4H), 3.22 (s, 3H), 1.51 (s, 6H). |

Examples 68-75

The compounds in Examples 68-75 may be prepared in a manner similar to the preparation method of compound S-57 based on raw materials having different substituents. These raw materials are either commercially available or can be obtained according to the preparation methods well known to those skilled in the art.

| No. | structure | MS [M + H]+ | 1HNMR |
|---|---|---|---|
| Example 68 | S-65 | 526.1 | 1H NMR (500 MHz, CDCl3) δ 8.20 (s, 1H), 7.54-7.50 (m, 1H), 7.48-7.45 (m, 1H), 7.12 (t, J = 7.7 Hz, 1H), 7.02 (t, J = 12.8 Hz, 1H), 6.93 (s, 1H), 6.76 (s, 1H), 4.85 (brs, 2H), 3.54-3.42 (m, 8H), 1.79 (s, 6H). |

| No. | structure | MS [M + H]+ | 1HNMR |
|---|---|---|---|
| Example 69 | S-69 | 526.2 | 1H NMR (500 MHz, DMSO) δ 8.17 (s, 1H), 7.48 (m, 2H), 7.40 (t, J = 8.4 Hz, 2H), 7.01 (s, 1H), 6.96 (s, 1H), 6.87 (s, 1H), 3.53-3.36 (m, 8H), 1.74 (s, 6H). |
| Example 70 | S-70 | 492.1 | 1H NMR (500 MHz, DMSO) δ 8.23 (s, 1H), 7.71-7.57 (m, 2H), 7.38-7.36 (m, 1H), 7.25 (d, J = 8.3 Hz, 1H), 7.14 (s, 1H), 6.75 (s, 1H), 6.60 (s, 1H), 3.72-3.45 (m, 8H), 1.74 (s, 6H). |
| Example 71 | S-79 | 544.1 | 1H NMR (500 MHz, DMSO) δ 8.18 (s, 1H), 7.68 (dd, J = 18.0, 8.5 Hz. 1H), 7.45-7.36 (m, 2H), 7.03 (s, 1H), 6.98 (s, 2H), 6.87 (s, 1H), 3.54-3.45 (m, 8H), 1.75 (s, 6H). |
| Example 72 | S-80 | 541.8 | 1H NMR (500 MHz, DMSO) δ 8.17 (s, 1H), 7.75-7.70 (m, 2H), 7.62 (d, J = 7.5 Hz, 1H), 7.52 (m, 1H), 7.07 (s, 1H), 6.96 (s, 2H), 6.87 (s, 1H), 3.50-3.35 (m, 8H), 1.78 (s, 6H). |

| No. | structure | MS [M + H]+ | 1HNMR |
|---|---|---|---|
| Example 73 | S-66 | 490.1 | ¹H NMR (500 MHz, CDCl₃) δ 8.28 (s, 1H), 7.83 (t, J = 6.5 Hz, 1H), 7.60-7.55 (m, 1H), 7.28-7.12 (m, 3H), 6.56 (s, 1H), 4.69 (brs, 2H), 3.65-3.40 (m, 8H), 2.15-2.13 (m, 2H), 1.72-1.59 (m, 2H). |
| Example 74 | S-77 | 542.1 | ¹H NMR (500 MHz, DMSO) δ 8.14 (s, 1H), 7.94-7.90(m, 1H), 7.73-7.66 (m, 2H), 6.97 (s, 2H), 6.87 (s, 1H), 6.84 (s, 1H), 3.55-3.48 (m, 8H), 1.94 (m, 2H), 1.64 (m, 2H). |
| Example 75 | S-78 | 539.8 | ¹H NMR (500 MHz, DMSO) δ 8.08 (s, 1H), 7.89 (d, J = 7.7 Hz, 1H), 7.69 (d, J = 3.7 Hz, 2H), 7.52-7.49 (m, 1H), 6.95 (s, 2H), 6.83 (d, J = 5.1 Hz, 2H), 3.49-3.40 (m, 8H), 1.98-1.95 (m, 2H), 1.75-1.72 (m, 2H). |

Examples 76-77

The compounds in Examples 76-77 may be prepared in a manner similar to the preparation method of compound S-24 based on raw materials having different substituents. These raw materials are either commercially available or can be obtained according to the preparation methods well known to those skilled in the art.

| No. | structure | MS [M + H]+ | 1HNMR |
|---|---|---|---|
| Example 76 | S-89 | 409.2 | 1H NMR (400 MHz, DMSO) δ 8.70 (d, J = 11.7 Hz, 1H), 8.31 (s, 1H), 7.31 (s, 1H), 6.79 (s, 2H), 6.26 (d, J = 14.3 Hz, 1H), 3.67 (d, J = 5.1 Hz, 8H), 2.92 (s, 3H), 1.53-1.50 (m, 2H), 1.42-1.35 (m, 2H). |
| Example 77 | S-90 | 425.2 | 1H NMR (400 MHz, DMSO) δ 8.22 (s, 1H), 7.25 (s, 1H), 6.64 (s, 2H), 6.58 (s, 1H), 6.11 (s, 1H), 3.66 (d, J = 5.9 Hz, 8H), 2.93 (s. 3H), 1.51 (s, 2H), 1.40 (d, J = 3.2 Hz, 2H). |

Examples 78-87

The compounds in Examples 78-87 may be prepared in a manner similar to the preparation method of compound S-13 based on raw materials having different substituents. These raw materials are either commercially available or can be obtained according to the preparation methods well known to those skilled in the art.

| No. | structure | MS [M + H]+ | 1HNMR |
|---|---|---|---|
| Example 78 | S-67 | 426.2 | 1H NMR (500 MHz, DMSO) δ 8.28 (s, 1H), 7.14 (s, 1H), 6.72 (s, 2H), 6.59 (s, 1H), 4.66 (d, J = 4.2 Hz, 1H), 4.33 (d, J = 11.8 Hz, 1H), 3.94 (d, J = 8.2 Hz, 1H), 3.74 (d, J = 11.4 Hz, 1H), 3.64-3.58 (m, 1H), 3.46 (t, J = 10.4 Hz, 1H), 3.24-3.15 (m, 1H), 2.97 (s, 3H), 1.72 (s, 6H), 1.22 (d, J = 6.7 Hz, 3H). |
| Example 79 | S-68 | 424.2 | 1H NMR (500 MHz, DMSO) δ 8.28 (s, 1H), 7.13 (s, 1H), 6.72 (s, 2H), 6.58 (s, 1H), 4.62 (d, J = 4.4 Hz, 1H), 4.29 (d, J = 12.8 Hz, 1H), 3.96-3.90 (m, 1H), 3.73 (d, J = 11.3 Hz, 1H), 3.60 (dd, J = 11.4, 2.9 Hz, 1H), 3.48-3.43 (m, 1H), 3.22 (s, 3H), 3.20-3.16 (m, 1H), 1.71-1.64 (m, 2H), 1.61-1.52 (m, 2H), 1.22 (d, J = 6.7 Hz, 3H). |

| No. | structure | MS [M + H]+ | 1HNMR |
|---|---|---|---|
| Example 80 | S-81 | 396.1 | 1H NMR (500 MHz, CDCl3) δ 8.84 (d, J = 10.9 Hz, 1H), 7.24 (s, 1H), 6.21 (d, J = 13.0 Hz, 1H), 4.84 (s, 2H), 3.90-3.83 (m, 4H), 3.82-3.75 (m, 4H), 2.89 (s, 3H), 1.83 (s, 6H). |
| Example 81 | S-82 | 394.1 | 1H NMR (500 MHz, CDCl3) δ 8.85 (d, J = 10.8 Hz, 1H), 7.30 (s, 1H), 6.22 (d, J = 12.9 Hz, 1H), 4.80 (s, 2H), 3.86-3.84 (m, 4H), 3.80-3.78 (m, 4H), 3.10 (s, 3H), 1.85 (q, J = 5.0 Hz, 2H), 1.54 (q, J = 5.0 Hz, 2H). |
| Example 82 | S-83 | 408.2 | 1H NMR (500 MHz, CDCl3) δ 8.85 (d, J = 10.9 Hz, 1H), 7.28 (d, J = 1.4 Hz, 1H), 6.22 (d, J = 13.0 Hz, 1H), 4.85 (s, 2H), 4.76-7.72 (m, 1H), 4.40 (d, J = 11.7 Hz, 1H), 4.00 (dd, J = 11.3, 3.3 Hz, 1H), 3.80 (d, J = 11.4 Hz, 1H), 3.72 (dd, J = 11.4, 3.0 Hz, 1H), 3.57 (td, J = 12.0, 2.9 Hz, 1H), 3.28 (td, J = 13.1, 3.8 Hz, 1H), 3.09 (s, 3H), 1.84 (q, J = 4.5 Hz, 2H), 1.53 (q, J = 5.7 Hz, 2H), 1.30 (d, J = 6.8 Hz, 3H). |
| Example 83 | S-84 | 410.3 | 1H NMR (500 MHz, CDCl3) δ 8.86 (d, J = 10.9 Hz, 1H), 7.23 (d, J = 1.2 Hz, 1H), 6.22 (d, J = 13.0 Hz, 1H), 4.80 (s, 2H), 4.76-4.67 (m, 1H), 4.41 (d, J = 13.2 Hz, 1H), 4.01 (dd, J = 11.3, 3.5 Hz, 1H), 3.81 (d, J = 11.4 Hz, 1H), 3.73 (dd, J = 11.4, 3.0 Hz, 1H), 3.58 (td, J = 12.0, 3.0 Hz, 1H), 3.30 (td, J = 13.0, 3.8 Hz, 1H), 2.88 (s, 3H), 1.83 (s, 6H), 1.31 (d, J = 7.0 Hz, 3H). |

| No. | structure | MS [M + H]⁺ | ¹HNMR |
|---|---|---|---|
| Example 84 | S-85 | 408.2 | ¹H NMR (500 MHz, CDCl₃) δ 8.84 (d, J = 10.9 Hz, 1H), 7.35 (d, J = 1.6 Hz, 1H), 6.22 (d, J = 12.9 Hz, 1H), 4.81 (s, 2H), 3.85-3.83 (m, 4H), 3.80-3.77 (m, 4H), 3.22 (q, J = 7.5 Hz, 2H), 1.81 (q, J = 4.6 Hz, 2H), 1.52 (q, J = 4.7 Hz, 2H), 1.41 (t, J = 7.5 Hz, 3H). |
| Example 85 | S-86 | 422.2 | ¹H NMR (500 MHz, CDCl₃) δ 8.84 (d, J = 10.8 Hz, 1H), 7.42 (d, J = 1.7 Hz, 1H), 6.22 (d, J = 12.9 Hz, 1H), 4.80 (s, 2H), 3.85-3.83 (m, 4H), 3.79-3.77 (m, 4H), 3.47-3.41 (m, 1H), 1.80 (q, J = 4.6 Hz, 2H), 1.53 (q, J = 4.7 Hz, 2H), 1.39 (d, J = 6.9 Hz, 6H). |
| Example 86 | S-87 | 436.2 | ¹H NMR (500 MHz, DMSO) δ 8.29 (s, 1H), 7.26 (s, 1H), 6.71 (s, 2H), 6.58 (s, 1H), 3.78-3.71 (m, 4H), 3.72-3.65 (m, 4H), 2.94-2.85 (m, 1H), 1.67-1.64 (m, 2H), 1.59-1.57 (m, 2H), 1.04-0.98 (m, 2H), 0.97-0.93 (m, 2H). |
| Example 87 | S-88 | 420.1 | ¹H NMR (500 MHz, CDCl₃) δ 8.85 (d, J = 10.9 Hz, 1H), 7.44 (d, J = 1.8 Hz, 1H), 6.22 (d, J = 12.9 Hz, 1H), 4.81 (s, 2H), 3.85-3.83 (m, 4H), 3.80-3.77 (m, 4H), 2.65-2.60 (m, 1H), 1.81 (q, J = 4.5 Hz, 2H), 1.56 (q, J = 5.0 Hz, 2H), 1.21-1.14 (m, 2H), 0.99-0.92 (m, 2H). |

Example 88 The Preparation of Compound S-10 Hydrochloride 230 mg of the free alkali sample was weighed and loaded into a 20 mL glass vial, and 3 mL of acetone was added. The sample was dissolved by sonication to form a clear solution. The hydrochloric acid solution (1 mol/L, 536 μL) was slowly added dropwise with stirring at 50° C. and reacted for 2 h. After 2 h, the mixture was slowly cool to 0° C. and incubated at 0° C. for 2 h. The mixture was subjected to vacuum filtration to separate the solid which was rinsed with acetone 3-5 times and dried at 60° C. in vacuum overnight. The solid product was obtained and the yield was 64.3%. The acid-to-base molar ratio of the obtained salt is 1:1 and the melting point is 261° C.-265° C.

Example 89 The Preparation of Compound S-16 Sulfate 218 mg of the free alkali sample was weighed and loaded into a 20 mL glass vial, and 3 mL of acetone was added. The sample was dissolved by sonication to form a clear solution. The sulfuric acid solution (0.5 mol/L, 536 µL) was slowly added dropwise with stirring at 50° C. and reacted for 2 h. After 2 h, the mixture was slowly cool to 0° C. and incubated at 0° C. for 2 h. The mixture was subjected to vacuum filtration to separate the solid which was rinsed with acetone 3-5 times and dried at 60° C. in vacuum overnight. The solid product was obtained and the yield was 84.8%. The acid-to-base molar ratio of the obtained salt is 2:1 and the melting point is 261° C.-265° C.

Example 90 the Preparation of Compound S-19 Maleate 237 mg of the free alkali sample was weighed and loaded into a 20 mL glass vial, and 3 mL of acetone was added. The sample was dissolved by sonication to form a clear solution. The maleic acid solution (1 mol/L, 536 µL) was slowly added dropwise with stirring at 50° C. and reacted for 2 h. After 2 h, the mixture was slowly cool to 0° C. and incubated at 0° C. for 2 h. The mixture was subjected to vacuum filtration to separate the solid which was rinsed with acetone 3-5 times and dried at 60° C. in vacuum overnight. The solid product was obtained and the yield was 89.6%. The acid-to-base molar ratio of the obtained salt is 1:1 and the melting point is 205° C.-207° C.

Example 91 The Preparation of Compound S-21 Fumarate 248 mg of the free alkali sample was weighed and loaded into a 20 mL glass vial, and 3 mL of acetone was added. The sample was dissolved by sonication to form a clear solution. The aqueous solution of fumaric acid in DMSO (0.25 mol/L, 536 µL) was slowly added dropwise with stirring at 50° C. and reacted for 2 h, wherein the volume ratio of DMSO and water in the solution was 1:1. After 2 h, the mixture was slowly cool to 0° C. and incubated at 0° C. for 2 h. The mixture was subjected to vacuum filtration to separate the solid which was rinsed with acetone 3-5 times and dried at 60° C. in vacuum overnight. The solid product was obtained and the yield was 79.0%. The acid-to-base molar ratio of the obtained salt is 2:1 and the melting point is 234° C.-236° C.

Example 92 The Preparation of Compound S-58 Mesylate 128 mg of the free alkali sample was weighed and loaded into a 20 mL glass vial, and 2 mL of acetone was added. The sample was dissolved by sonication to form a clear solution. The aqueous methanesulfonic acid solution (1 mol/L, 268 µL) was slowly added dropwise with stirring at 50° C. and reacted for 1 h. After 1 h, the mixture was slowly cool to 0° C. and incubated at 0° C. for 1 h. The mixture was subjected to vacuum filtration to separate the solid which was rinsed with acetone 3-5 times and dried at 60° C. in vacuum for 4 h. The solid product was obtained. The acid-to-base molar ratio of the obtained salt is 0.9:1 and the melting point is 248° C.-249° C.

Example 93 the Preparation of Compound S-82 L-Tartrate 96 mg of the free alkali sample was weighed and loaded into a 20 mL glass vial, and 2 mL of acetone was added. The sample was dissolved by sonication to form a clear solution. The aqueous L-tartaric acid solution (1 mol/L, 268 µL) was slowly added dropwise with stirring at 50° C. and reacted for 1 h. After 1 h, the mixture was slowly cool to 0° C. and incubated at 0° C. for 1 h. The mixture was subjected to vacuum filtration to separate the solid which was rinsed with acetone 3-5 times and dried at 60° C. in vacuum for 4 h. The solid product was obtained. The acid-to-base molar ratio of the obtained salt is 2:1 and the melting point is 196° C.-198° C.

Comparative example 1 The preparation of 4-(1-(methylsulfonyl)cyclopropyl)-6-morpholino-4'-(trifluoromethyl)-2,3'bipyridyl-6'-amine (Comparative compound 1)

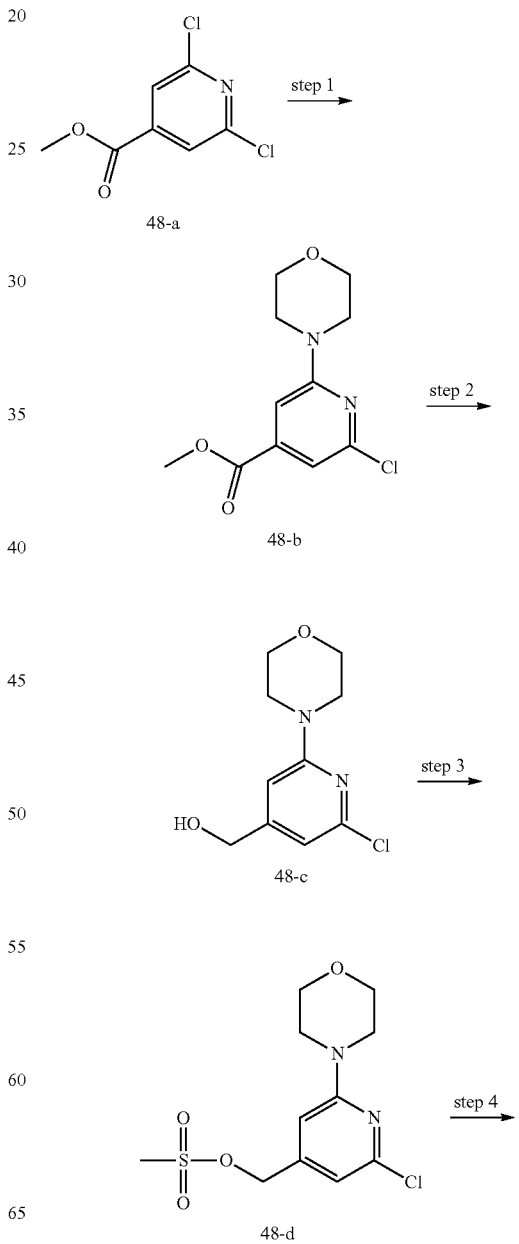

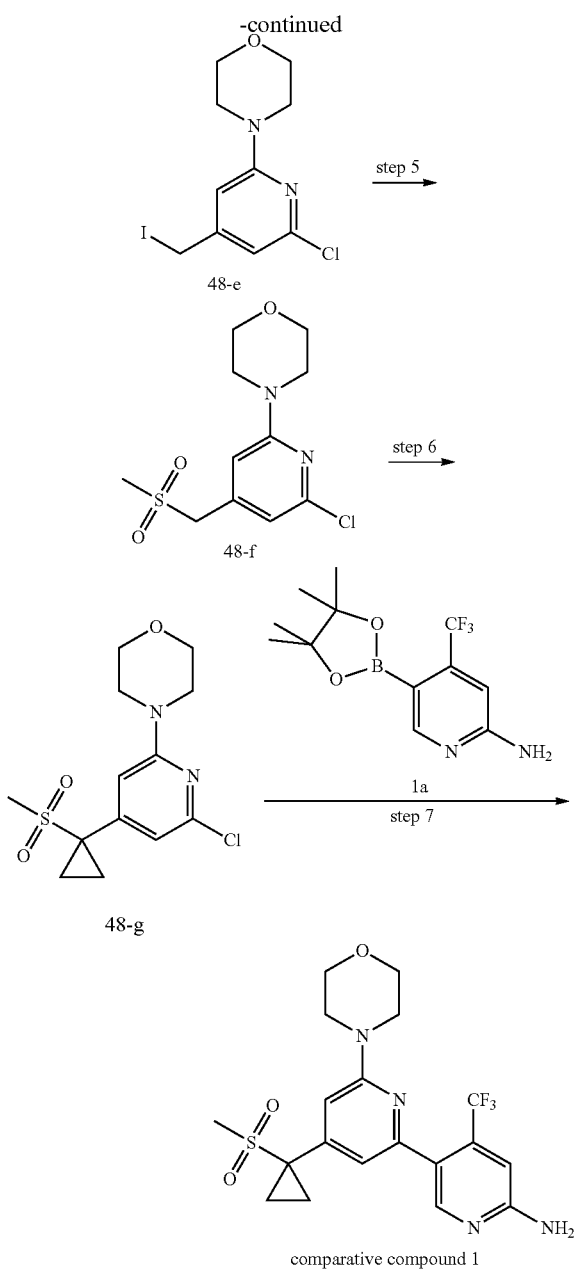

synthesis method of step 2 in Example 27. Purity: 73%. Spectrum data: MS m/z(ESI): 229[M+H]+.

Step 3: (2-chloro-6-morpholinopyridin-4-yl)methyl-methanesulfonate

Compound 48-d (1.5 g) was prepared by using compound 48-c (1.0 g) as the starting material and referring to the synthesis method of step 2 in Example 26. Purity: 86%. Spectrum data: MS m/z(ESI): 307[M+H]+.

Step 4: 4-(6-chloro-4-(iodomethyl)pyridin-2-yl)morpholine

Compound 48-e (1.0 g) was prepared by using compound 48-d (1.5 g) as the starting material and referring to the synthesis method of step 3 in Example 26. Purity: 76%. Spectrum data: MS m/z(ESI): 339[M+H]+.

Step 5: 4-(6-chloro-4-(methylsulfonylmethyl)pyridin-2-yl)morpholine

Compound 48-f (110 mg) was prepared by using compound 48-e (1.5 g) as the starting material and referring to the synthesis method of step 4 in Example 26. Purity: 71%. Spectrum data: MS m/z(ESI): 291 [M+H]+.

Step 6: 4-(6-chloro-4-(1-(methylsulfonyl)cyclopropyl)pyridin-2-yl)morpholine

Compound 48-g (70 mg) was prepared by using compound 48-f (50 mg) as the starting material and referring to the synthesis method of step 4 in Example 1.

Step 7: 4-(1-(methylsulfonyl)cyclopropyl)-6-morpholino-4'-(trifluoromethyl)-2,3'bipyridyl-6'-amine Comparative compound 1 (21.3 mg) as a white solid compound was prepared by using compound 48-g (60 mg) as the starting material and referring to the synthesis method of step 5 in Example 1. Purity: 97%, yield: 20%. Spectrum data: MS m/z(ESI): 443[M+H]+. ¹H NMR (500 MHz, CDCl₃) δ 8.26 (s, 1H), 6.86 (s, 1H), 6.84 (s, 1H), 6.79 (s, 1H), 4.78 (brs, 2H), 3.88-3.75 (m, 4H), 3.62-3.51 (m, 4H), 2.82 (s, 3H), 1.85-1.81 (m, 2H), 1.32-1.28 (m, 2H).

Step 1: morpholine (430 mg, 4.88 mmol) and potassium carbonate (1.35 g, 9.76 mmol) were added to the solution of compound 48-a (1 g, 4.88 mmol) in 20 ml of acetonitrile and stirred at 80° C. overnight. The reaction was complete and the mixture was cooled to room temperature, concentrated under reduced pressure, and extracted by adding water and ethyl acetate. The organic phase was separated, rinsed with saturated brine, dried over sodium sulfate, and filtered. The filtrate was concentrated under reduced pressure to give crude compound 48-b (1.2 g). Spectrum data: MS m/z(ESI): 257[M+H]+.

Step 2: (2-chloro-6-morpholinopyridin-4-yl)methanol

Compound 48-c (1.0 g) was prepared by using compound 48-b (1.2 g) as the starting material and referring to the Comparative example 2 The preparation of 5-(4-(1-(methylsulfonyl)cyclopropyl)-6-morpholinopyridin-2-yl)-4-(trifluoromethyl)pyridin-2-amine (Comparative compound 2)

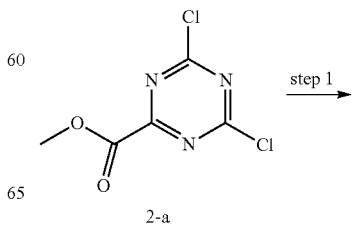

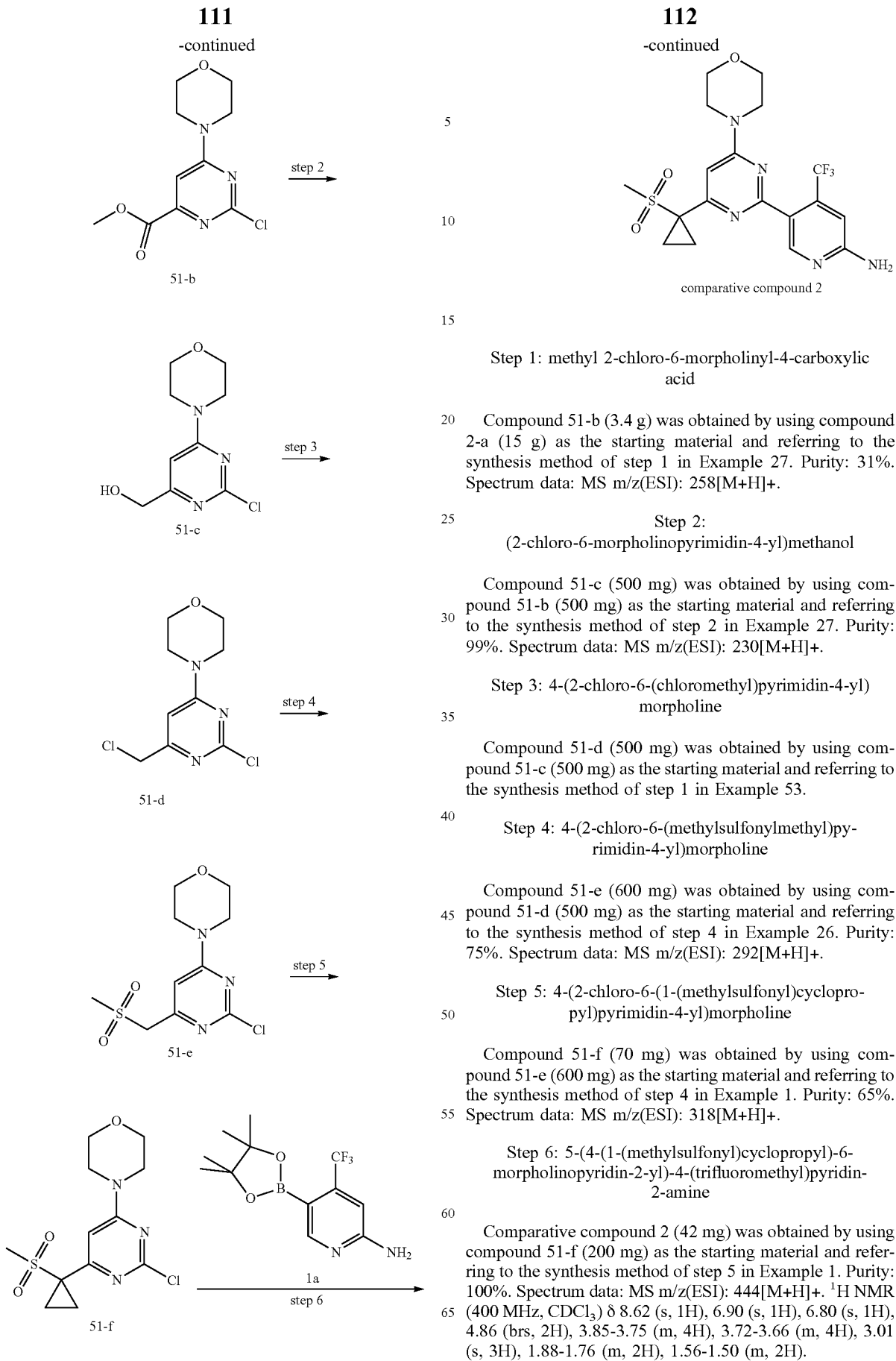

Step 1: methyl 2-chloro-6-morpholinyl-4-carboxylic acid

Compound 51-b (3.4 g) was obtained by using compound 2-a (15 g) as the starting material and referring to the synthesis method of step 1 in Example 27. Purity: 31%. Spectrum data: MS m/z(ESI): 258[M+H]+.

Step 2: (2-chloro-6-morpholinopyrimidin-4-yl)methanol

Compound 51-c (500 mg) was obtained by using compound 51-b (500 mg) as the starting material and referring to the synthesis method of step 2 in Example 27. Purity: 99%. Spectrum data: MS m/z(ESI): 230[M+H]+.

Step 3: 4-(2-chloro-6-(chloromethyl)pyrimidin-4-yl)morpholine

Compound 51-d (500 mg) was obtained by using compound 51-c (500 mg) as the starting material and referring to the synthesis method of step 1 in Example 53.

Step 4: 4-(2-chloro-6-(methylsulfonylmethyl)pyrimidin-4-yl)morpholine

Compound 51-e (600 mg) was obtained by using compound 51-d (500 mg) as the starting material and referring to the synthesis method of step 4 in Example 26. Purity: 75%. Spectrum data: MS m/z(ESI): 292[M+H]+.

Step 5: 4-(2-chloro-6-(1-(methylsulfonyl)cyclopropyl)pyrimidin-4-yl)morpholine

Compound 51-f (70 mg) was obtained by using compound 51-e (600 mg) as the starting material and referring to the synthesis method of step 4 in Example 1. Purity: 65%. Spectrum data: MS m/z(ESI): 318[M+H]+.

Step 6: 5-(4-(1-(methylsulfonyl)cyclopropyl)-6-morpholinopyridin-2-yl)-4-(trifluoromethyl)pyridin-2-amine Comparative compound 2 (42 mg) was obtained by using compound 51-f (200 mg) as the starting material and referring to the synthesis method of step 5 in Example 1. Purity: 100%. Spectrum data: MS m/z(ESI): 444[M+H]+. $^1$H NMR (400 MHz, CDCl$_3$) δ 8.62 (s, 1H), 6.90 (s, 1H), 6.80 (s, 1H), 4.86 (brs, 2H), 3.85-3.75 (m, 4H), 3.72-3.66 (m, 4H), 3.01 (s, 3H), 1.88-1.76 (m, 2H), 1.56-1.50 (m, 2H).

Comparative Example 3 The preparation of 4-(6-(1-(methylsulfonyl)cyclopropyl)-2-morpholinopyrimidin-4-yl)-3-(trifluoromethyl)aniline (Comparative compound 3)

comparative compound 3

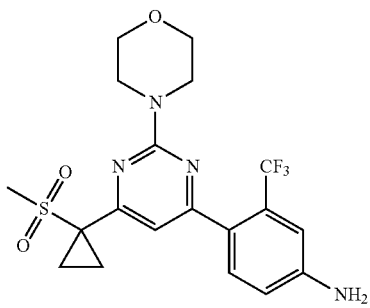

The title compound was prepared by referring to Example 1 except that 1a in step 5 was replaced by 11a. MS m/z(ESI): 443[M+H]+. $^1$H NMR (500 MHz, CDCl$_3$) δ 7.34 (d, J=8.3 Hz, 1H), 7.06 (s, 1H), 7.02 (d, J=2.2 Hz, 1H), 6.84 (dd, J=8.2, 2.3 Hz, 1H), 4.02 (brs, 2H), 3.86-3.80 (m, 4H), 3.80-3.73 (m, 4H), 3.08 (s, 3H), 1.85 (q, J=4.5 Hz, 2H) 1.60-1.57 (m, 2H).

Test Example 1: Determination of PI3K Kinase Activity

Test Reagents and Test Methods.

The PI3K kinase used in the experiment: p110α/p85α (Invitrogen PV4788), p110β/p85α (Millipore 14-603), p110δ/p85α (Millipore 14-604M), and p110γ (Invitrogen PV4786). ADP transcreener kinase (3010-10k) kit was purchased from Bellbrook labs.

The inhibition of PI3K kinase activity by the compound to be tested was determined by the following method. The working concentration of each component in the 25 μL enzyme reaction system was: p110α/p85α 3 ng (or p110β/p85α 60 ng, or p110δ/p85α 90 ng, or p110γ 100 ng), ATP 10 μM, PIP2: PS (Invitrogen PV5100) 30 μM and the DMSO concentration was 2% after addition of the compound to be tested.

At the time of the test, the compound to be tested was dissolved in dimethylsulfoxide (DMSO) according to the desired concentration of the experiment. The compound to be tested was gradiently diluted 3 times (0.00046-1 μM, 8 concentration points) with 10% DMSO. 5 μL of the compound to be tested was added to each well of a 96-well plate (Greiner 675076) in duplicate. 2.5× buffer was prepared and 1 μL of DTT (Millipore 20-265) was added to each 800 μL of 2.5× buffer. ATP/PIP2: PS enzyme/substrate working solution and the PI3K enzyme working solution in proper concentration were prepared with 2.5× buffer. 10 μL of ATP/PIP2: PS and 10 μL of the PI3K enzyme working solution were added to each well in a 96-well plate. The plate was shaken and mixed uniformly, and then incubated at 25° C. for 1 hour. At the same time, ADP and ATP (0.01 μM, 0.02 μM, 0.04 μM, 0.06 μM, 0.08 μM, 0.08 μM, 0.1 μM, 0.25 μM, 0.5 μM, 1 μM, 2 μM, 5 μM, 10 μM, 12 concentration points) were diluted with buffer to set the standard curve. After completion of the enzyme reaction, 25 μL of ADP assay solution (1% 100×ADP tracer, 0.79% ADP antibody and 10% 10× reaction stop solution) was added and incubated at 25° C. for 1 hour. Fluorescence polarization value [mP] of each well was measured with a Perkin Elmer Victor X5 Fluorescent Microplate. The ADP concentration [ADP] was calculated from the ADP/ATP standard curve and the IC$_{50}$ values were calculated using the XLFit software. The measured IC$_{50}$ values of inhibitory activities of the compounds tested against PI3K kinase are shown in Table 1.

TABLE 1

IC$_{50}$ values of inhibitory activities of the compounds of the present invention against PI3K kinase

| Compound No. | PI3K-α/nM | PI3K-β/nM | PI3K-γ/nM | PI3K-δ/nM |
|---|---|---|---|---|
| S-1 | 16 | 314 | 288 | 240 |
| S-4 | 12 | 527 | 354 | 184 |
| S-6 | 16 | 264 | 164 | 197 |
| S-9 | 5 | 105 | 155 | 63 |
| S-10 | 42 | 1140 | 592 | 367 |
| S-13 | 67 | 1666 | >3000 | 226 |
| S-14 | 13 | 1124 | | |
| S-16 | 13 | 196 | 138 | 244 |
| S-18 | 58 | 548 | 957 | 246 |
| S-19 | 80 | 512 | >3000 | 493 |
| S-20 | 24 | 676 | 1163 | 42 |
| S-21 | 9 | 832 | 843 | 214 |
| S-22 | 55 | 1544 | 2122 | 491 |
| S-23 | 16 | 620 | 525 | 62 |
| S-24 | 10 | 376 | 291 | 85 |
| S-25 | 26 | 217 | 1932 | 67 |
| S-28 | 13 | 121 | 765 | 78 |
| S-29 | 40 | 1738 | 256 | 612 |
| S-30 | 12 | 18 | 141 | 12 |
| S-31 | 12 | 171 | 148 | 103 |
| S-32 | 76 | 977 | 923 | 161 |
| S-33 | 12 | 115 | 112 | 58 |
| S-37 | 4 | 28 | 114 | 84 |
| S-38 | 17 | 113 | 369 | 212 |
| S-41 | 6 | 82 | 331 | 79 |
| S-42 | 22 | 1211 | 718 | 324 |
| S-45 | 35 | 28 | 78 | 17 |
| S-46 | 6 | 8 | 96 | 13 |
| S-49 | 17 | 327 | 2018 | 85 |
| S-52 | 18 | 2784 | 914 | 336 |
| S-53 | 33 | 1552 | 287 | 516 |
| S-54 | 12 | 92 | 199 | 145 |
| S-57 | 18 | 284 | 236 | 62 |
| S-58 | 4 | 72 | 121 | 33 |
| S-59 | 37 | 721 | 813 | 235 |
| S-63 | 21 | 228 | 428 | 158 |
| S-64 | 13 | 27 | 431 | 19 |
| S-65 | 22 | 1223 | | |
| S-66 | 9 | 73 | 160 | 46 |
| S-67 | 6 | 208 | 113 | 59 |
| S-68 | 8 | 92 | 184 | 143 |
| S-70 | 22 | 525 | | |
| S-71 | 9 | 177 | 1026 | |
| S-72 | 18 | 797 | 1153 | 370 |
| S-73 | 14 | 396 | 623 | 514 |
| S-74 | 28 | 2088 | 2495 | 1011 |
| S-75 | 23 | 943 | 654 | 810 |
| S-76 | 53 | 316 | 228 | 207 |
| S-78 | 7 | 419 | 925 | 85 |
| S-81 | 43 | 812 | 181 | 178 |
| S-82 | 39 | 86 | 116 | 132 |
| S-83 | 20 | 376 | 204 | 46 |
| S-84 | 21 | 812 | 219 | 18 |
| S-85 | 29 | 484 | 244 | 228 |
| S-86 | 26 | 763 | 192 | 397 |
| S-87 | 14 | 386 | 134 | 117 |
| S-88 | 48 | 521 | 98 | 209 |
| S-91 | 40 | 646 | | |
| Comparative compound 2 | 90 | 2161 | >3000 | 2578 |

TABLE 2

IC$_{50}$ values of inhibitory activities of the compounds of the present invention against PI3K-α kinase

| Compound No. | PI3K-α/nM |
|---|---|
| S-1 | 16 |
| S-2 | 550 |
| S-3 | 280 |
| S-4 | 12 |
| S-6 | 16 |
| S-9 | 5 |
| S-10 | 42 |
| S-14 | 13 |
| S-16 | 13 |
| S-18 | 58 |
| S-19 | 80 |
| S-20 | 24 |
| S-21 | 9 |
| S-22 | 65 |
| S-23 | 16 |
| S-24 | 10 |
| S-25 | 26 |
| S-26 | 390 |
| S-27 | 285 |
| S-28 | 13 |
| S-29 | 40 |
| S-30 | 12 |
| S-31 | 12 |
| S-33 | 12 |
| S-37 | 4 |
| S-38 | 17 |
| S-40 | 92 |
| S-41 | 6 |
| S-42 | 22 |
| S-44 | 858 |
| S-45 | 35 |
| S-46 | 6 |
| S-49 | 17 |
| S-50 | 39 |
| S-52 | 18 |
| S-53 | 33 |
| S-54 | 12 |
| S-55 | 40 |
| S-57 | 18 |
| S-58 | 4 |
| S-59 | 37 |
| S-60 | 35 |
| S-61 | 195 |
| S-62 | 189 |
| S-65 | 22 |
| S-66 | 9 |
| S-67 | 6 |
| S-68 | 8 |
| S-69 | 59 |
| S-70 | 22 |
| S-71 | 9 |
| S-72 | 18 |
| S-73 | 14 |
| S-74 | 28 |
| S-75 | 23 |
| S-76 | 53 |
| S-77 | 62 |
| S-78 | 7 |
| S-79 | 55 |
| S-80 | 31 |
| S-85 | 29 |
| S-86 | 26 |
| S-87 | 14 |
| S-88 | 48 |
| S-90 | 75 |
| S-91 | 40 |
| Comparative compound 3 | >1000 |

As can be seen from Table 1, the compounds of the present invention have a significant inhibitory effect on all the PI3K kinases (PI3K-α, PI3K-β, PI3K-γ, and PI3K-δ). The inhibitory activities on PI3K-β, PI3K-γ, and PI3K-δ are weaker compared with the PI3K-α inhibitory activity, which means that the compounds of the present invention have some selective inhibitory effect on PI3K-α. Namely, the selectivity of the compounds of the present invention to PI3K kinase is α>δ>β or γ.

As can be seen from Table 2, the example compounds of the present invention have a strong inhibitory effect on the PI3K-α kinase, and the study has shown that when the substituent at position 4 of the pyrimidine ring is replaced by phenyl, the inhibitory effect on PI3K-α kinase is significantly reduced.

In addition, most of the compounds of the present invention have an inhibitory activity against PI3K-α kinase higher than that of the positive compound BKM-120 (IC$_{50}$=57), wherein the inhibitory activities of some of the preferred compounds (e.g., S-9, S-37 and S-46) are increased by about 10 times.

When Z is not N or CH; or X is a bond, and Y is a heterocycle, an ester group, an amide group or an amine group; or the methylene attached to X is not substituted in the compound, the inhibition effect is significantly reduced.

Test Example 2: Inhibition of P-AKt Phosphorylation Level in PC-3 Cells

This experiment was performed by cell level fluorescence image processing method.

I. Reagents and Solutions

Triton X-100: 10% aqueous Triton X-100 solution (Sigma T8787-100 mL) was prepared, stored at 4° C. and diluted by 1:100 to give 0.1% Triton X-100 aqueous solution for use in the experiment.

Prodium Iodide (PI): 1 mg/mL (1.5 mM) PI (Sigma P4170) storage solution was prepared with PBS and stored at −25° C. in the dark. For use, the PI storage solution was diluted with PBS by 1:1000 to give a 1.5 μM solution and used in dark.

II. PC-3 Cells 2.1 PC-3 Cell Treatment

PC-3 cells in logarithmic growth phase were digested with 0.25% EDTA trypsin. 3000 cells/90 μL were seeded in a 96-well plate (BD 356692) and cultured at 37° C. and 5% CO$_2$. After the cells adhered, 10 μL of the compound to be tested which was gradiently diluted 3 times (0.0046 to 10 μM, 8 concentration points, in duplicate) was added and incubated for 2 hours, followed by addition of 100 μL of 4% paraformaldehyde (DINGGUO AR-0211) and incubated at room temperature for 45 minutes. Then 100 μL of 0.1% Triton X-100 solution was added and incubated for another 30 minutes.

2.2 Detection Step

Triton X-100 solution was removed and the cells were rinsed with 200 μl of PBS twice (300 rpm vibration for 1 minute). The blocking solution (1% BSA solution in PBS) (Genview FA016-100G) was added and incubated at room temperature for 2 hours. The plate was rinsed with PBS once (300 rpm, 1 min) and 30 μL of Ser473-p-Akt antibody (cell signaling 4060L) diluted with 0.1% BSA was added and incubated overnight at 4° C. Ser473-p-Akt antibody was removed and the plate was rinsed with PBS twice (300 rpm, 1 minute). 35 μL of Alexa Flour 488 donkey anti-rabbit IgG (Invitrogen A21206) was added and incubated at room temperature for 1.5 hours. The plate was rinsed with PBS twice (300 rpm, 1 minute) and 35 μL of 1.5 μM PI was added and incubated at room temperature for 0.5 h. The fluorescence intensity was measured with Acumen eX3 (TTP LabTech).

2.3 Data Analysis

10 μM BEZ235 (Selleck S1009) treatment group was negative control and DMSO treatment group was positive control.

Inhibition ratio %=[1−(the mean value of the fluorescence intensity of the compound to be tested−the mean value of the fluorescence intensity of the negative control group)/(the mean value of the fluorescence intensity of the positive control group−the mean value of the fluorescence intensity of the negative control group)]×100%

2.4 $IC_{50}$ values were calculated based on the calculated inhibition ratios by using XLFIT 5.0 software and shown in Table 3.

TABLE 3

The measured $IC_{50}$ values of the compounds of the present invention for PC-3 cell activity

| Compound No. | PC-3 cell ($IC_{50}$/nM) |
|---|---|
| S-1 | 319 |
| S-4 | 248 |
| S-9 | 184 |
| S-10 | 384 |
| S-13 | 463 |
| S-16 | 312 |
| S-18 | 430 |
| S-19 | 575 |
| S-23 | 366 |
| S-28 | 301 |
| S-30 | 101 |
| S-31 | 126 |
| S-32 | 74 |
| S-33 | 109 |
| S-37 | 198 |
| S-38 | 332 |
| S-39 | 513 |
| S-40 | 465 |
| S-41 | 414 |
| S-45 | 156 |
| S-46 | 131 |
| S-49 | 382 |
| S-50 | 39 |
| S-54 | 488 |
| S-58 | 367 |
| S-63 | 577 |
| S-64 | 330 |
| S-66 | 253 |
| S-67 | 187 |
| S-68 | 183 |
| S-71 | 555 |
| S-75 | 385 |
| S-76 | 531 |
| S-81 | 215 |
| S-82 | 369 |
| S-83 | 196 |
| S-84 | 121 |
| S-85 | 161 |
| S-86 | 240 |
| S-88 | 349 |
| S-89 | 351 |
| Comparative compound 1 | 2257 |
| Comparative compound 2 | 1025 |
| BKM-120 (positive control) | 596 |

As can be seen from Table 3, the compounds of the examples of the present invention all have a remarkable inhibitory activity against Akt phosphorylation in PC-3 cells. The compounds of the examples of the present invention apparently have a stronger inhibitory activity against Akt phosphorylation in PC-3 cells compared with the positive compound BKM-120 and comparative compounds 1 and 2.

Test Example 4: Cell Inhibitory Activity Detected by MTT Assay

The MTT assay procedure and steps were carried out as well known to those skilled in the art, and all the reagents used in the methods were commercially available.

The cells in logarithmic growth phase were digested with 0.25% EDTA trypsin (Gibco, 25200-056) and resuspended in fresh medium. 90 μL of the cell suspension was inoculated into a 96-well cell culture plate (BD Faclon 353072) with a suitable cell density and cultured at 37° C. under 5% $CO_2$. After the cells adhered, 10 μL of the test compound at different concentrations (0.0046-10 μM, 8 concentration points) was added and incubated for another 72 h. 10 μL of MTT (5 mg/mL PBS solution) (Sigma, M5655) was added to react for 4 h. The absorbance at 492 nm was measured by using Thermo Scientific Multiskan MK3 microplate reader and $IC_{50}$ was calculated using XLFIT 5.0 software (UK IDBS).

T47D cell culture medium: RPMI-1640 medium (Hyclone SH30809.01B)+10% FBS (Gibco 10099-141)

MCF-7 cell culture medium: DMEM medium (Hyclone SH30243.01B+10% FBS (Gibco 10099-141)

NIH3T3 cell culture medium: DMEM medium (Hyclone SH30243.01B+10% FBS (Gibco 10099-141)

TABLE 4

$IC_{50}$ values of the compounds of the present invention for T47D cell growth inhibition

| Compound No. | T47D cell ($IC_{50}$/nM) |
|---|---|
| S-1 | 167 |
| S-4 | 124 |
| S-6 | 129 |
| S-9 | 93 |
| S-10 | 218 |
| S-13 | 244 |
| S-14 | 278 |
| S-16 | 58 |
| S-18 | 160 |
| S-19 | 178 |
| S-20 | 332 |
| S-23 | 20 |
| S-24 | 305 |
| S-25 | 324 |
| S-28 | 225 |
| S-30 | 100 |
| S-31 | 73 |
| S-32 | 95 |
| S-33 | 120 |
| S-37 | 202 |
| S-38 | 244 |
| S-41 | 148 |
| S-42 | 139 |
| S-43 | 317 |
| S-45 | 163 |
| S-46 | 137 |
| S-49 | 208 |
| S-50 | 449 |
| S-54 | 255 |
| S-57 | 242 |
| S-58 | 129 |
| S-65 | 280 |
| S-66 | 147 |
| S-67 | 88 |
| S-68 | 73 |
| S-70 | 219 |
| S-71 | 165 |
| S-75 | 249 |

TABLE 4-continued

IC$_{50}$ values of the compounds of the present invention for T47D cell growth inhibition

| Compound No. | T47D cell (IC$_{50}$/nM) |
|---|---|
| S-76 | 289 |
| S-78 | 206 |
| S-81 | 123 |
| S-82 | 62 |
| S-83 | 30 |
| S-84 | 33 |
| S-85 | 63 |
| S-86 | 69 |
| S-87 | 101 |
| S-88 | 81 |
| S-89 | 118 |
| Comparative compound 1 | 1220 |
| Comparative compound 2 | 854 |

TABLE 5

IC$_{50}$ values of the compounds of the present invention for MCF-7 cell growth inhibition

| Compound No. | MCF-7 cell (IC$_{50}$/nM) |
|---|---|
| S-1 | 283 |
| S-6 | 112 |
| S-9 | 78 |
| S-10 | 340 |
| S-13 | 153 |
| S-14 | 267 |
| S-16 | 224 |
| S-18 | 437 |
| S-23 | 246 |
| S-28 | 295 |
| S-30 | 101 |
| S-31 | 45 |
| S-32 | 73 |
| S-33 | 79 |
| S-37 | 258 |
| S-38 | 180 |
| S-39 | 441 |
| S-40 | 355 |
| S-41 | 170 |
| S-42 | 159 |
| S-45 | 329 |
| S-46 | 301 |
| S-49 | 187 |
| S-53 | 408 |
| S-54 | 159 |
| S-57 | 286 |
| S-58 | 184 |
| S-63 | 240 |
| S-65 | 469 |
| S-66 | 212 |
| S-67 | 105 |
| S-68 | 94 |
| S-71 | 436 |
| S-73 | 176 |
| S-75 | 131 |
| S-76 | 66 |
| S-78 | 318 |
| S-80 | 474 |
| S-81 | 104 |
| S-82 | 27 |
| S-83 | 11 |
| S-84 | 15 |
| S-85 | 25 |
| S-86 | 29 |
| S-87 | 170 |
| S-88 | 102 |
| S-89 | 30 |
| Comparative compound 1 | 996 |
| Comparative compound 2 | 639 |

As shown in Table 4 and Table 5, the compounds in the examples of the present invention exhibit significant proliferation inhibitory activity against the breast cancer cell lines T47D and MCF-7. Compared with the comparative compounds 1 and 2, the compounds in the examples of the present invention have significantly stronger inhibitory activity against the proliferation of the above two cell lines.

The results show that the substitution position of the morpholine ring on the pyrimidine ring has a great effect on the inhibitory activity on the cell lines. When the substituent morpholine ring is at position 4 or 6, the inhibitory activity of the compound on the cell lines is significantly reduced in comparison with the position 2 substitution.

All the compounds in the examples of the present invention showed low cytotoxicity and some of the test results are shown in Table 6, wherein, the symbols in the table are defined as follows:

A: NIH3T3 cells (IC$_{50}$/nM) value is >10000, indicating extremely low cytotoxicity:

B: NIH3T3 cells (IC$_{50}$/nM) value is in the range of 5000-10,000, indicating very low cytotoxicity;

C: NIH3T3 cells (IC$_{50}$/nM) value is in the range of 3000-5000, indicating low cytotoxicity;

D: NIH3T3 cells (IC$_{50}$/nM) value is in the range of 1000-3000, indicating slightly high cytotoxicity;

E: NIH3T3 cells (IC$_{50}$/nM) value is in the range of 500-1000, indicating high cytotoxicity;

F: NIH3T3 cells (IC$_{50}$/nM) value is <500, indicating extremely high cytotoxicity.

TABLE 6

The test results of the compounds of the present invention for NIH3T3 cells

| Compound No. | NIH3T3 cell (IC$_{50}$/nM) |
|---|---|
| S-2 | B |
| S-3 | A |
| S-5 | D |
| S-6 | D |
| S-7 | A |
| S-8 | A |
| S-10 | D |
| S-14 | D |
| S-15 | B |
| S-19 | D |
| S-20 | D |
| S-21 | D |
| S-22 | D |
| S-24 | B |
| S-25 | D |
| S-26 | A |
| S-29 | D |
| S-36 | C |
| S-44 | D |
| S-48 | D |
| S-50 | D |
| S-52 | C |

TABLE 6-continued

The test results of the compounds of the present invention for NIH3T3 cells

| Compound No. | NIH3T3 cell (IC$_{50}$/nM) |
|---|---|
| S-53 | D |
| S-56 | A |
| S-57 | D |
| S-59 | D |

As can be seen from Table 6, the compounds in the examples of the present invention all have low toxicity to NIH3T3 cells.

Test Example 5: Metabolism Stability Assay

1. Preparation of Buffer

Buffer A: 1 L solution of 100 mM potassium dihydrogen phosphate containing 1 mM EDTA (Sigma, V900157-100G) was prepared. Buffer B: 1 L solution of 100 mM dipotassium hydrogen phosphate containing 1 mM EDTA was prepared. Buffer C: 700 mL of buffer B was taken out and titrated with buffer A to pH 7.4.

2. Preparation of the compound to be tested and the positive control drug (ketanserin (Sigma S006-10MG))

2.1 10 μl of 10 mM compound to be tested and 10 μl of 10 mM ketanserin were taken out and 190 μl of pure acetonitrile was added to each of them to prepare 500 μM compound to be tested and ketanserin, respectively.

2.2 20 μl (20 mg/mL) of liver microsomes (XENOTECH, H0610) stock solution was added to 513.4 μl of buffer C on wet ice. 0.75 mg/mL liver microsomal solution was obtained.

2.3 1.5 μl of each of the above-mentioned compound to be tested and ketanserin solution was added to 498.5 μl of liver microsomal solution (0.7 5 mg/mL) respectively on wet ice. 1.5 μM mixed solution of compound to be tested and 1.5 μM mixed solution of ketanserin were obtained.

2.4 At the time points 0, 5, 15, 30, 45, and 60 min, 30 μl of the mixed solution of compound to be tested and 30 μl of the mixed solution of ketanserin were dispensed into the reaction plate on wet ice, respectively.

2.5 5 mg reduced coenzyme II (Roche, 10621706001) was weighed and dissolved in 1 mL of buffer C. 6 mM reduced coenzyme II solution was obtained. The reduced coenzyme II solution was dispensed into the reaction plate.

2.6 Imipramine was dissolved to give a 10 mM solution. 10 μl imipramine solution was added to 100 mL of blank acetonitrile to generate the internal reference.

2.7 At 0 min, 135 μL of iced acetonitrile (Merck, UN 1648) containing the internal reference was added to each well and then 15 μL of buffer C was added.

2.8 The reaction plate was placed into a 37° C. water bath incubator for 5 min. In the reaction plate, 15 μL of reduced coenzyme II solution was added to each well to initiate the reaction, and the time keeping was started. At the time points of 5, 15, 30, 45, and 60 min, 135 μL of iced acetonitrile containing the internal reference was added to each well to terminate the reaction.

2.9 The reaction plate was sealed with an aluminum film, placed on a vibration mixer and shaken at 500 rpm for 5 min. The plate was then centrifuged in a centrifuge at 3750 rp for 15 min.

2.10 The sample was diluted with pure water in accordance with the ratio of 1:1 and detected by LC/MS. The clearance ratio was calculated according to the following formula based on the obtained values, and shown in Table 7.

Half-life: 0.693/K (the slope by plotting based on the incubation time and logarithm of the concentration value)

Clearance ratio: (0.693/half-life)*(1/protein concentration (0.5 mg/mL))*(proportional factor)

Wherein, the K value and the proportional factor were calculated by those skilled in the art according to the methods described in the prior art and contained in the instructions of the liver microsome product.

TABLE 7

Clearance ratio of liver microsomal metabolism in mice

| Compound No. | Clearance ratio (mL/min/kg) mouse | Compound No. | Clearance ratio (mL/min/kg) mouse |
|---|---|---|---|
| S-4 | 442.63 | S-20 | 5641.44 |
| S-21 | 6337.31 | S-38 | 103.77 |
| S-45 | 89.54 | S-46 | 100.1 |
| S-59 | 7163.43 | S-82 | 39.75 |

As can be seen from Table 7, different sulfonyl groups have significant impact on the metabolism stability. When the arylsulfonyl is replaced by alkylsulfonyl, the metabolism stability is greatly improved.

The compounds of the present invention, or the pharmaceutically acceptable salt, solvate, stereoisomer or prodrug thereof, or the pharmaceutical composition and use thereof, have a significant PI3K kinase inhibitory activity. They not only exhibit high inhibitory activity on PI3K-α kinase at enzyme level, but also exhibit high inhibitory effect on PIK3CA mutant breast cancer cell lines T47D and MCF-7, and at the same time they also have low cytotoxicity.

Moreover, these compounds have low cytotoxicity in normal cell lines (such as NIH-3T3 cells), thereby significantly reducing nonspecific side effects. They may be formulated with one or more pharmaceutically acceptable carriers in a suitable dosage form for administration. These dosage forms are suitable for oral administration, rectal administration, topical administration, intraoral administration, and other parenteral administration (e.g., subcutaneous, intramuscular, intravenous, etc.). For example, the dosage forms suitable for oral administration include capsules, tablets, granules, syrups and the like. The compounds of the present invention contained in these formulations may be solid powders or granules; solutions or suspensions in aqueous or non-aqueous liquids; water-in-oil or oil-in-water emulsions and the like. They are greatly valuable for practical use.

The invention claimed is:

1. A compound of formula (I), or a pharmaceutically acceptable salt, solvate, stereoisomer or prodrug thereof,

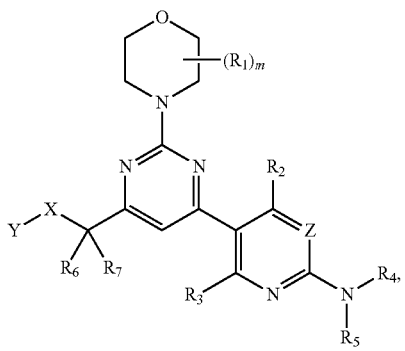

(I)

wherein, Z is N or CR$_0$;

(R$_1$)$_m$ means that the hydrogen atom(s) on the morpholine ring is substituted by R$_1$ and the number of R$_1$ is m, wherein m is 0, 1, 2, 3, 4, 5 or 6, each R$_1$ is the same or different and is independently selected from the group consisting of hydrogen, deuterium, C$_{1-10}$ alkyl, deuterated C$_{1-10}$ alkyl and C$_{1-10}$ haloalkyl; or any two R$_1$ are linked by a single bond or —(CH$_2$)$_p$—, p is 1, 2, 3, 4, 5 or 6;

R$_2$ and R$_3$ are each independently selected from the group consisting of hydrogen, halogen, C$_{1-10}$ alkyl, C$_{1-10}$ haloalkyl, C$_{1-10}$ alkoxy, C$_{3-8}$ cycloalkoxy, —COC$_{1-10}$ alkyl, —CON(C$_{1-10}$ alkyl)$_2$, —C(O)OC$_{1-10}$ alkyl and —OC(O)C$_{1-10}$ alkyl;

R$_4$ and R$_5$ are each independently selected from the group consisting of hydrogen, C$_{1-10}$ alkyl, C$_{1-10}$ haloalkyl and C$_{3-10}$ cycloalkyl;

R$_6$ and R$_7$, together with the carbon atom to which they are attached, form a 3- to 6-membered saturated monocyclic ring;

X is a bond, —(CR$_a$R$_b$)$_r$—, —N(R$_c$)— or —C(O)—; Y is selected from the group consisting of —SO$_2$R$_8$, —OR$_9$, —N(R$_{81}$R$_{82}$)$_2$, —C(O)C$_{1-10}$ alkyl, and 3- to 10-membered saturated mono-heterocyclic ring;

R$_0$ is hydrogen, halogen, C$_{1-10}$ alkyl or C$_{1-10}$ haloalkyl;

R$_a$, R$_b$, and R$_c$ are each independently hydrogen or C$_{1-10}$ alkyl;

r is 1, 2 or 3;

R$_8$ is selected from the group consisting of C$_{1-10}$ alkyl, C$_{6-10}$ aryl, and C$_{3-10}$ cycloalkyl, wherein the aryl is unsubstituted or substituted with 1 to 5 substituents selected from the group consisting of halogen and C$_{1-10}$ alkyl;

R$_9$ is selected from the group consisting of hydrogen, C$_{1-10}$ alkyl, C$_{1-10}$ haloalkyl, C$_{6-10}$ aryl, C$_{3-10}$ cycloalkyl, —(CR$_a$R$_b$)$_r$—C$_{6-10}$ aryl and —C(O)C$_{1-10}$ alkyl; and R$_{81}$ and R$_{82}$ are each independently hydrogen or C$_{1-10}$ alkyl.

2. The compound or the pharmaceutically acceptable salt, solvate, stereoisomer or prodrug thereof according to claim 1, wherein when m is 0 or 1, R$_1$ is methyl or CD$_3$; and when m is 2, R$_1$ is methyl or CD$_3$, and p is 1 or 2.

3. The compound or the pharmaceutically acceptable salt, solvate, stereoisomer or prodrug thereof according to claim 1, wherein R$_2$ and R$_3$ are each independently selected from the group consisting of hydrogen, halogen, C$_{1-6}$ alkyl, C$_{1-6}$ haloalkyl, C$_{1-6}$ alkoxy, C$_{3-6}$ cycloalkoxy, —COC$_{1-3}$ alkyl, —C(O)OC$_{1-3}$ alkyl, —OC(O)C$_{1-3}$ alkyl and —CON(C$_{1-3}$ alkyl)$_2$.

4. The compound or the pharmaceutically acceptable salt, solvate, stereoisomer or prodrug thereof according to claim 1, wherein R$_4$ and R$_5$ are each independently selected from the group consisting of hydrogen, methyl, ethyl, propyl, isopropyl, monofluoroethyl, difluoromethyl, trifluoromethyl, cyclopropyl, cyclobutyl, cyclopentyl and cyclohexyl.

5. The compound or the pharmaceutically acceptable salt, solvate, stereoisomer or prodrug thereof according to claim 1, wherein R$_8$ is selected from the group consisting of C$_{1-6}$ alkyl, C$_{3-8}$ cycloalkyl, and substituted or unsubstituted phenyl, wherein said "substituted" means that 1-5 hydrogen atoms on the benzene ring are substituted with the substituents selected from the group consisting of halogen and C$_{1-3}$ alkyl.

6. The compound or the pharmaceutically acceptable salt, solvate, stereoisomer or prodrug thereof according to claim 1, wherein R$_9$ is hydrogen or C$_{1-6}$ alkyl.

7. The compound or the pharmaceutically acceptable salt, solvate, stereoisomer or prodrug thereof according to claim 1, wherein X is a bond, —CH$_2$—, —NH— or —N(CH$_3$)—.

8. The compound or the pharmaceutically acceptable salt, solvate, stereoisomer or prodrug thereof according to claim 1, wherein when X is a bond, Y is —SO$_2$R$_8$;

when X is —CH$_2$—; Y is selected from the group consisting of 3- to 10-membered saturated mono-heterocyclic ring, and —SO$_2$R$_8$;

when X is —C(O)—; Y is selected from the group consisting of —OR$_9$ and 3- to 10-membered saturated mono-heterocyclic ring; or when X is —NH— or —N(CH$_3$)—, Y is —C(O)C$_{1-10}$ alkyl or —SO$_2$R$_8$.

9. A compound of formula (I-a), or a pharmaceutically acceptable salt, solvate, stereoisomer or prodrug thereof:

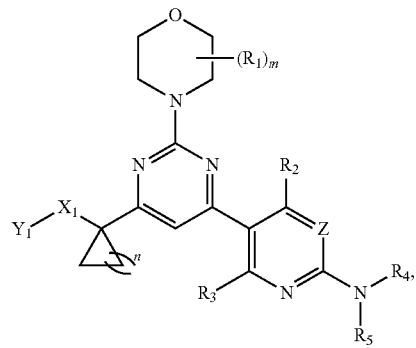

(I-a)

wherein, n is 1, 2, 3 or 4;

Z is N or CR$_0$ wherein R$_0$ is hydrogen, halogen, C$_{1-10}$ alkyl or C$_{1-10}$ haloalkyl;

(R$_1$)$_m$ means that the hydrogen atom(s) on the morpholine ring is substituted by R$_1$ and the number of R$_1$ is m, wherein m is 0, 1, 2, 3, 4, 5 or 6, each R$_1$ is the same or different and is independently selected from the group consisting of hydrogen, deuterium, C$_{1-10}$ alkyl, deuterated C$_{1-10}$ alkyl and C$_{1-10}$ haloalkyl; or any two R$_1$ are linked by a single bond or —(CH$_2$)$_p$—, p is 1, 2, 3, 4, 5 or 6;

R$_2$ and R$_3$ are each independently selected from the group consisting of hydrogen, halogen, C$_{1-10}$ alkyl, C$_{1-10}$ haloalkyl, C$_{1-10}$ alkoxy, C$_{3-8}$ cycloalkoxy, —COC$_{1-10}$ alkyl, —CON(C$_{1-10}$ alkyl)$_2$, —C(O)OC$_{1-10}$ alkyl and —OC(O)C$_{1-10}$ alkyl;

R₄ and R₅ are each independently selected from the group consisting of hydrogen, C₁₋₁₀ alkyl, C₁₋₁₀ haloalkyl and C₃₋₁₀ cycloalkyl;

X₁ is a bond or is —CH₂—, —NH— or —N(CH₃)—; and

Y₁ is selected from the group consisting of —SO₂R₈, —OR₉, halogen, C₁₋₁₀ haloalkyl, 5- to 6-membered monocyclic heteroaryl ring, 8- to 10-membered bicyclic heteroaryl ring, 3- to 10-membered saturated or partially unsaturated monocyclic ring and 3- to 10-membered saturated mono-heterocyclic ring, wherein R₈ is selected from the group consisting of hydroxy, halogen, —N(R₈₁R₈₂)₂, —OC₁₋₁₀ alkyl, C₁₋₁₀ alkyl, C₁₋₁₀ haloalkyl, C₆₋₁₀ aryl, and C₃₋₁₀ cycloalkyl, —(CR$_a$R$_b$)$_r$—C₆₋₁₀ aryl, and 5- to 6-membered monocyclic heteroaryl ring, wherein the aryl is unsubstituted or substituted with 1 to 5 substituents selected from the group consisting of halogen and C₁₋₁₀ alkyl;

R₉ is selected from the group consisting of hydrogen, C₁₋₁₀ alkyl, C₁₋₁₀ haloalkyl, C₆₋₁₀ aryl, C₃₋₁₀ cycloalkyl, —(CR$_a$R$_b$)$_r$—C₆₋₁₀ aryl and —C(O)C₁₋₁₀ alkyl;

R₈₁ and R₈₂ are each independently hydrogen or C₁₋₁₀ alkyl; and

R$_a$ and R$_b$ are each independently hydrogen or C₁₋₁₀ alkyl, and r is 1, 2 or 3.

10. The compound or the pharmaceutically acceptable salt, solvate, stereoisomer or prodrug thereof according to claim 9, wherein when X₁ is a bond, Y₁ is selected from the group consisting of 5- to 6-membered monocyclic heteroaryl ring, 8- to 10-membered bicyclic heteroaryl ring, —SO₂R₈, —OR₉, halogen and C₁₋₁₀ haloalkyl;

when X₁ is —CH₂—, Y₁ is selected from the group consisting of 3- to 10-membered saturated mono-heterocyclic ring and —SO₂R₈; or when X₁ is —NH— or —N(CH₃)—, Y₁ is —SO₂R₈.

11. A compound of formula (II), or a pharmaceutically acceptable salt, solvate, stereoisomer or prodrug thereof:

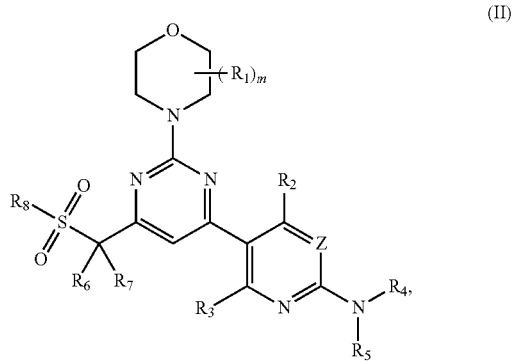

(II)

wherein,

Z is N or CR₀, wherein R₀ is hydrogen, halogen, C₁₋₁₀ alkyl or C₁₋₁₀ haloalkyl;

(R₁)$_m$ means that the hydrogen atom(s) on the morpholine ring is substituted by R₁ and the number of R₁ is m, wherein m is 0, 1, 2, 3, 4, 5 or 6, each R₁ is the same or different and is independently selected from the group consisting of hydrogen, deuterium, C₁₋₁₀ alkyl, deuterated C₁₋₁₀ alkyl and C₁₋₁₀ haloalkyl; or any two R₁ are linked by a single bond or —(CH₂)$_p$—, p is 1, 2, 3, 4, 5 or 6;

R₂ and R₃ are each independently selected from the group consisting of hydrogen, halogen, C₁₋₁₀ alkyl, C₁₋₁₀ haloalkyl, C₁₋₁₀ alkoxy, C₃₋₈ cycloalkoxy, —COC₁₋₁₀ alkyl, —CON(C₁₋₁₀ alkyl)₂, —C(O)OC₁₋₁₀ alkyl and —OC(O)C₁₋₁₀ alkyl;

R₄ and R₅ are each independently selected from the group consisting of hydrogen, C₁₋₁₀ alkyl, C₁₋₁₀ haloalkyl and C₃₋₁₀ cycloalkyl;

R₆ and R₇ are each independently selected from the group consisting of hydrogen, halogen, C₁₋₁₀ alkyl and C₁₋₁₀ haloalkyl, or R₆ and R₇, together with the carbon atom to which they are attached, form a 3- to 10-membered saturated or 3- to 6-membered unsaturated monocyclic ring, and 3- to 10-membered saturated or partially unsaturated mono-heterocyclic ring containing 1-3 heteroatoms independently selected from the group consisting of nitrogen, oxygen and sulfur; and R₈ is selected from the group consisting of hydroxy, halogen, —N(R₈₁R₈₂)₂, —OC₁₋₁₀ alkyl, C₁₋₁₀ alkyl, C₁₋₁₀ haloalkyl, C₆₋₁₀ aryl, C₃₋₁₀ cycloalkyl, —(CR$_a$R$_b$)$_r$—C₆₋₁₀ aryl, and 5- to 6-membered monocyclic heteroaryl ring, wherein the aryl is unsubstituted or substituted with 1 to 5 substituents selected from the group consisting of halogen and C₁₋₁₀ alkyl; R₈₁ and R₈₂ are each independently hydrogen or C₁₋₁₀ alkyl; R$_a$ and R$_b$ are each independently hydrogen or C₁₋₁₀ alkyl, and r is 1, 2 or 3.

12. The compound or the pharmaceutically acceptable salt, solvate, stereoisomer or prodrug thereof according to claim 11, wherein:

(i) m is 0 or 1;

R₁ is hydrogen or methyl;

R₈ is selected from the group consisting of methyl, ethyl, propyl, isopropyl, monofluoroethyl, difluoromethyl, trifluoromethyl, cyclopropyl, cyclobutyl, cyclopentyl and cyclohexyl;

Z is CH, CCF₃ or N;

R₂ is hydrogen, methoxy, F, Cl or trifluoromethyl; R₃ is H; R₄ is hydrogen or methyl; R₅ is hydrogen or methyl; and R₆ and R₇ are each independently selected from the group consisting of hydrogen, F, Cl, methyl, ethyl, propyl, isopropyl, monofluoromethyl, monofluoroethyl, difluoromethyl, trifluoromethyl; or R₆ and R₇, together with carbon atom to which they are attached, form the following structure:

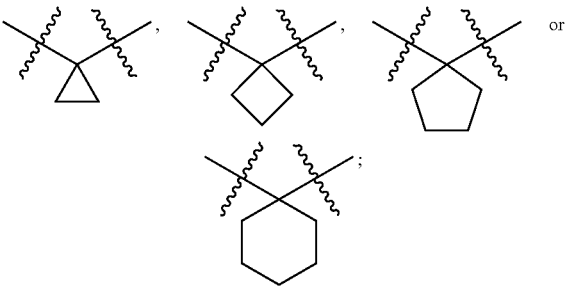

(ii) m is 0;

Z is CH;

R₂ is F, Cl or trifluoromethyl; R₃ is H; R₄ and R₅ are H;

R₈ is substituted or unsubstituted phenyl; wherein said "substituted" means that 1, 2 or 3 hydrogen atoms on the benzene ring are substituted with F or Cl; and $R_6$ and $R_7$ are each independently methyl; or $R_6$ and $R_7$, together with the carbon atom to which they are attached, form the following structure:

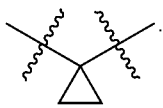 [SMILES: *C1(*)CC1]

13. A compound of formula (III), or a pharmaceutically acceptable salt, solvate, stereoisomer or prodrug thereof:

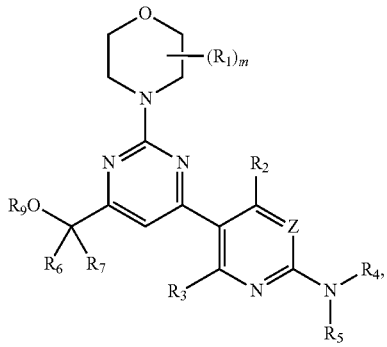

III wherein,
Z is N or $CR_0$, wherein $R_0$ is hydrogen, halogen, $C_{1-10}$ alkyl or $C_{1-10}$ haloalkyl;
$(R_1)_m$ means that the hydrogen atom(s) on the morpholine ring is substituted by $R_1$ and the number of $R_1$ is m, wherein m is 0, 1, 2, 3, 4, 5 or 6, each $R_1$ is the same or different and is independently selected from the group consisting of hydrogen, deuterium, $C_{1-10}$ alkyl, deuterated $C_{1-10}$ alkyl and $C_{1-10}$ haloalkyl; or any two $R_1$ are linked by a single bond or $-(CH_2)_p-$, p is 1, 2, 3, 4, 5 or 6;
$R_2$ and $R_3$ are each independently selected from the group consisting of hydrogen, halogen, $C_{1-10}$ alkyl, $C_{1-10}$ haloalkyl, $C_{1-10}$ alkoxy, $C_{3-8}$ cycloalkoxy, $-COC_{1-10}$ alkyl, $-CON(C_{1-10}$ alkyl$)_2$, $-C(O)OC_{1-10}$ alkyl and $-OC(O)C_{3-10}$ alkyl;
$R_4$ and $R_5$ are each independently selected from the group consisting of hydrogen, $C_{1-10}$ alkyl, $C_{1-10}$ haloalkyl and $C_{3-10}$ cycloalkyl;
$R_6$ and $R_7$ are each independently selected from the group consisting of hydrogen, halogen, $C_{1-10}$ alkyl and $C_{1-10}$ haloalkyl, or $R_6$ and $R_7$, together with the carbon atom to which they are attached, form a 3- to 10-membered saturated or 3- to 6-membered unsaturated monocyclic ring, and 3- to 10-membered saturated or partially unsaturated mono-heterocyclic ring containing 1-3 heteroatoms independently selected from the group consisting of nitrogen, oxygen and sulfur; and
$R_9$ is selected from the group consisting of hydrogen, $C_{1-10}$ alkyl, $C_{1-10}$ haloalkyl, $C_{6-10}$ aryl, $C_{3-10}$ cycloalkyl, $-(CR_aR_b)_r-C_{6-10}$ aryl and $-C(O)C_{1-10}$ alkyl; $R_a$ and $R_b$ are each independently hydrogen or $C_{1-10}$ alkyl, and r is 1, 2 or 3.

14. A compound of formula (I-a-1), formula (I-a-2), formula (I-b-1) or formula (I-b-2), or a pharmaceutically acceptable salt, solvate, stereoisomer or prodrug thereof:

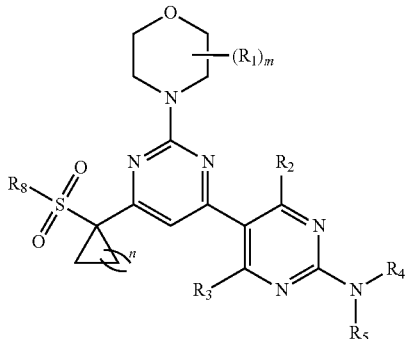

(I-a-1)

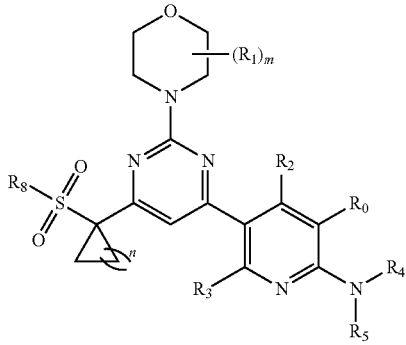

(I-a-2)

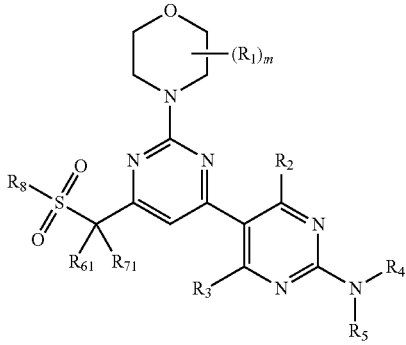

(I-b-1)

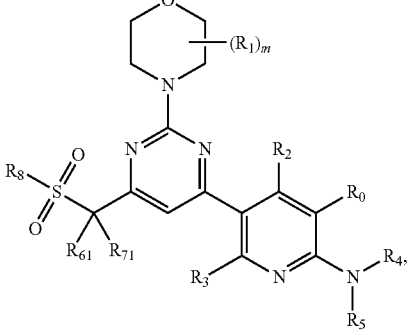

(I-b-2)

wherein, n is 1, 2, 3 or 4;
$R_0$ is hydrogen, halogen, $C_{1-10}$ alkyl or $C_{1-10}$ haloalkyl;
$(R_1)_m$ means that the hydrogen atom(s) on the morpholine ring is substituted by $R_1$ and the number of $R_1$ is m, wherein m is 0, 1, 2, 3, 4, 5 or 6, each $R_1$ is the same or different and is independently selected from the group consisting of hydrogen, deuterium, $C_{1-10}$ alkyl, deuterated $C_{1-10}$ alkyl and $C_{1-10}$ haloalkyl; or any two $R_1$ are linked by a single bond or $-(CH_2)_p-$, p is 1, 2, 3, 4, 5 or 6;

R₂ and R₃ are each independently selected from the group consisting of hydrogen, halogen, $C_{1-10}$ alkyl, $C_{1-10}$ haloalkyl, $C_{1-10}$ alkoxy, $C_{3-8}$ cycloalkoxy, —$COC_{1-10}$ alkyl, —$CON(C_{1-10}$ alkyl)$_2$, —$C(O)OC_{1-10}$ alkyl and —$OC(O)C_{1-10}$ alkyl;

R₄ and R₅ are each independently selected from the group consisting of hydrogen, $C_{1-10}$ alkyl, $C_{1-10}$ haloalkyl and $C_{3-10}$ cycloalkyl;

R₈ is selected from the group consisting of hydroxy, halogen, —$N(R_{81}R_{82})_2$, —$OC_{1-10}$ alkyl, $C_{1-10}$ alkyl, $C_{1-10}$ haloalkyl, $C_{6-10}$ aryl, $C_{3-10}$ cycloalkyl, —$(CR_aR_b)_r$—$C_{6-10}$ aryl, and 5- to 6-membered monocyclic heteroaryl ring, wherein the aryl is unsubstituted or substituted with 1 to 5 substituents selected from the group consisting of halogen and $C_{1-10}$ alkyl; $R_{81}$ and $R_{82}$ are each independently hydrogen or $C_{1-10}$ alkyl; $R_a$ and $R_b$ are each independently hydrogen or $C_{1-10}$ alkyl, and r is 1, 2 or 3; and R₆₁ and R₇₁ are each independently selected from the group consisting of hydrogen, halogen, $C_{1-6}$ alkyl and $C_{1-6}$ haloalkyl.

15. A compound, wherein the compound is:

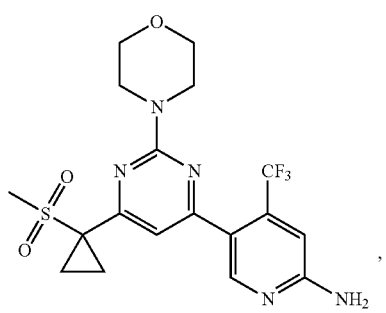

,

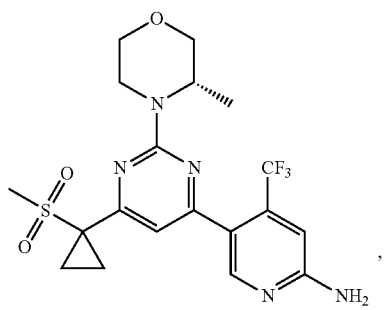

,

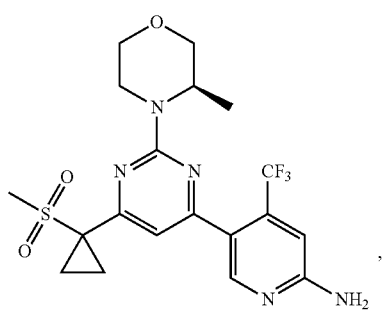

,

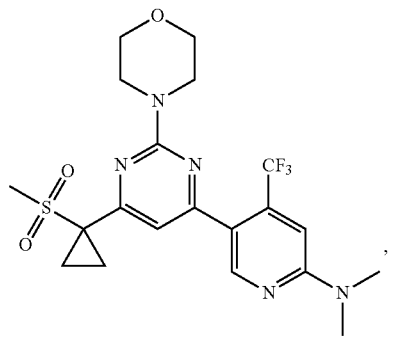

,

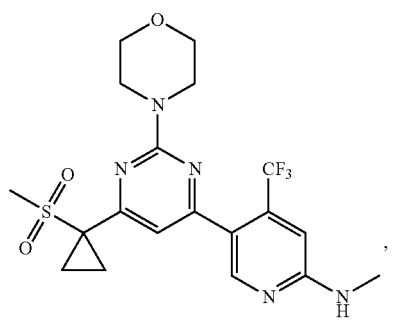

,

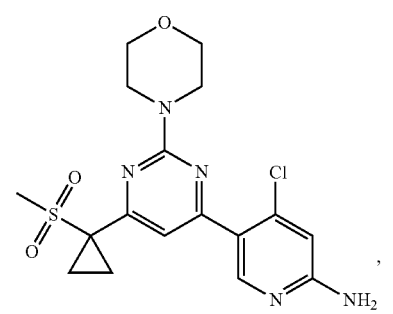

,

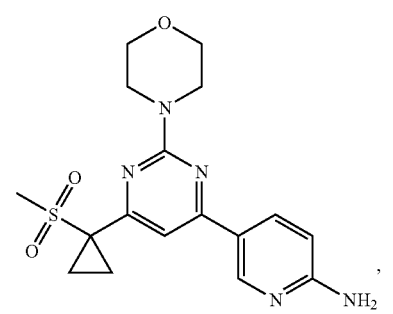

,

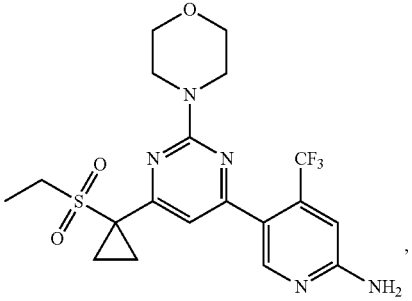

,

131
-continued
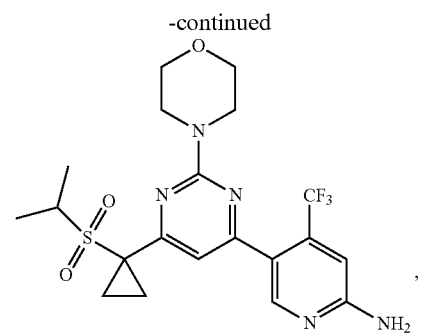,
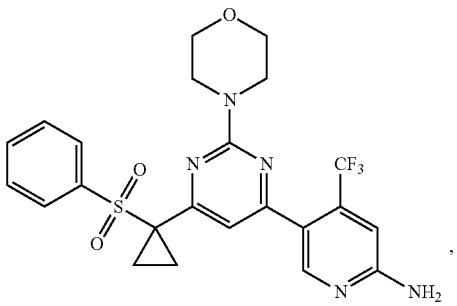,
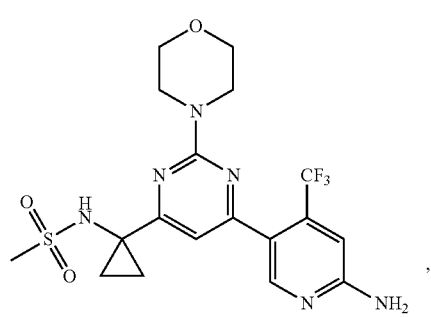,
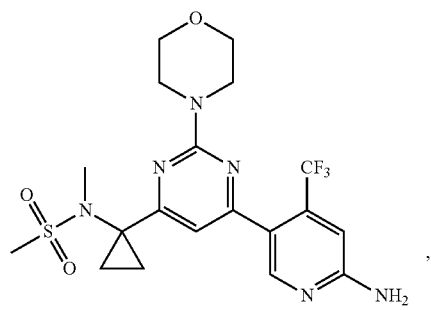,
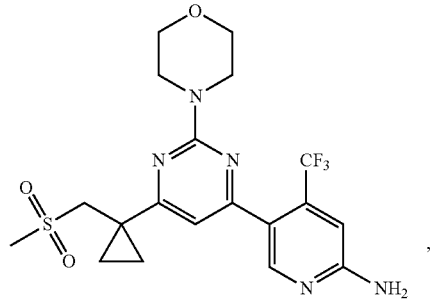,
132
-continued
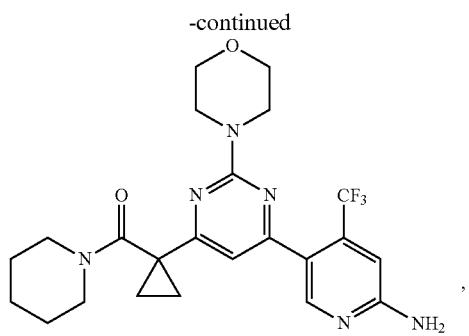,
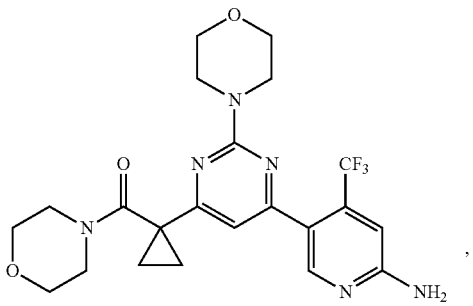,
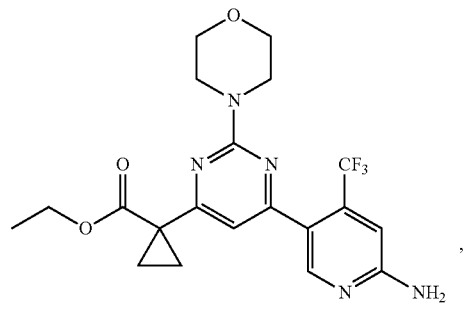,
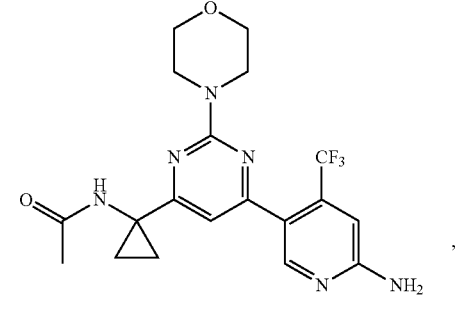,
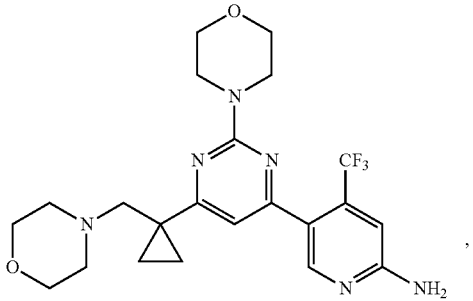, 133
-continued
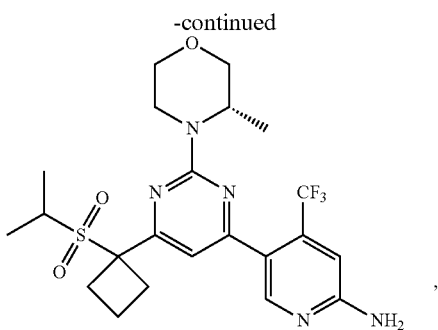
,
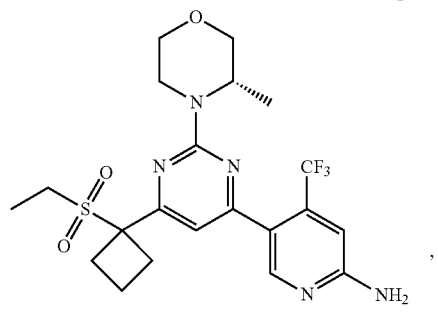
,
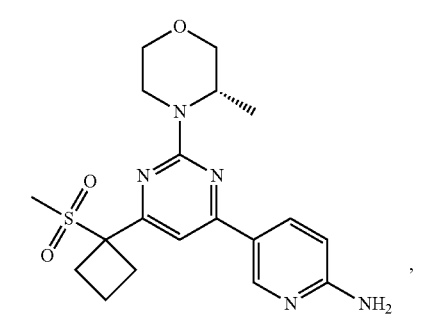
,
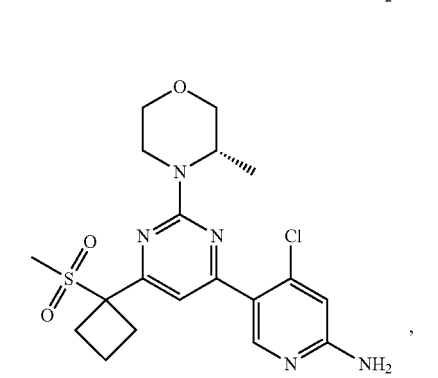
,
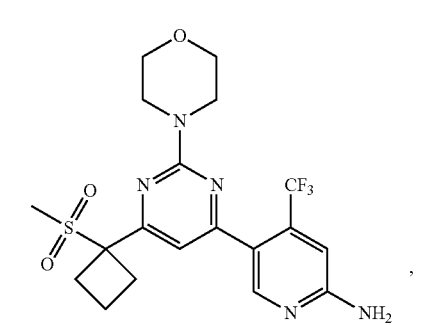
,
134
-continued
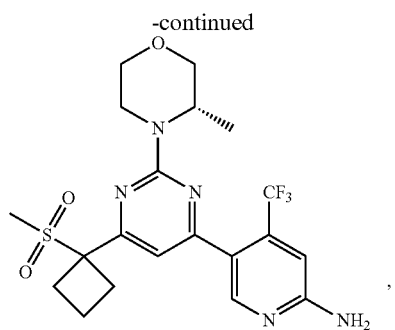
,
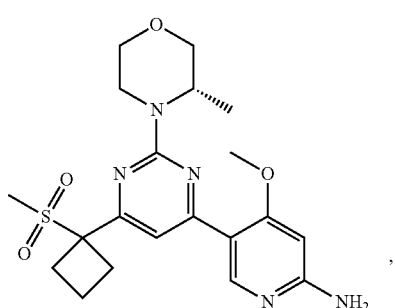
,
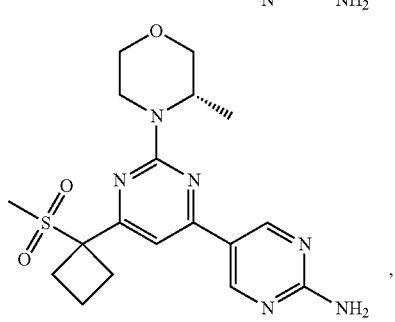
,
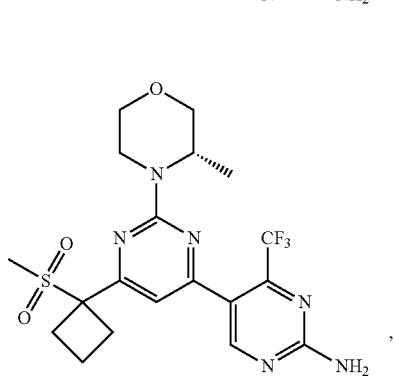
,
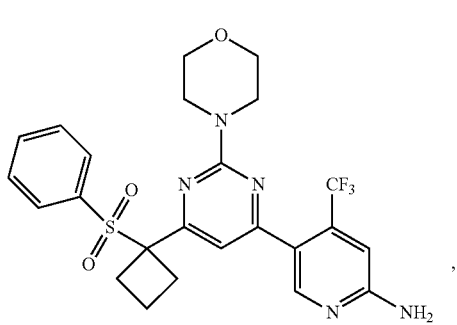
,

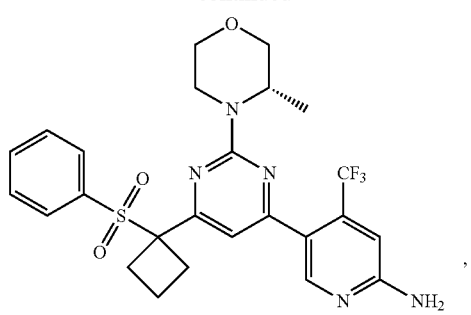
,
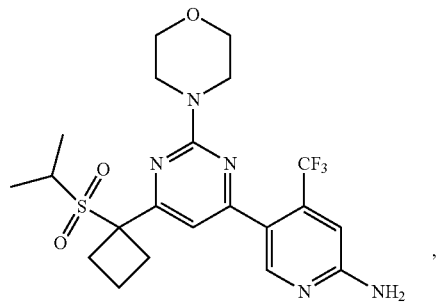
,
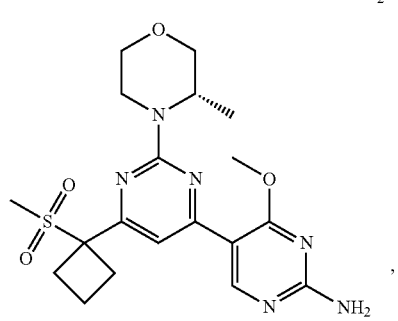
,
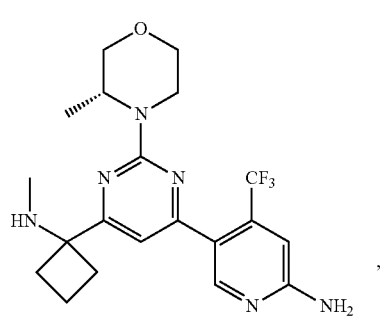
,
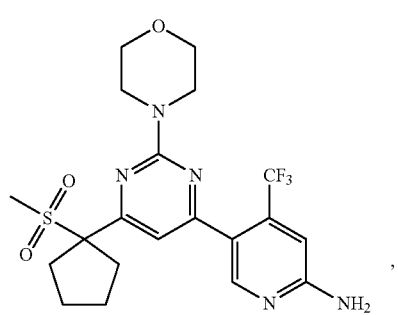
,
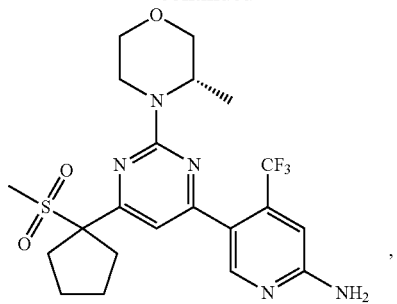
,
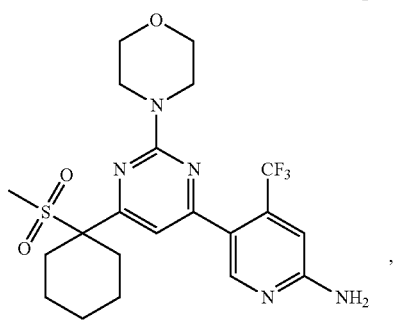
,
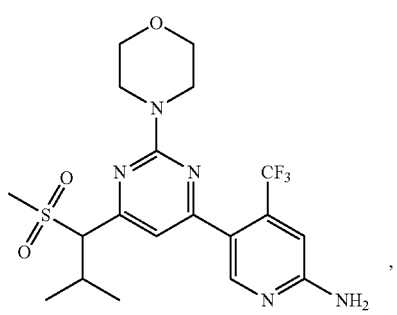
,
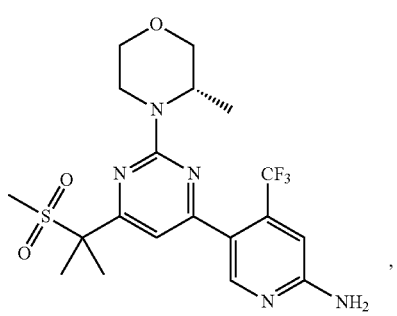
,
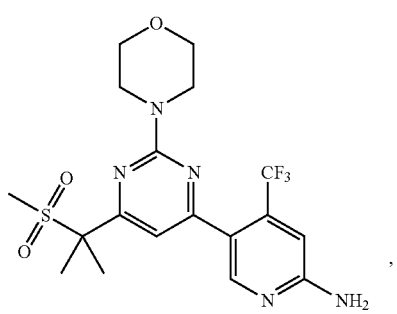
, -continued
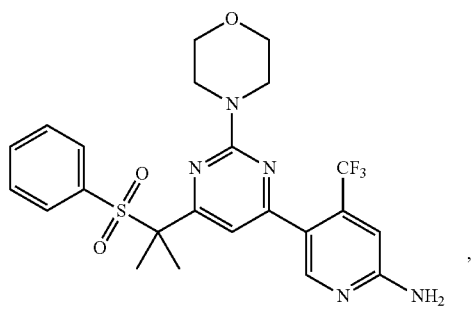
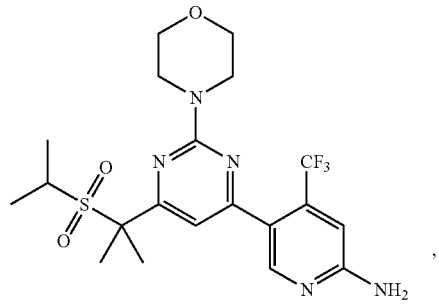
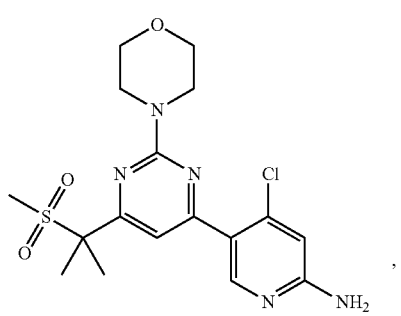
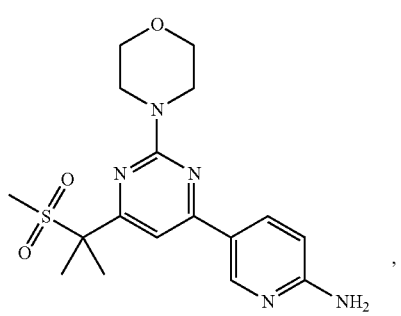
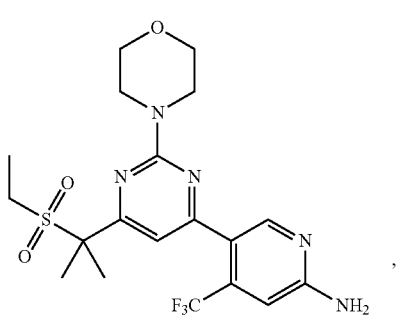
-continued
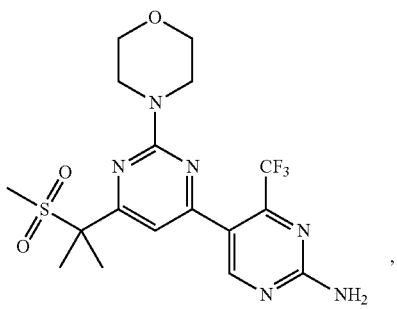
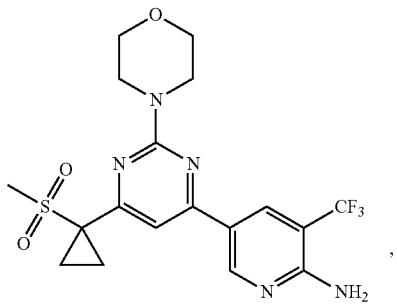
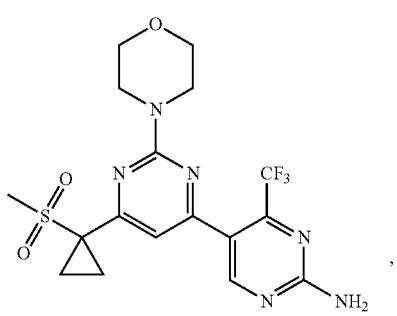
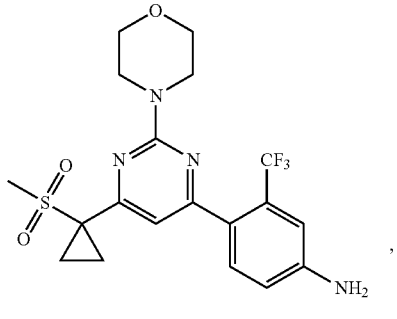
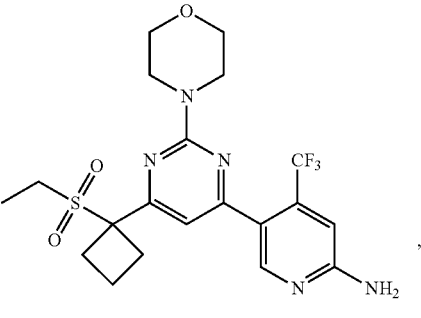

-continued
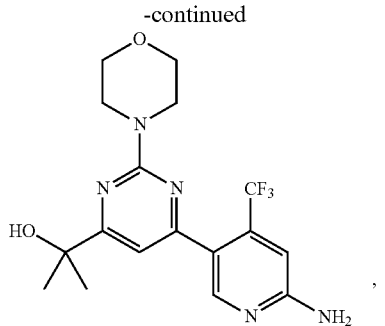
,
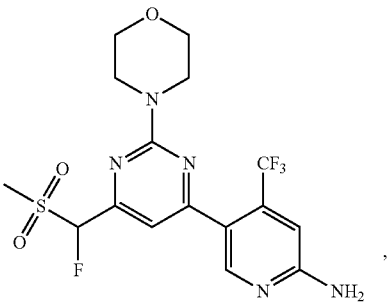
,
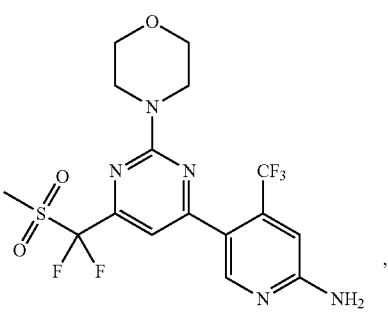
,
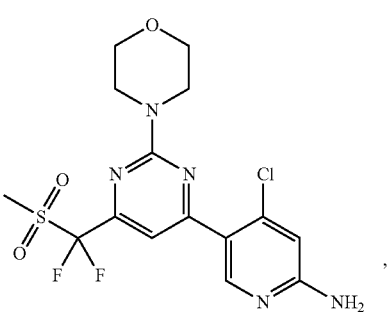
,
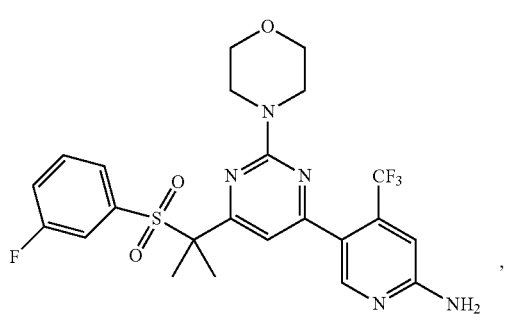
,
-continued
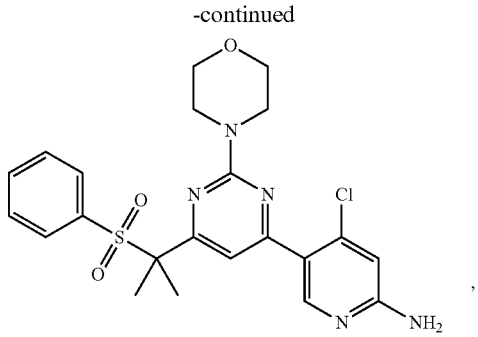
,
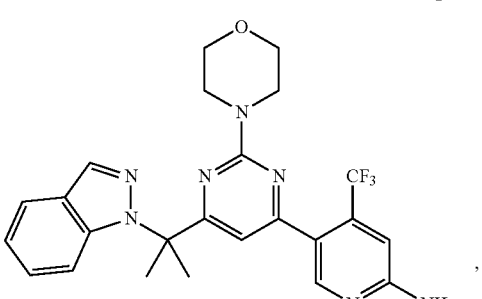
,
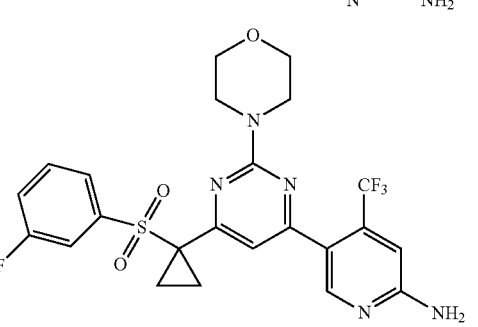
,
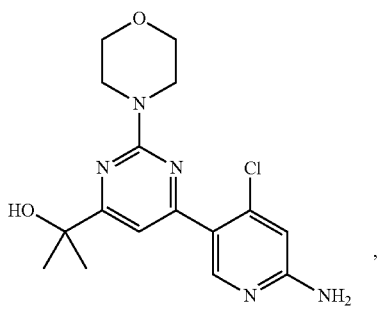
,
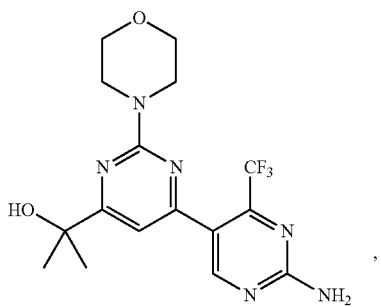
, 141
-continued
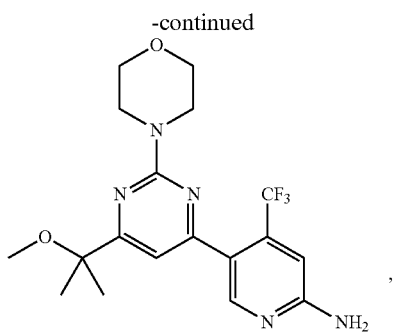
,
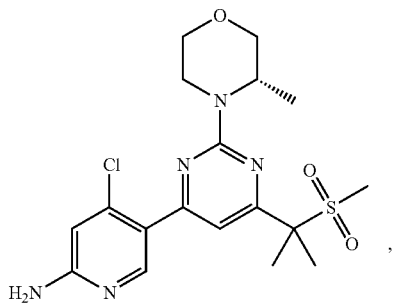
,
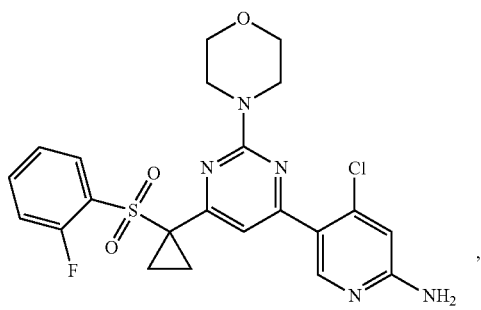
,
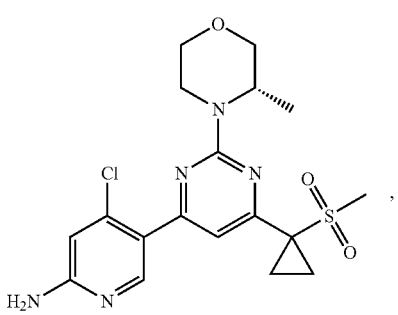
,
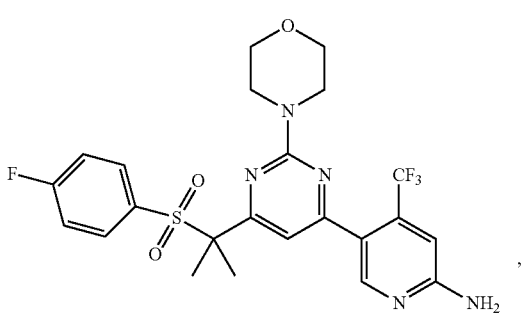
,
142
-continued
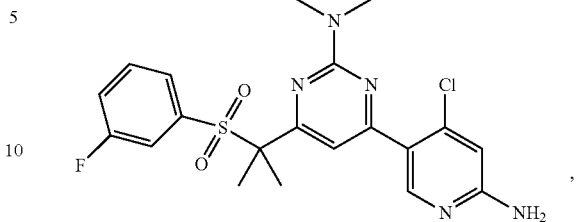
,
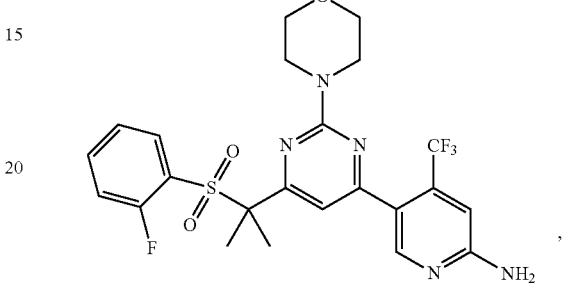
,
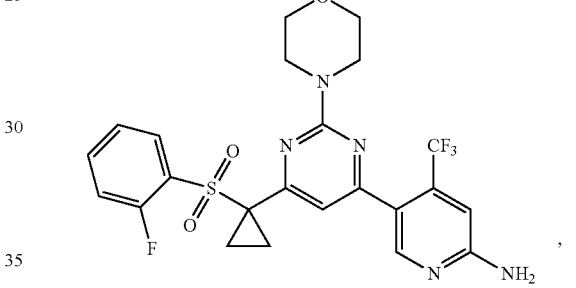
,
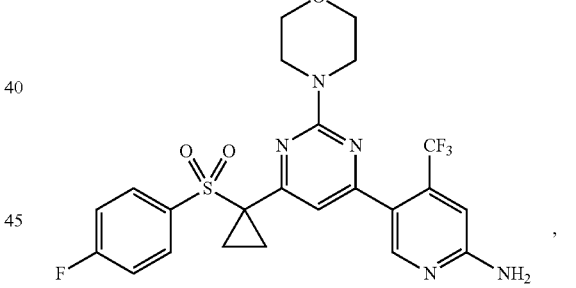
, or
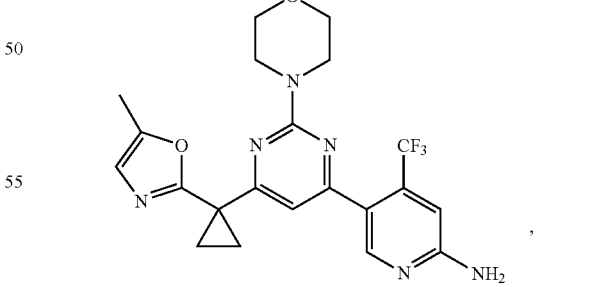
,
or a pharmaceutically acceptable salt, solvate, stereoisomer or prodrug thereof.
16. The compound or the pharmaceutically acceptable salt, solvate, stereoisomer or prodrug thereof according to claim 11, wherein it is selected from the group consisting of the following:

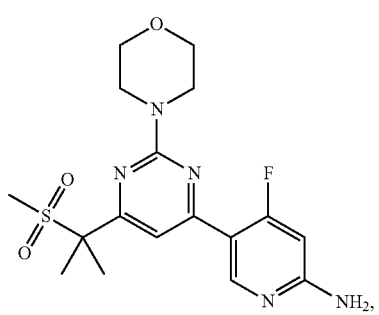
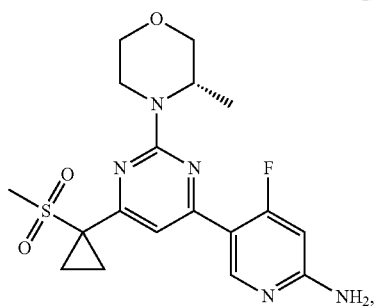
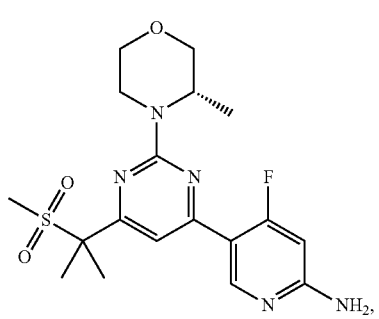
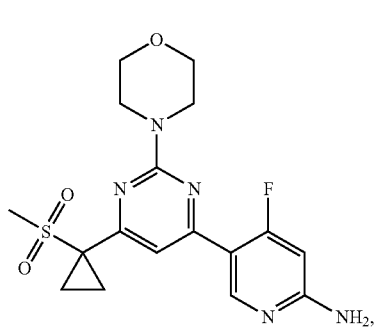
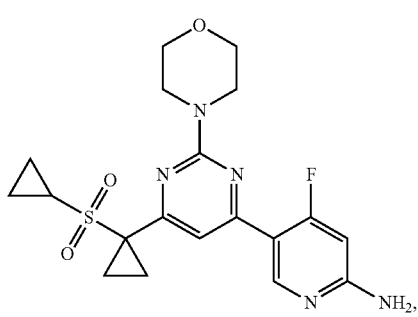

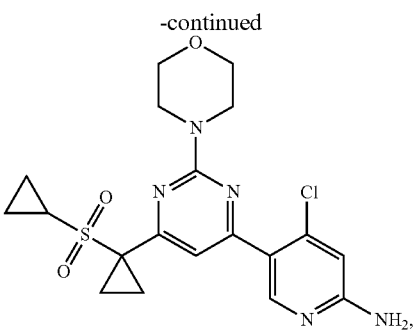
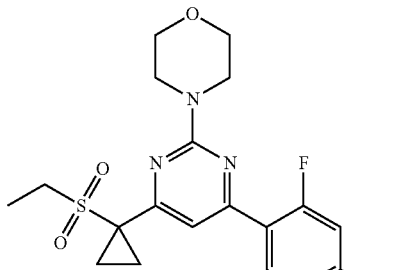
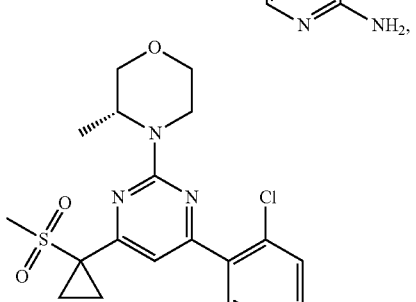
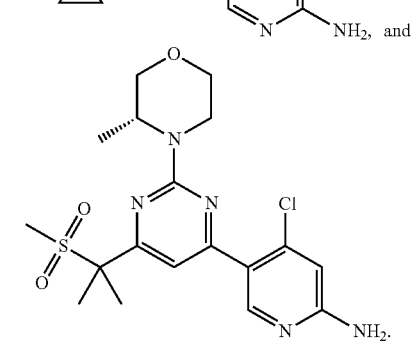

17. A pharmaceutical composition comprising the compound or the pharmaceutically acceptable salt, solvate, stereoisomer, or prodrug thereof according to claim 1; and a pharmaceutically acceptable carrier.

18. A pharmaceutical composition comprising the compound or the pharmaceutically acceptable salt, solvate, stereoisomer, or prodrug thereof according to claim 15, and a pharmaceutically acceptable carrier.

19. A method for inhibiting PI3K kinase in a subject in need thereof, the method comprising administering to the subject the pharmaceutical composition of claim 17.

20. The method according to claim 19, wherein the subject is in need of treatment of a cancer selected from the group consisting of melanoma, papillary thyroid neoplasms, cholangiocarcinoma, colon cancer, ovarian cancer, endometrial cancer, cervical cancer, lung cancer, esophageal cancer, brain cancer, malignant lymphoma, liver cancer, stomach cancer, kidney cancer, bladder cancer, prostate cancer, breast cancer, pancreatic cancer, and sarcoma.

21. The method according to claim 20, wherein the cancer is breast cancer.

22. A method for inhibiting PI3K kinase in a subject in need thereof, the method comprising administering to the subject the pharmaceutical composition of claim 18.

23. The method according to claim 22, wherein the subject is in need of treatment of a cancer selected from the group consisting of melanoma, papillary thyroid neoplasms, cholangiocarcinoma, colon cancer, ovarian cancer, endometrial cancer, cervical cancer, lung cancer, esophageal cancer, brain cancer, malignant lymphoma, liver cancer, stomach cancer, kidney cancer, bladder cancer, prostate cancer, breast cancer, pancreatic cancer, and sarcoma.

24. The method according to claim 23, wherein the cancer is breast cancer.

* * * * *